US012582141B2

(12) United States Patent
Paloheimo et al.

(10) Patent No.: US 12,582,141 B2
(45) Date of Patent: Mar. 24, 2026

(54) POLYPEPTIDES HAVING PHYTASE ACTIVITY

(71) Applicant: AB Enzymes Finland Oy, Rajamäki (FI)

(72) Inventors: Marja Paloheimo, Rajamäki (FI); Merja Oja, Rajamäki (FI); Stefanie Scholten, Darmstadt (DE); Dietrich Löbel, Trebur (DE); Kari Juntunen, Rajamäki (FI); Sandra Meyerjürgens, Mainaschaff (DE); Hanna-Mari Meriläinen, Rajamäki (FI); Thomas Haarmann, Darmstadt (DE); Imke Kühn, Darmstadt (DE); Terhi Puranen, Rajamäki (FI)

(73) Assignee: AB Enzymes Finland Oy (FI)

( * ) Notice: Subject to any disclaimer, the term of this patent is extended or adjusted under 35 U.S.C. 154(b) by 1275 days.

(21) Appl. No.: 17/416,289

(22) PCT Filed: Dec. 9, 2019

(86) PCT No.: PCT/FI2019/050875
§ 371 (c)(1),
(2) Date: Jun. 18, 2021

(87) PCT Pub. No.: WO2020/128152
PCT Pub. Date: Jun. 25, 2020

(65) Prior Publication Data
US 2022/0046956 A1 Feb. 17, 2022

(30) Foreign Application Priority Data
Dec. 21, 2018 (EP) .................................... 18215119

(51) Int. Cl.
*A23K 20/189* (2016.01)
*A23J 1/12* (2006.01)
(Continued)

(52) U.S. Cl.
CPC ............. *A23K 20/189* (2016.05); *A23J 1/125* (2013.01); *A23K 10/14* (2016.05); *A23K 50/75* (2016.05);
(Continued)

(58) Field of Classification Search
CPC ...... A23K 20/189; A23K 10/14; A23K 50/75; A23J 1/125; A23L 5/25; A23L 33/10; C12N 9/16; C12Y 301/03008; C12Y 301/03026
See application file for complete search history.

(56) References Cited

U.S. PATENT DOCUMENTS

| | | | |
|---|---|---|---|
| 5,834,286 A | 11/1998 | Nevalainen et al. |
| 2010/0278965 A1 | 11/2010 | Boze et al. |
| 2015/0037491 A1 | 2/2015 | Gebert |

FOREIGN PATENT DOCUMENTS

| | | |
|---|---|---|
| CN | 107858364 A | 3/2018 |
| KR | 20010003164 A | 1/2001 |

(Continued)

OTHER PUBLICATIONS

"AppA family phytase/histidine-type acid phosphatase [Budvicia aquatica]", NCBI Reference Sequence: WP_029095759,retrieved at https://Awww.ncbi.nim.nih.gov/protein/WP_029095759.1 (Nov. 7, 2018) (Year: 2018).*

(Continued)

*Primary Examiner* — Emily M Le
*Assistant Examiner* — Carrie Glimm
(74) *Attorney, Agent, or Firm* — Elmore Patent Law Group, P.C.; Joseph C. Zucchero; Carolyn S. Elmore

(57) ABSTRACT
The present invention discloses novel phytases that have improved phytase activity, compositions comprising them,
(Continued)

recombinant host cells suitable for their production, and their use in feed applications.

11 Claims, 13 Drawing Sheets

Specification includes a Sequence Listing.

(51) Int. Cl.

| | |
|---|---|
| *A23K 10/14* | (2016.01) |
| *A23K 50/75* | (2016.01) |
| *A23L 5/20* | (2016.01) |
| *A23L 33/10* | (2016.01) |
| *C12N 9/16* | (2006.01) |

(52) U.S. Cl.
CPC ................. *A23L 5/25* (2016.08); *A23L 33/10* (2016.08); *C12N 9/16* (2013.01); *C12Y 301/03008* (2013.01); *C12Y 301/03026* (2013.01)

(56) References Cited

FOREIGN PATENT DOCUMENTS

| WO | 2006063588 A1 | 6/2006 |
|---|---|---|
| WO | 2017001701 A1 | 1/2017 |
| WO | 2017216233 A1 | 12/2017 |

OTHER PUBLICATIONS

Database UniProt [online] Dec. 5, 2018, entry version 27. ID-E5Y8B1_BILWA; OS—Bilophila wadsworthia 3_1_6; "SubName: Full=Uncharacterized protein {ECO:0000313|EMBL:EFV43737.1}"; Retrieved Apr. 3, 2020.

Database UniProt [online] Dec. 5, 2018; entry version 26. ID-E8LI73_SUCHY; OS—Succinatimonas hippei; "SubName: Full=Histidine acid phosphatase {ECO:0000313|EMBL:EFY07805.1}"; Retrieved Apr. 3, 2020.

Database UniProt [online] Nov. 7, 2018, entry version 5. ID-A0A2C6DQ33_9GAMM; OS—Budvicia aquatica; "SubName: Full=AppA family phytase/histidine-type acid phosphatase {ECO:0000313| EMBL:PHI30911.1}". Retrieved May 3, 2020.

Database UniProt [online] Jan. 31, 2018, entry version 12. ID-A0A060SXP8_BLAAD; OS—Blastobotrys adeninivorans (Yeast) (Arxula adeninivorans); "SubName: Full=ARAD1A14476p {ECO:0000313| EMBL:CDP33665.1}" ; Retrieved Apr. 3, 2020.

"Histidine-type phosphatase", Database RefSeq Jul. 7, 2017—Accession No. WP_005028276.

Bedford, M. R et al., "Reduction of phytate to tetrakisphosphate (IP4) to trisphosphate (IP3), or perhaps even lower, does not remove its antinutritive properties", In: Phytate destruction—consequences for precision animal nutrition. Ch. 3. Eds. Walk, C.L., et al., Wageningen Academic publishers, 2016, 45-51.

Blaabjerg, K. et al., "High-performance ion chromatography method for separation and quantification of inositol phosphates in diets and digesta", J. Chromatogr. B, 878, 2010, 347-354.

Greiner, R. et al., "Update on characteristics of commercial phytases", International Phytase Summit 201296-107.

Lassen, S. F. et al., "Expression gene cloning and characterization of five novel phytases from four basidiomycete fungi: *Peniophora lycii, Agrocybe pediades*, a *Ceriporia* sp., and *Trametes pubescens*", Appl. Environ. Microbiol., vol. 67, No. 10, Oct. 2001, 4701-47017.

Lee, S. A. et al., "Inositol—An effective growth promotor?", World's Poultry Science Journal, 72, 2016, 743-760.

Menezes-Blackburn, D. S. et al., "Performance of Seven Commercial Phytases in an in Vitro Simulation of Poultry Digestive Tract", J Agric. Food Chem., 63, Jun. 25, 2015, 6142-6149.

Ragon, M. et al., "Complete hydrolysis of myo-inositol hexakisphosphate by a novel phytase from Debaryomyces castellii CBS 2923", Appl. Microbiol. Biotech., vol. 78, 2008, 47-53.

Xu, P. et al., "Interaction of Inositol Phosphates with Calcium, Zinc, and Histidine", J. Inorganic Biochem, 47, 1992, 119-130.

Wyss, M. et al., "Biochemical characterization of fungal phytases (myo-inositol hexakisphosphate phosphohydrolases): Catalytic properties", Appl. Environ. Microbiol., vol. 65, No. 2, Feb. 1, 1999, 367-373.

Zeller, E. et al., "Hydrolysis of phytate and formation of inositol phosphate isomers without or with supplemented phytases in different segments of the digestive tract of broilers", J. of Nutritional Sci., vol. 4, e1, 2015, 1-12.

"AppA family phytase/histidine-type acid phosphatase [Budvicia aquatica]", NCBI Reference Sequence: WP_029095759, retrieved at https://www.ncbi.nlm.nih.gov/protein/WP_029095759.1, Publication year 2018.

* cited by examiner

| | EcoWNT | BA59 | YE76 | PSd32 | PSd34 | PSd35 | PSd65 | PSd67 | ASPAW | PS203 | PSK207 | PSK235 | PSK262 | PSK256 | PSK260 | PSK267_B | PSK268_3MC |
|---|---|---|---|---|---|---|---|---|---|---|---|---|---|---|---|---|---|
| EcoWNT | 100% | 43% | 43.4% | 25.7% | 31.5% | 28.7% | 34.2% | 28.6% | 15.4% | 16.7% | 14% | 12.9% | 17.8% | 14.2% | 13.6% | 14.9% | 13% |
| BA59 | 43% | 100% | 60.2% | 29.2% | 30.9% | 32.4% | 33.2% | 28.5% | 15.5% | 15.7% | 15.6% | 14.2% | 17% | 14.3% | 15.8% | 14.3% | 15.1% |
| YE76 | 43.4% | 60.2% | 100% | 30.3% | 30.2% | 31.4% | 33.3% | 28.4% | 17.3% | 12% | 14.9% | 12.6% | 15.6% | 16.3% | 13.6% | 15.2% | 12.6% |
| PSd32 | 25.7% | 29.2% | 30.3% | 100% | 47.1% | 47.4% | 28.9% | 19.2% | 13% | 17% | 14.5% | 14.5% | 14.3% | 14.2% | 14% | 14.1% | 14.3% |
| PSd34 | 31.5% | 30.9% | 30.2% | 47.1% | 100% | 75.9% | 30.4% | 22.4% | 13.9% | 15.5% | 16.4% | 12.4% | 16% | 15.5% | 14.9% | 13.7% | 15.6% |
| PSd35 | 28.7% | 32.4% | 31.4% | 47.4% | 75.9% | 100% | 28.5% | 23.9% | 14% | 16.1% | 15.4% | 12.4% | 16.2% | 13.6% | 15.8% | 15% | 17.8% |
| PSd65 | 34.2% | 33.2% | 33.3% | 28.9% | 30.4% | 28.5% | 100% | 36.3% | 16% | 14.1% | 17.5% | 17.2% | 16.1% | 15.9% | 16.4% | 15.5% | 15.2% |
| PSd67 | 28.6% | 28.5% | 28.4% | 19.2% | 22.4% | 23.9% | 36.3% | 100% | 14.3% | 12.1% | 17.2% | 15.1% | 16.1% | 15.8% | 14.9% | 16.8% | 13.9% |
| ASPAW | 15.4% | 15.5% | 17.3% | 13% | 13.9% | 14% | 16% | 14.3% | 100% | 24% | 26.4% | 36.6% | 62.1% | 65.8% | 43.9% | 45.2% | 49.4% |
| PS203 | 15.7% | 15.7% | 12% | 17% | 15.5% | 16.1% | 14.1% | 12.1% | 24% | 100% | 30% | 25.6% | 25% | 24% | 22.7% | 20.9% | 20.4% |
| PSK207 | 14% | 15.6% | 14.9% | 14.5% | 16.4% | 15.4% | 17.5% | 17.2% | 26.4% | 30% | 100% | 23.5% | 23.5% | 26.1% | 25.4% | 24.2% | 24.7% |
| PSK235 | 12.9% | 14.2% | 12.6% | 14.5% | 12.4% | 12.4% | 17.2% | 15.1% | 36.6% | 25.6% | 23.5% | 100% | 38.9% | 35.5% | 33.8% | 35.6% | 36.7% |
| PSK262 | 17.8% | 17% | 15.6% | 14.3% | 16% | 16.2% | 16.1% | 16.1% | 62.1% | 25% | 23.5% | 38.9% | 100% | 60.7% | 46% | 46.4% | 52.2% |
| PSK256 | 14.2% | 14.3% | 16.3% | 14.2% | 15.5% | 13.6% | 15.9% | 15.8% | 65.8% | 24% | 26.1% | 35.5% | 60.7% | 100% | 44.8% | 47% | 50.7% |
| PSK260 | 13.6% | 15.8% | 13.6% | 14% | 14.9% | 15.8% | 16.4% | 14.9% | 43.9% | 22.7% | 25.4% | 33.8% | 46% | 44.8% | 100% | 41.6% | 44.8% |
| PSK267_B | 14.9% | 14.3% | 15.2% | 14.1% | 13.7% | 15% | 15.5% | 16.8% | 45.2% | 20.9% | 24.2% | 35.6% | 46.4% | 47% | 41.6% | 100% | 51.3% |
| PSK268_3MC | 13% | 15.1% | 12.6% | 14.3% | 15.6% | 17.8% | 15.2% | 13.9% | 49.4% | 20.4% | 24.7% | 36.7% | 52.2% | 50.7% | 44.8% | 51.3% | 100% |

Fig. 10

POLYPEPTIDES HAVING PHYTASE ACTIVITY

FIELD OF THE INVENTION

This invention relates to polypeptides having phytase activity, methods for their production, and to compositions comprising such polypeptides.

BACKGROUND

Phytic acid (phytate, inositol hexakisphosphate, IP6) is found in many plants where it functions as storage of phosphate. Phosphate stored in IP6 molecules can be released as inorganic phosphate. When inorganic phosphate is released from phytic acid molecules, IP6 is converted to lower inositol phosphates pentaphosphate (IP5), tetraphosphate (IP4), trisphosphate (IP3), bisphosphate (IP2) and monophosphate (IP).

Phytases are a group of phosphatase enzymes that catalyze the hydrolysis of phytic acid. The commercially available phytases all belong to the histidine acid phosphatase (HAP) protein family. The phytases belonging to the HAP protein family share conserved N-terminal active site heptapeptide motif RHGXRXP and the catalytically active HD-dipeptide at the C-terminus. Histidine acid phosphatases are part of a larger superfamily of histidine phosphatases. The histidine phosphatase superfamily is a large functionally diverse group of proteins. They share a conserved catalytic core centered on a histidine which becomes phosphorylated during the course of the reaction. PFAM motif His_Phos_2 (PF00328) represents branch 2 of the histidine phosphatase superfamily, the branch containing mainly acid phosphatases and phytases.

Phytases are used in feeds to improve phosphate availability from feed ingredients of plant origin (e.g. wheat, barley, corn, soybean) by phytate degradation. This is in particular of interest for monogastric animals like poultry, fish and pigs, because intestinal phytate degradation within their upper intestinal tract is limited. This limitation not just restricts phosphorus utilization but also availability of other nutrients due to the chelating effect of inositol phosphates and is a reason why at least IP6 to IP4 should be dephosphorylated as far as possible. The efficiency of several prior phytases currently used in animal feed application are rather efficient but efficiency of the degradation of IP6 to IP1 should still be improved, to further increase phosphate and other nutrients availability for the animal.

Phytate breakdown by phytases is associated with stepwise degradation of IP6 to lower inositol phosphate esters (IP5, IP4, IP3, IP2, and IP1). The use of industry standard levels of phytase have, expectedly, shown to significantly reduce IP6 levels in vitro and in vivo. However, with IP6 degradation an increase of IP4 and IP3 has been detected in ileal digesta which shows that the hydrolytic cleavage of the first phosphate group is not the only limiting step in phytate degradation (e.g. Zeller et al., 2015; Menezes-Blackburn et al., 2015). As even these lower inositol phosphates have antinutritive properties due to binding of different nutrients like minerals (Xu et al., 1992), the target in animal feeding is to degrade IP esters up to the terminal ileum (Bedford and Walk, 2016). Another reason for the aim to get inositol fully released is that increasing the content of free inositol has been shown to improve growth performance in animals by different mechanisms, still under investigation (Lee and Bedford, 2016).

The part in the intestinal tract of animals where optimal degradation of inositol phosphate esters takes place with phytase supplements is the stomach due to its low pH, leading to the best substrate (phytate) solubility. Retention time in the stomach is short and part of the content might flush rapidly to the intestinal tract in which the pH is neutral. Therefore, further development of phytases acting quickly and more effectively on IP6 and, also on lower inositol phosphates like IP4 and IP3 isomers, is of relevance for the animal feeding industry. These type of phytases would further improve intestinal availability of phosphate and inositol.

SUMMARY

It is an object of the invention to provide novel polypeptides that have phytase activity, and that are suitable for feed and food applications. The present polypeptides are useful in increasing the nutritional value of feed or food by releasing inorganic phosphate from phytic acid, which is present in feed or food of plant origin. It is another object of the invention to provide novel feeds and additives.

The polypeptides of the present invention have improved phytate degrading activity and/or specificity against phytic acid and/or lower inositol phosphates found in plant material or degraded from those. The polypeptides of the invention are preferably histidine acid phosphatases and they have improved ability to release inorganic phosphate from plant material, thereby making them suitable for the use in animal feed to improve nutritional value of feed. The polypeptides of the invention have improved activity in consecutive degradation of IP6 to lower inositol phosphates and are superior in degrading lower IPs like IP4 when compared to prior phytases, such as the E. coli mutant phytase in Quantum Blue (QB) which was used as a benchmark commercial product in the tests described in the Examples.

The present inventors have found a limited set of histidine acid phosphatases that are useful for production in industrial scale and that have properties that make them suitable for feed application. The inventors have also found that it is not possible to predict performance of a candidate phytase based simply on sequence similarity or screening for one or few properties (such as pH optimum, production yield, or temperature stability). Thus, database polypeptides annotated as phytases based on sequence analysis are not necessarily useful in the applications the present phytases are intended for. Moreover, the specificity of an enzyme towards a certain inositol phosphate cannot be predicted based on sequence analysis.

The inventors found that testing a candidate phytase e.g. for feed applications analysed in an environment which simulates conditions of the gastrointestinal tract (Gastrointestinal tract simulation assay, GIT) of animals like poultry is much more informative as it bundles several circumstances that are relevant for the effectivity of a phytase to be used as a feed additive. In fact, most candidate phytases annotated as putatively having phytase activity fail to show any significant phytase activity, or their production is not successful in a recombinant host. Thus, the polypeptides of the present invention make together a uniform group of phytases, and show effectiveness in the GIT assay and suitability for feed applications.

According to the first aspect is provided a polypeptide having phytase activity, wherein the polypeptide is selected from the group consisting of:
    a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15);

wherein the polypeptide is an isolated, recombinant or synthetic polypeptide.

All polypeptides of the first aspect embody the common inventive concept of the present invention. They are structurally similar in the class of phytases and they share same functional characteristics. They also have high activity on lower inositol phosphates like IP4 and can be used in feed applications either alone or in combination with other phytases. Accordingly, it is an object of the present invention to provide phytases, and composition containing them, that have preference for IP4 in order to enhance degradation of higher inositol phosphate esters into lower inositol phosphate esters lighter components.

According to the second aspect is provided a composition comprising the polypeptide of the first aspect and at least one feedingstuff (feed ingredient) or additive selected from at least one of: stabiliser, preservative, mineral and nutrient. In an embodiment the nutrient comprises at least one of oil, vitamin(s), trace mineral(s) and amino acid(s).

The composition is useful in feeding animals, because the composition can be given to animals and the phytases effectively degrade phytate and improve release of nutrients from the components of the composition or from feed.

According to the third aspect is provided a composition comprising at least two polypeptides having phytase activity, and at least one feedingstuff or additive, wherein:

the first polypeptide has phytase activity and is selected from an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and the second polypeptide has phytase activity, does not have an identical amino acid sequence with the first polypeptide, and is selected from *E. coli* mutant phytase QB, an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15).

The compositions can be manufactured by mixing its components together.

According to the fourth aspect is provided animal feed comprising the polypeptide of the first aspect or the composition of the second or third aspect; at least one protein source of plant origin; and a. Optionally at least one further enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate, or a combination thereof.

According to the fourth aspect is provided a feed supplement comprising the polypeptide of the first aspect or the composition of the second aspect; and a. Optionally at least one further enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate, minerals, amino acids, prebiotics, probiotics, or a combination thereof.

According to the fifth aspect is provided use of the polypeptide of the first aspect, or a composition comprising it, for degrading phytic acid. In an embodiment the use involves degrading IP4 or IP6, or both IP4 and IP6, and/or optionally IP3 and IP2. In another embodiment the use involves degrading IP4, IP5 and IP6, and optionally IP3 and IP2.

According to the sixth aspect is provided a method of producing phytase in a recombinant host cell comprising a. providing a polynucleotide comprising genetic elements for producing a phytase comprising an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. expressing the polynucleotide in a recombinant host cell;

wherein the phytase is capable of releasing phosphate from phytic acid.

According to the seventh aspect is provided a recombinant host cell comprising genetic elements for producing at least one polypeptide of the first aspect.

According to another aspect is provided a use of, and a method of using, the polypeptide of the first aspect in animal feed, in animal feed additives, in preparation of a composition for use in animal feed, and/or for improving digestibility of feed.

According to another aspect is provided a use of, and a method of using, the polypeptide of the first aspect in food, in food additives, in preparation of a composition for use in food, and/or for improving digestibility of food.

According to another aspect is provided a process for producing an animal feed comprising combining a nutrient component including one or more of a carbohydrate, fat and protein with the polypeptide of the first aspect, thereby producing the animal feed.

In another aspect is provided a process for increasing the nutritional value of an animal feed comprising providing an animal feed including one or more of carbohydrate, fat and protein, and the polypeptide of the first aspect.

As evidenced by the Examples, the polypeptides and the composition according to the invention have a structure, composition and properties that allow their production in recombinant host cells and make them useful in enzyme compositions for industrial applications. The enzyme composition is particularly good for feed formulations because of the good stability, performance and specific activity.

5

YE76; 4G and 4H, PSd34; 4I and 4J, PSd35; 4K and 4L, PSd65; 4M and 4N, PSd67; 4O and 4P, ASPAW; 4Q and 4R, PSf203; 4S and 4T, PSk256; 4U and 4V, PSk260; 4W and 4X, PSk267.

Figure 5A:
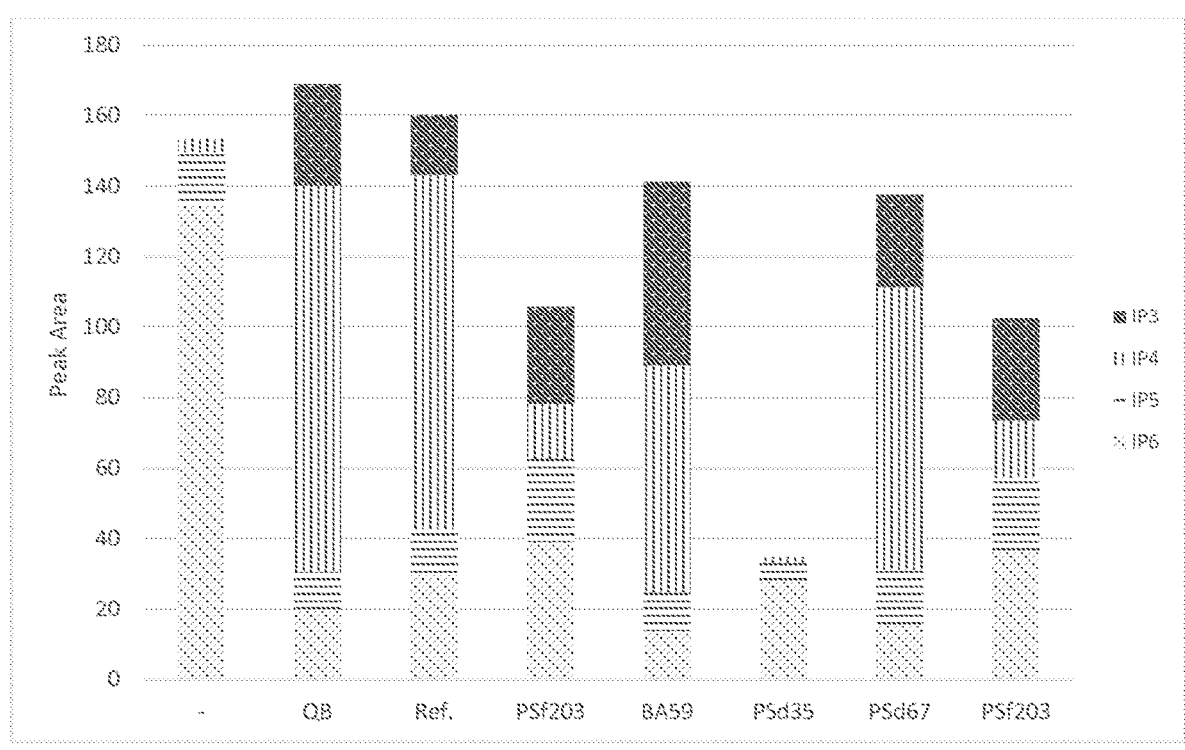
Figure 5B:
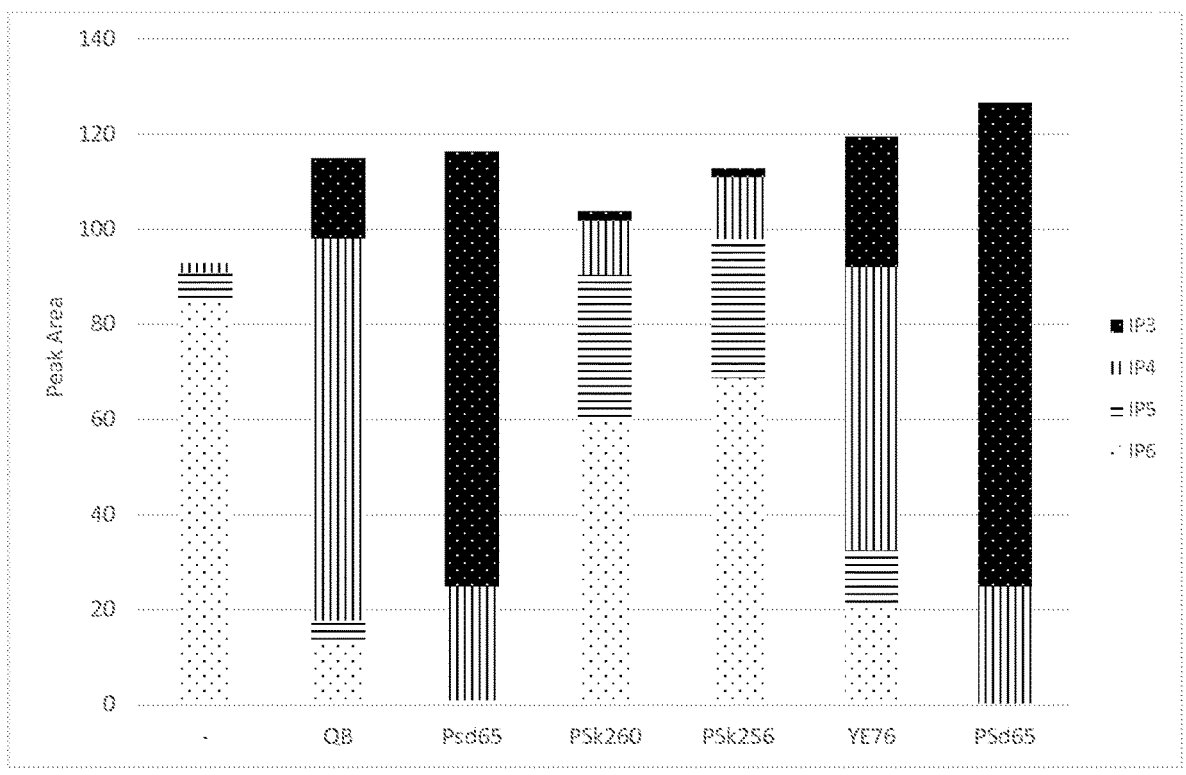

FIG. 5 shows the amounts of IP6 to IP3 inositol phosphates obtained, using phytases selected from screening, after running the GIT assay with corn-soybean meal as substrate and 250 FTU of phytase per kg of corn-soybean-meal mix. Quantum Blue (QB) product and *E. coli* mutant phytase in QB, produced in similar fermentation as the novel phytases (Ref), were used as references. FIG. 5A, PSf203 (results from two parallel tests), BA59, PSd35, PSd67; FIG. 5B, QB, PSd65 (results from two parallel tests), PSk260, PSk256, YE76. -, no phytase added.

Figure 6A:
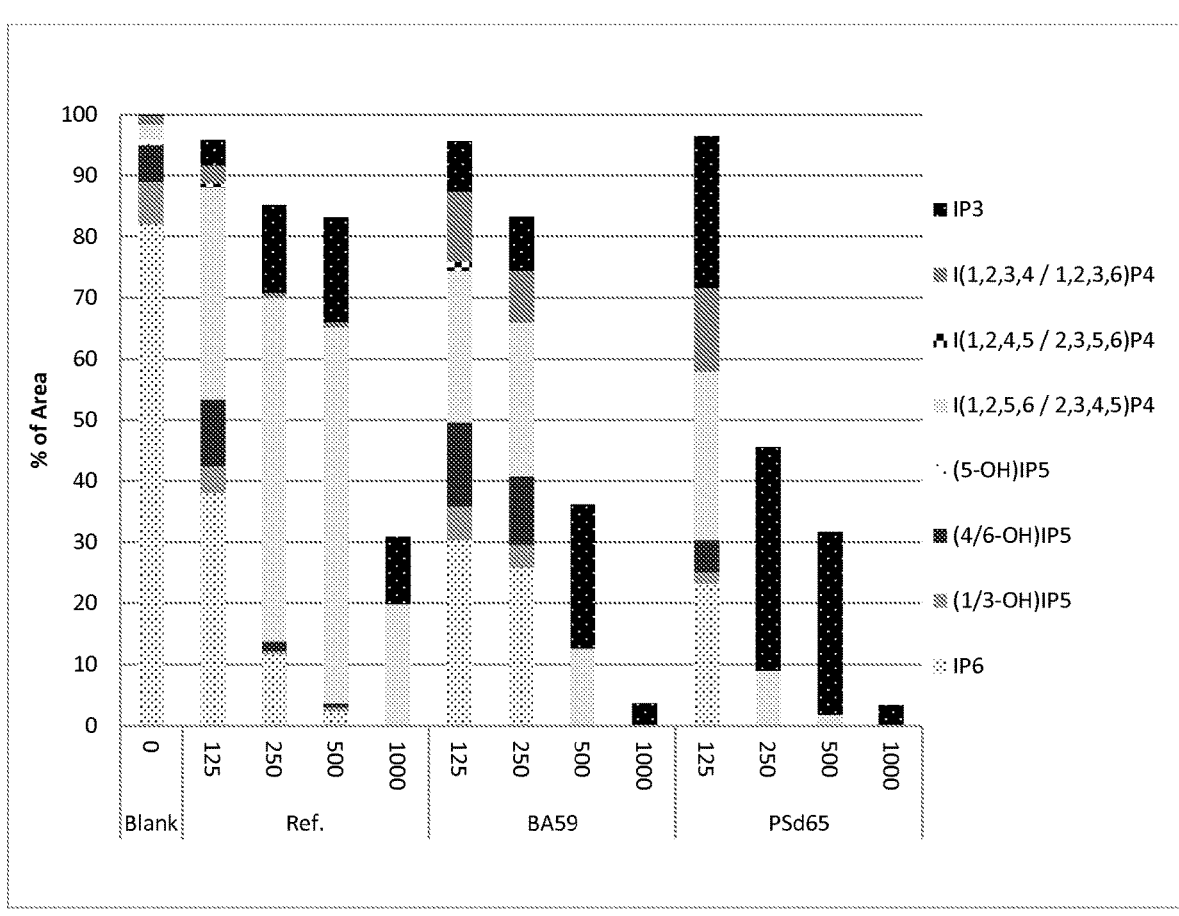
Figure 6B:
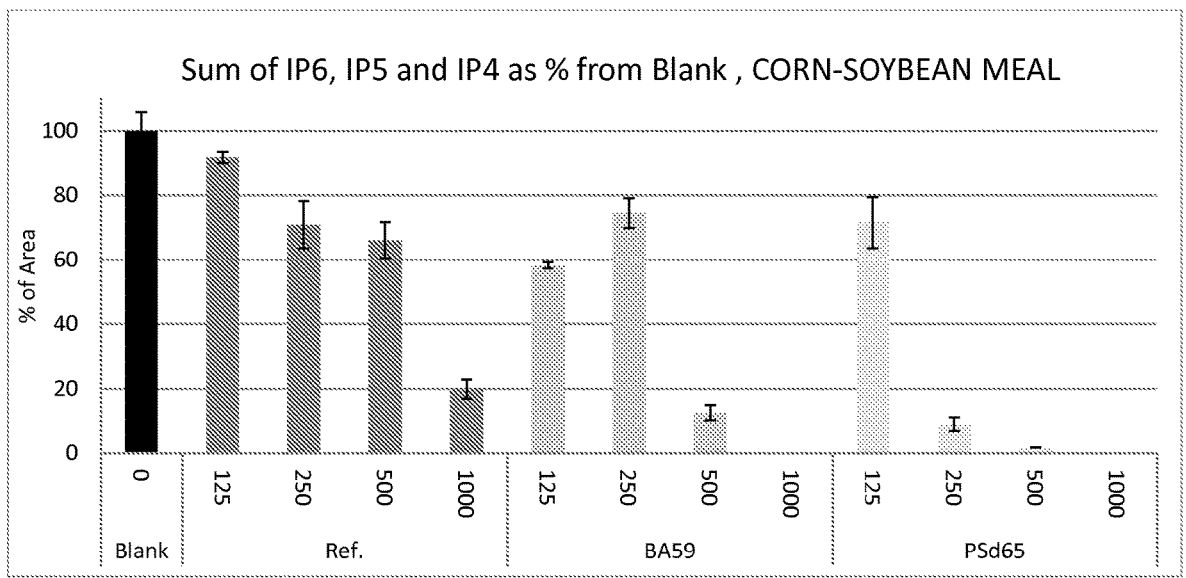

FIG. 6 shows results relative to a blank with no phytase added from GIT test using different dosages (125, 250, 500 and 1000 FTU/kg substrate) of BA59, PSd65 and *E. coli* mutant phytase in QB, produced in similar fermentation as the novel phytases (Ref.). FIG. 6A shows the amounts of IP6-IP3 inositol phosphates, including IP5 and IP4 isomers as % from blank after running the GIT assay using a mix of corn soybean meal as a substrate. FIG. 6B shows the sum of IP6-4 of the test results given in FIG. 6A (sum of IP6, IP5, IP4 as % from blank).

Figure 7A:
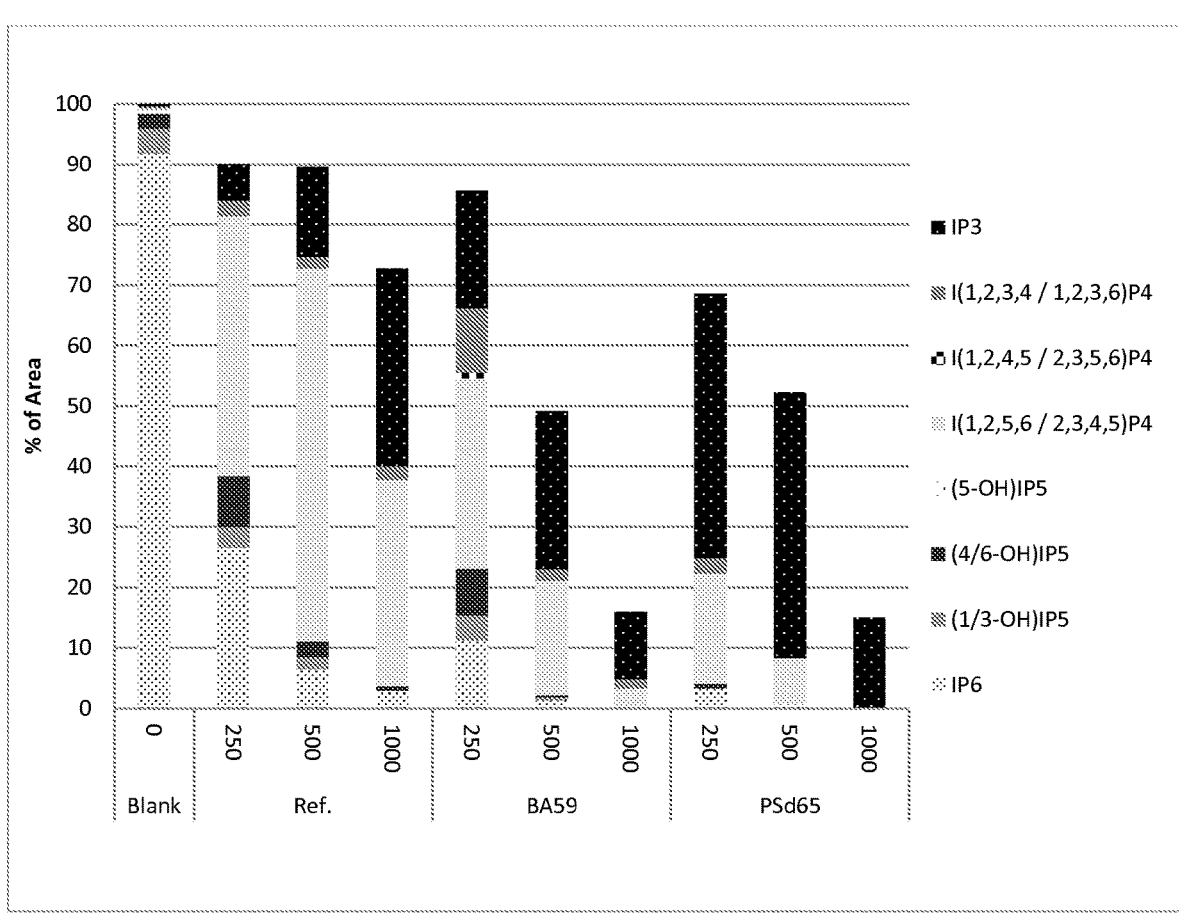
Figure 7B:
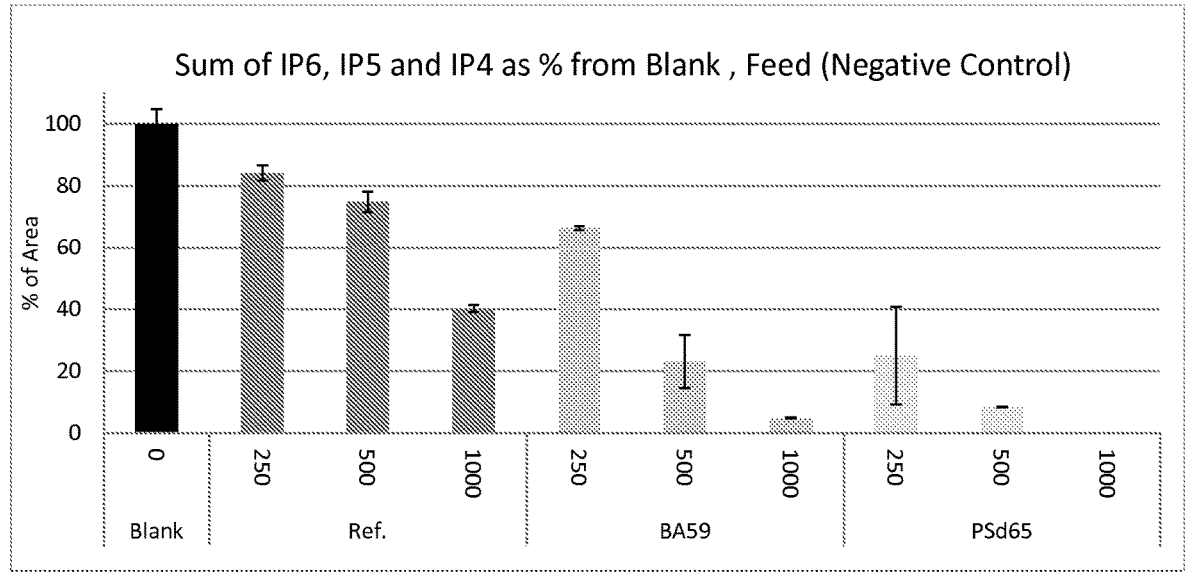

FIG. 7 shows results relative to a blank with no phytase added from GIT test using different dosages (250, 500 and 1000 FTU/kg feed) of BA59, PSd65 and *E. coli* mutant phytase in QB, produced in similar fermentation as the novel phytases (Ref.). FIG. 7A shows the IP 6-3 inositol phosphates including isomers after running the GIT assay using a corn-soybean-rape seed meal-based compound feed low in P and Ca level (negative control) as substrate. FIG. 7B shows the sum of IP6-4 of the test results given in FIG. 7A (sum of IP6, IP5, IP4).

Figure 8A:
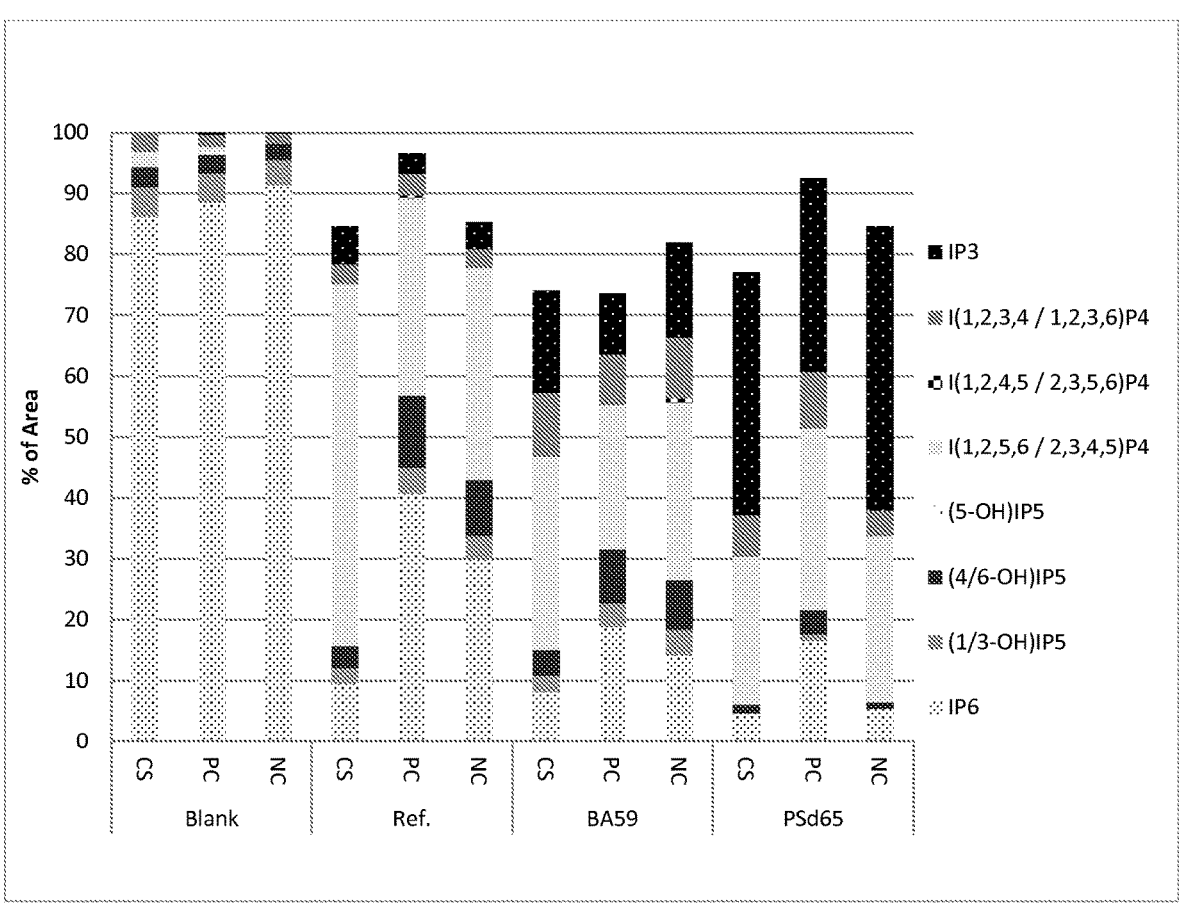
Figure 8B:
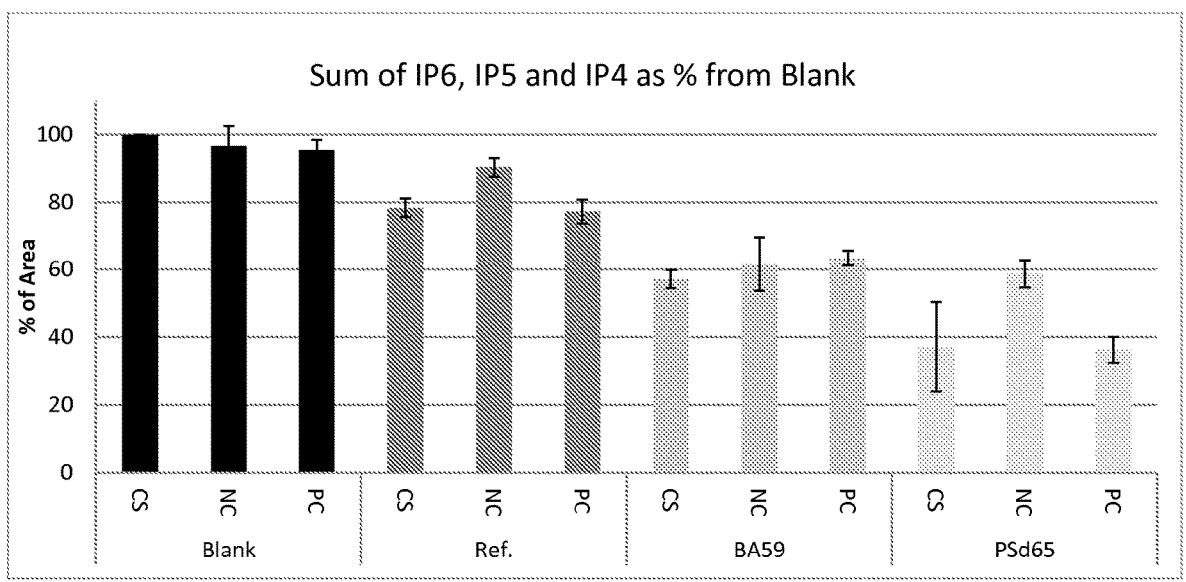

FIG. 8 shows results relative to a blank with no phytase added from GIT test using 250 FTU of BA59, PSd65 and *E. coli* mutant phytase in QB, produced in similar fermentation as the novel phytases (Ref.) per kg feed. FIG. 8A shows the amounts of IP6-3 inositol phosphates including isomers after running the GIT assay using a corn-soybean meal mix (CS), a corn-soybean-rape seed meal-based compound feed with commonly fed (PC, positive control) or reduced P and Ca level (NC, negative control) as substrates. FIG. 8B shows the sum of IP6-4 of the test results given in FIG. 8A (sum of IP6, IP5, IP4 as % from blank).

Figure 9A:
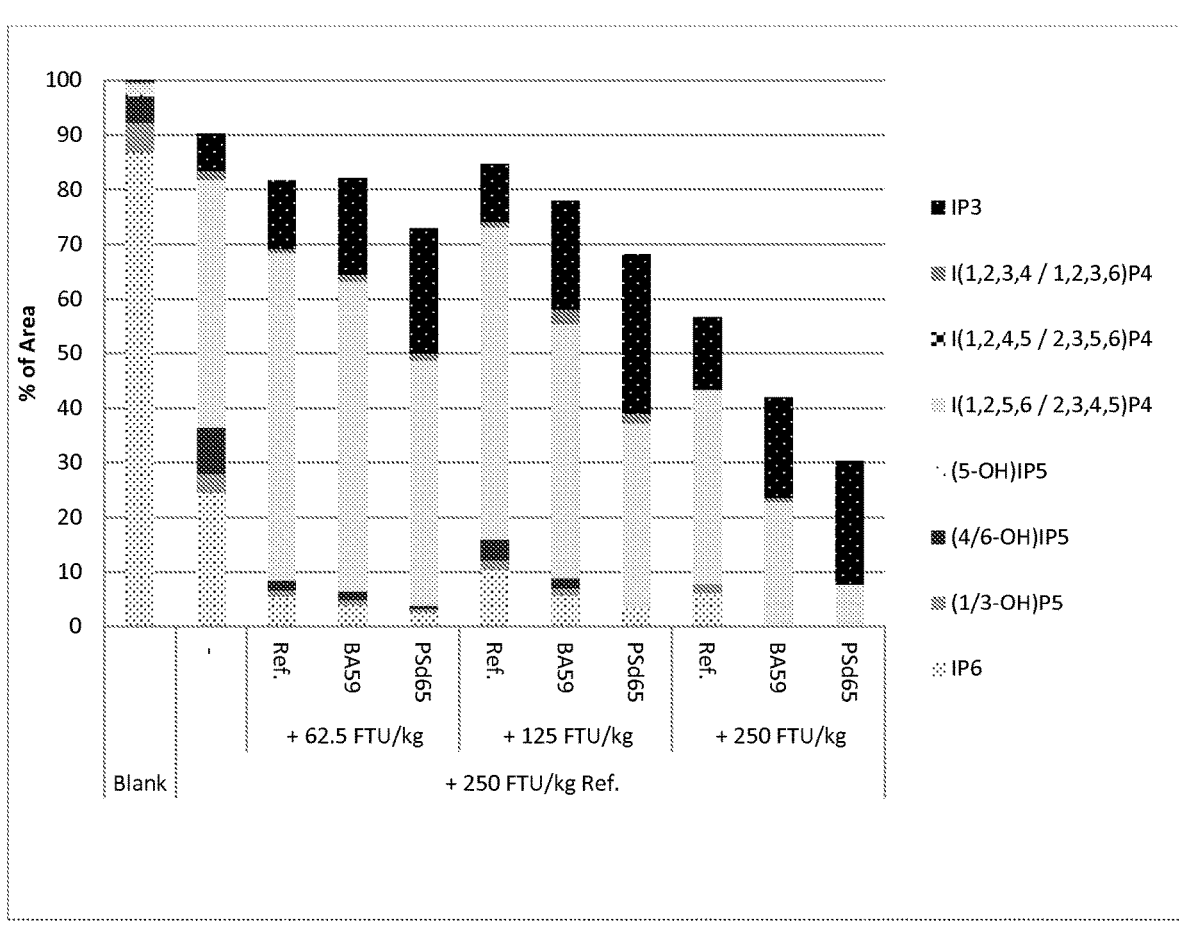
Figure 9B:
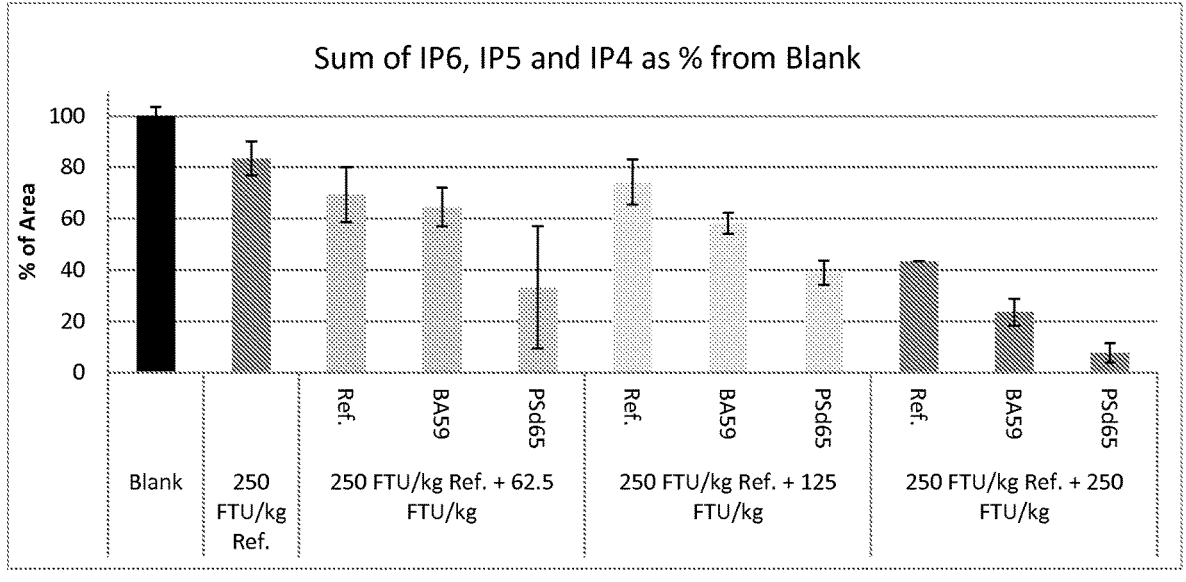

FIG. 9 shows results relative to a blank with no phytase added from GIT test when BA59 or PSd65 were used in combination with the *E. coli* mutant phytase in QB, produced in similar fermentation as the novel phytases (Ref.). 250 FTU/kg of Ref. was used and 62.5, 125 and 250 FTU/kg of BA59, PSd65 or Ref. were added. FIG. 9A. Amounts of IP 6-3 inositol phosphates including isomers after running the GIT assay using a corn-soybean meal mix-as substrate with 250 FTU/kg of Ref. alone (-) or with added increasing dosage of BA59, PSd65 or Ref. FIG. 9B shows the sum of IP6-PI4 of the test results given in FIG. 9A (sum of IP IP6, IP5 and IP4 as % from blank).

FIG. 10: Pairwise % Identities between a set of novel phytases. The deduced amino acid sequences were used in the alignments without their signal sequences. EcoliWT (Uniprot PPA_ECOLI) and ASPAW (Uniprot PPA_ASPAW) are reference sequences. SEQ ID numbers of the novel phytases are listed in Table 1.

SEQUENCE LISTINGS

SEQ ID NO: 1: BA59 amino acid sequence of the full-length phytase.

SEQ ID NO: 2: BA59 nucleotide sequence used in the expression cassette.

SEQ ID NO: 3: YE76 amino acid sequence of the full-length phytase.

SEQ ID NO: 4: YE76 nucleotide sequence used in the expression cassette.

SEQ ID NO: 5: PSd32 amino acid sequence of the full-length phytase.

SEQ ID NO: 6: PSd32 nucleotide sequence used in the expression cassette.

SEQ ID NO: 7: PSd34 amino acid sequence of the full-length phytase.

SEQ ID NO: 8: PSd34 nucleotide sequence used in the expression cassette.

SEQ ID NO: 9: PSd35 amino acid sequence of the full-length phytase.

SEQ ID NO: 10: PSd35 nucleotide sequence used in the expression cassette.

SEQ ID NO: 11: PSd65 amino acid sequence of the full-length phytase.

SEQ ID NO: 12: PSd65 nucleotide sequence used in the expression cassette.

SEQ ID NO: 13: PSd67 amino acid sequence of the full-length phytase.

SEQ ID NO: 14: PSd67 nucleotide sequence used in the expression cassette.

SEQ ID NO: 15: PSf203 amino acid sequence of the full-length phytase.

SEQ ID NO: 16: PSf203 nucleotide sequence used in the expression cassette.

SEQ ID NO: 17: PSf207 amino acid sequence of the full-length phytase.

SEQ ID NO: 18: PSf207 nucleotide sequence used in the expression cassette.

SEQ ID NO: 19: PSk235 amino acid sequence of the full-length phytase.

SEQ ID NO: 20: PSk235 nucleotide sequence used in the expression cassette.

SEQ ID NO: 21: PSk252 amino acid sequence of the full-length phytase.

SEQ ID NO: 22: PSk252 nucleotide sequence used in the expression cassette.

SEQ ID NO: 23: PSk256 amino acid sequence of the full-length phytase.

SEQ ID NO: 24: PSk256 nucleotide sequence used in the expression cassette.

SEQ ID NO: 25: PSk260 amino acid sequence of the full-length phytase.

SEQ ID NO: 26: PSk260 nucleotide sequence used in the expression cassette.

SEQ ID NO: 27: PSk267_II amino acid sequence of the full-length phytase. Starting from second methionine as compared to database entry.

SEQ ID NO: 28: PSk267_II nucleotide sequence used in the expression cassette.

SEQ ID NO: 29: PSk268_3MC amino acid sequence of the full-length phytase. Starting from third methionine as compared to database entry.

SEQ ID NO: 30: PSk268_3MC nucleotide sequence used in the expression cassette.

DETAILED DESCRIPTION

In an embodiment the polypeptide is a histidine acid phosphatase preferably from bacteria or fungi.

In an embodiment the polypeptide comprises at least one further amino acid sequence of a signal sequence, a secretory sequence, a carrier polypeptide, a tag, enzyme activity, or any combination thereof.

The polypeptide of the invention has IP4 degradation activity, IP6 degradation activity, or both IP4 and IP6 degradation activity. The polypeptide of the invention may also have IP3 and/or IP2 degradation activity.

In an embodiment the polypeptide has higher IP4 degradation activity than IP6 degradation activity at pH 3. This property makes the present phytase useful e.g. in feed applications because the phytase is able to degrade phytic acid of the feed effectively. Compared to previous IP6 phytases used in feed applications, the phytase of the present invention can take the degradation of inositol phosphate much further and release more efficiently nutrients of the feed as the lower inositol phosphates are also efficiently degraded.

In an embodiment the polypeptide has an optimal phytate hydrolysing activity at about pH 4 measured as capability to liberate inorganic phosphate under the following conditions: reaction temperature 37° C., reaction time 15 min, sodium phytate as a substrate in an initial concentration of 10 g/L.

In an embodiment the polypeptide has improved or increased IP degradation activity compared to *E. coli* mutant phytase QB, the IP degradation activity being expressed as the sum of IP6, IP5, and IP4 degradation activity. In an embodiment the degradation activity is determined using myo-inositol phosphate substrate of plant origin.

In an embodiment the composition is food or feed, and it further comprises plant material, which contains phytic acid.

In an embodiment the composition is a food additive or a feed additive further comprising at least one of: at least one trace mineral, at least one amino acid, in particular lysine, water soluble vitamin, fat soluble vitamin, prebiotics, probiotics.

In an embodiment the composition is a food additive or a feed additive complying with the requirements of Regulation (EC) No 1831/2003 of the European Parliament and of the Council of 22 Sep. 2003 on additives for use in animal nutrition.

In an embodiment the composition is in a form of a liquid composition or a solid composition such as solution, dispersion, paste, powder, granule, coated granule, tablet, cake, crystal, crystal slurry, gel, extrude, precipitate, premix optionally with other additives or pellet.

In an embodiment in the composition at least the first polypeptide or the second polypeptide is obtained by production in a recombinant host cell.

In an embodiment the recombinant host cell is selected from the group consisting of plant cells, fungal cells, filamentous fungal cells, yeasts, and bacterial cells.

"Mature polypeptide" means a polypeptide in a form following translation and any post-translational modifications, such as N-terminal processing, C-terminal truncation, glycosylation, and phosphorylation.

In an embodiment the mature amino acid sequence of BA59 comprises amino acid residues 26-439 of SEQ ID NO: 1.

In an embodiment the mature amino acid sequence of PSd65 comprises amino acid residues 24-424 of SEQ ID NO: 11.

In an embodiment the mature amino acid sequence of PSd67 comprises amino acid residues 25-403 of SEQ ID NO: 13.

In an embodiment the mature amino acid sequence of PSf203 comprises amino acid residues 16-469 of SEQ ID NO: 15.

In an embodiment the polypeptide has at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% amino acid sequence identity with the mature amino acid sequence of SEQ ID NO: 1.

In an embodiment the polypeptide has at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% amino acid sequence identity with the mature amino acid sequence of SEQ ID NO: 11.

In an embodiment the polypeptide has at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% amino acid sequence identity with the mature amino acid sequence of SEQ ID NO: 13.

In an embodiment the polypeptide has at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% amino acid sequence identity with the mature amino acid sequence of SEQ ID NO: 15.

In an embodiment the polypeptide or the phytase is a histidine acid phosphatase. In another embodiment it contains PFAM motif His_Phos_2 (PF00328). In a further embodiment the polypeptide or the phytase comprises the active site sequence motif RHGXRXP and the catalytically active HD-dipeptide at the C-terminus. Each of these structural characteristics is a common feature shared by the polypeptides according to the invention.

In an embodiment the polypeptide is obtained by recombinant production in a heterologous host cell, preferably a fungal host cell, such as *Trichoderma*.

In another embodiment the polypeptide is obtained by recombinant production in plant cells, i.e. in a transgenic plant.

The term "functional fragment" or "effective fragment" means a fragment or portion of the polypeptide, which retains about the same enzymatic function or effect.

As used herein, "isolated" means a substance in a form or environment that does not occur in nature. Non-limiting examples of isolated substances include (1) any non-naturally occurring substance, (2) any substance including any enzyme, variant, nucleic acid, protein, peptide or cofactor, that is at least partially removed from one or more or all of the naturally occurring constituents with which it is associated in nature; (3) any substance modified by the hand of man relative to that substance found in nature, such as a variant; or (4) any substance modified by increasing or decreasing the amount of the substance relative to other components with which it is naturally associated (e.g., recombinant production in a host cell; one or multiple copies of a gene encoding the substance; and use of an alternative promoter to the promoter naturally associated with the gene encoding the substance). In an embodiment a polypeptide, enzyme, variant, polynucleotide, host cell or composition of the invention is isolated.

As used herein, the term "comprising" includes the broader meanings of "including", "containing", and "comprehending", as well as the narrower expressions "consisting of" and "consisting only of".

As used herein, a "peptide" and a "polypeptide" are amino acid sequences including a plurality of consecutive polymerized amino acid residues. For purpose of this invention, peptides are molecules including up to 20 amino acid residues, and polypeptides include more than 20 amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide of any size. A protein may be an enzyme, a protein, an antibody, a membrane protein, a peptide hormone, regulator, or any other protein.

The term "polynucleotide" denotes a single-stranded or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

As used herein, "identity" means the percentage of exact matches of amino acid residues between two aligned sequences over the number of positions where there are residues present in both sequences. When one sequence has a residue with no corresponding residue in the other sequence, the alignment program allows a gap in the alignment, and that position is not counted in the denominator of the identity calculation. Identity is a value determined with the Pairwise Sequence Alignment tool EMBOSS Needle at the EMBL-EBI website (www.ebi.ac.uk/Tools/psa/emboss-_needle/). A higher sequence identity with a polypeptide having enzyme activity may mean more similar functional properties and similar structure of the polypeptide. However, a polypeptide having a lower sequence identity may also have similar properties despite the differences in the primary structure: a polypeptide having low sequence identity may be able to adopt a similar folding and conformation of the critical amino acids e.g. in the substrate binding site, in sites relevant for interaction or conformational changes, and in the active site. In one embodiment the recited sequence identity extends over the full length of the sequence.

As used herein, "host cell" means any cell type that is susceptible to transformation, transfection, transduction, mating, crossing or the like with a nucleic acid construct or expression vector comprising a polynucleotide. The term "host cell" encompasses any progeny that is not identical due to mutations that occur during replication. Non-limiting examples of a host cell are plant cells, fungal cells, filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus, Chrysosporium, Myceliophthora* and *Humicola*; more preferably from the group consisting of Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium*, and *Scedosporium*; more preferably from the group consisting of *Trichoderma reesei (Hypocrea jecorina), T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chryso-*

*genum*, and *Scedosporium apiospermum*, and *Aspergillus niger, Aspergillus awamori, Aspergillus oryzae, Chrysosporium lucknowense, Myceliophthora thermophila, Humicola insolens*, and *Humicola grisea*, most preferably *Trichoderma reesei*. Non-limiting examples of a host cell are bacterial cells, preferably gram-positive Bacilli (e.g. *Bacillus subtilis, B. licheniformis, B. megaterium, B. amyloliquefaciens, B. pumilus*), gram-negative bacteria (e.g. *Escherichia coli*), actinomycetales (e.g. *Streptomyces* sp.) and yeasts (e.g. *Saccharomyces cerevisiae, Pichia pastoris, Yarrowia lipolytica*).

In an embodiment the host cell is a fungal cell, preferably a filamentous fungal cell, such as *Trichoderma* or *Trichoderma reesei*. In an embodiment the host cell is a bacterial cell, preferably a gram-positive *Bacillus* cell, such as *B. subtilis, B. licheniformis, B. megaterium, B. amyloliquefaciens, B. pumilus.*

As used herein, "expression" includes any step involved in the production of a polypeptide in a host cell including, but not limited to, transcription, translation, post-translational modification, and secretion. Expression may be followed by harvesting, i.e. recovering, the host cells or the expressed product.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, carrier and the like. Expression vectors are generally derived from plasmid or viral DNA, or may contain elements of both. The expression vector may be any expression vector that is conveniently subjected to recombinant DNA procedures, and the choice of vector will often depend on the host cell into which the vector is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. In an embodiment the present vector is an expression vector.

The term "recombinant" or "recombinantly produced" used herein in connection with production of a polypeptide or protein is defined according to the standard definition in the art.

The term "obtained from" and "obtainable" as used herein in connection with a specific microbial source means that the polynucleotide is expressed by the specific source (homologous expression), or by a cell in which a gene from the source has been inserted (heterologous expression).

The term "enzyme composition" means either a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species or the fermentation product of a microorganism which acts as a host cell for production of a recombinant polypeptide, but which microorganism simultaneously produces other enzymes. An enzyme composition may be a dry product, such as powder, pellet, extrude or granule.

In another embodiment the polypeptide is formulated in the composition in at least partially dissolved form, in dilute or compressed solid or liquid form including but not limited to solutions, suspensions, emulsions, semi-solids, solids, pastes, pellets, cakes, gels, tablets, films or coatings having certain targeted properties like for example controlled rheology, viscosity or enzyme release.

In an embodiment of the invention is provided a granule comprising the present polypeptide, or composition. The granule is optionally coated by a coating layer which encapsulates the core to form a substantially continuous layer and controls its release.

The coating layer is preferably food grade or feed grade material suitable for use in food and/or feed.

The term "operably linked", when referring to DNA segments, denotes that the segments are arranged so that they function in concert for their intended purposes, e.g. transcription initiates in the promoter and proceeds through the coding segment to the terminator.

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" or "signal sequence" denotes a DNA sequence that encodes a polypeptide (a "secretory peptide") that, as a component of a larger polypeptide, directs the larger polypeptide through a secretory pathway of a host cell in which it is produced. The secretory signal sequence can be native or it can be replaced with secretory signal sequence and carrier sequence from another source. Depending on the host cell, the larger peptide may be cleaved to remove the secretory peptide during transit through the secretory pathway.

The term "core region" or "catalytic domain" denotes a domain of an enzyme, which may or may not have been modified or altered, but which has retained at least part of its original activity.

Efficient amount means an amount, which is sufficient to degrade phytic acid or lower IP forms in the selected application.

The term "stability" includes storage stability and stability during use, e.g. in conditions of feed production or in the animal digestive track and reflects the stability of the polypeptide according to the invention as a function of time, e.g. how much activity is retained when the polypeptide is kept in solution, in feed or used in application. The stability is influenced by many factors, e.g. pH, temperature, proteases, etc. The phytase stability may be measured using the 'activity assay' as described in examples.

In an embodiment phytase activity is determined with the PPU assay, FTU assay, plate assay or 4-MUP assay as described in Example 2.

"Animal" refers in the present application to any animal. Examples of animals are monogastric (non-ruminant) animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broilers), chicks, layer hens (referred to herein as layers); fish; horses (including but not limited to hotbloods, coldbloods and warm bloods). In an embodiment the animal is any non-human animal.

"Feed", such as animal feed, refers to any compound, preparation, or mixture suitable for, or intended for intake by an animal. Animal feed for a monogastric animal typically comprises concentrates including any feed ingredients like but not limited to corn, wheat, soy bean meal as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Without limiting the scope and interpretation of the patent claims, certain technical effects of one or more of the aspects or embodiments disclosed herein are listed in the following: A technical effect is degradation or modification of phytic acid, in particular lower inositol phosphates.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed aspects and embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

In an embodiment the polypeptide or the nucleic acid is a non-naturally occurring polypeptide or nucleic acid, where its sequence is not 100% identical with the corresponding SEQ ID NO, which is used to identify it. In an embodiment the nucleic acid is codon-optimized for production in the selected host cell for recombinant production. A polypeptide produced with such a codon-optimized nucleic acid provides increased production yield of the polypeptide.

In an embodiment at least one component of the compositions of the invention has a different chemical, structural or physical characteristic compared to the corresponding natural component from which the at least one component is derived from. In an embodiment said characteristic is at least one of uniform size, homogeneous dispersion, different isoform, different codon degeneracy, different post-translational modification, different methylation, different tertiary or quaternary structure, different enzyme activity, different affinity, different binding activity, and different immunogenicity.

The following clauses are described:

Clause 1. A composition comprising a polypeptide and at least one feedingstuff or additive selected from stabiliser, preservative, mineral and nutrient, wherein the polypeptide is selected from the group consisting of:

a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and wherein the polypeptide is an isolated, recombinant or synthetic polypeptide.

Clause 2. The composition of clause 1 wherein the polypeptide has higher IP4 degradation activity than IP6 degradation activity at pH 3.

Clause 3. A composition comprising at least two polypeptides having phytase activity and at least one additive, wherein:

the first polypeptide has phytase activity and is selected from an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and the second polypeptide has phytase activity, does not have an identical amino acid sequence with the first polypeptide, and is selected from *E. coli* mutant phytase QB, an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15).

Clause 4. The composition of clauses 1-3, wherein the composition is a food additive or a feed additive further comprising at least one of: minerals, amino acids, prebiotics, probiotics.

Clause 5. The composition of clauses 1-4 in a form of a liquid composition or a solid composition such as solution, dispersion, paste, powder, granule, coated granule, tablet, cake, crystal, crystal slurry, gel, extrude or pellet.

Clause 6. The composition of clauses 1-5, wherein at least one of the first polypeptide and the second polypeptide is obtained by production in a recombinant host cell.

Clause 7. An animal feed comprising the composition of clauses 1-6, and at least one protein source of plant origin, and a. Optionally at least one further enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate, or a combination thereof.

Clause 8. A feed supplement comprising the composition of clauses 1-6; and a. Optionally at least one further enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate, minerals, amino acids, prebiotics, probiotics. or a combination thereof.

Clause 9. A use of a polypeptide selected from the group consisting of:

a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15);

for degrading phytic acid.

Clause 10. A method of producing phytase in a recombinant host cell comprising a. providing a polynucleotide comprising genetic elements for producing a phytase comprising an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. expressing the polynucleotide in a recombinant host cell;

wherein the phytase is capable of releasing phosphate from phytic acid.

Clause 11. A recombinant host cell comprising genetic elements for producing at least one polypeptide selected from the group consisting of:

a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15).

Clause 12. The recombinant host cell of clause 11, wherein the recombinant host cell is selected from the group consisting of plant cells, fungal cells, filamentous fungal cells, yeasts, and bacterial cells.

Clause 13. A use of the polypeptide selected from the group consisting of:

a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15);

in animal feed, in animal feed additives, in preparation of a composition for use in animal feed, and/or for improving digestibility of feed.

Clause 14. A use of the polypeptide wherein the polypeptide is selected from the group consisting of:

a. an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15); and b. an amino acid sequence comprising a functional fragment of amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15);

in food, in food additives, in preparation of a composition for use in food, and/or for improving digestibility of food.

EXAMPLES

The following examples are provided to illustrate various aspects of the present invention. They are not intended to limit the invention, which is defined by the accompanying claims.

Example 1. Sequence Search to Identify Novel Candidate Phytases

In order to identify novel phytase candidates a protein family analysis was conducted. The histidine acid phosphatase group (HAP protein family) was chosen for search.

To start the protein family analysis of histidine acid phosphatases, all proteins belonging to the protein family were collected. Proteins were retrieved by homology-based BLAST searches and by protein motif search. The known phytase sequences from *Aspergillus awamori* (Uniprot PHYA_ASPAW) and *Escherichia coli* (Uniprot PPA_ECOLI) were used as queries in the BLAST search.

The BLAST searches were conducted against several sequence databases, to get maximum coverage of the available sequences. The following databases were queried using command line BLAST: NCBI protein databases (nr, pataa, tsa_nr, env_nr), NCBI nucleotide databases (nt, patnt, env_nt, tsa_nt, nt, other_genomic), Uniprot protein database (including both SwissProt and TrEMBL), fungal genomes downloaded from JGI (https://genome.jgi.doe.gov/), proprietary genomes of fungal and bacterial species, patent sequence data via SequenceBase i.e. protein sequences from Thomson Reuters GENESEQ™, USGENE®, WOGENE.

The BLAST searches were conducted using a shell script in an unix environment. The script goes through the databases and for each database conducts a batch BLAST search using both query protein sequences simultaneously. E-value threshold of 1e-30 was used. The BLAST was requested to return 10000 best hits for each query. Otherwise default parameters were used. The script then retrieved the DNA/AA sequence of matching hits. For BLAST hits from nucleotide databases a specially built script was used to process the xml-format BLAST output and extract the matching portion as an amino acid sequence. In total 14998 sequences were retrieved using the homology-based BLAST search.

Retrieval of sequences based on protein family motif was done via Uniprot (release 2017-02). The Uniprot database has annotated all protein motifs to all sequences in Uniprot. All sequences matching the histidine acid phosphatase protein family PFAM-motif PF00328 were retrieved from Uniprot. 11924 sequences were retrieved using this method.

The same identical sequence may be retrieved several times using the above procedure. To avoid duplicates, a clustering approach was used to identify and remove identical amino acid sequences. CD-HIT (http://weizhongli-lab.org/cd-hit/), a program for clustering and comparing protein or nucleotide sequences, was used to do the clustering. After the clustering procedure 8130 unique sequences remained.

After retrieval of all members of the histidine acid phosphatase protein family, a phylogenetic tree was constructed to get an understanding of the diversity and sub-families in the histidine acid phosphatase family. The construction of the phylogenetic tree consisted of clustering of sequences to remove redundancy, followed by multiple sequence alignment and building of the phylogenetic tree.

The protein sequences were clustered before the multiple sequence alignment and phylogenetic tree construction. This was done to remove the redundancy. To get an even coverage of the sequence space, the sequences were clustered to 95% identity using the CD-HIT clustering program. In the end 2309 sequences remained. Each of these 2309 sequences is a representative of itself or a set of sequences that are above 95% identical to the chosen representative.

Figure 2:
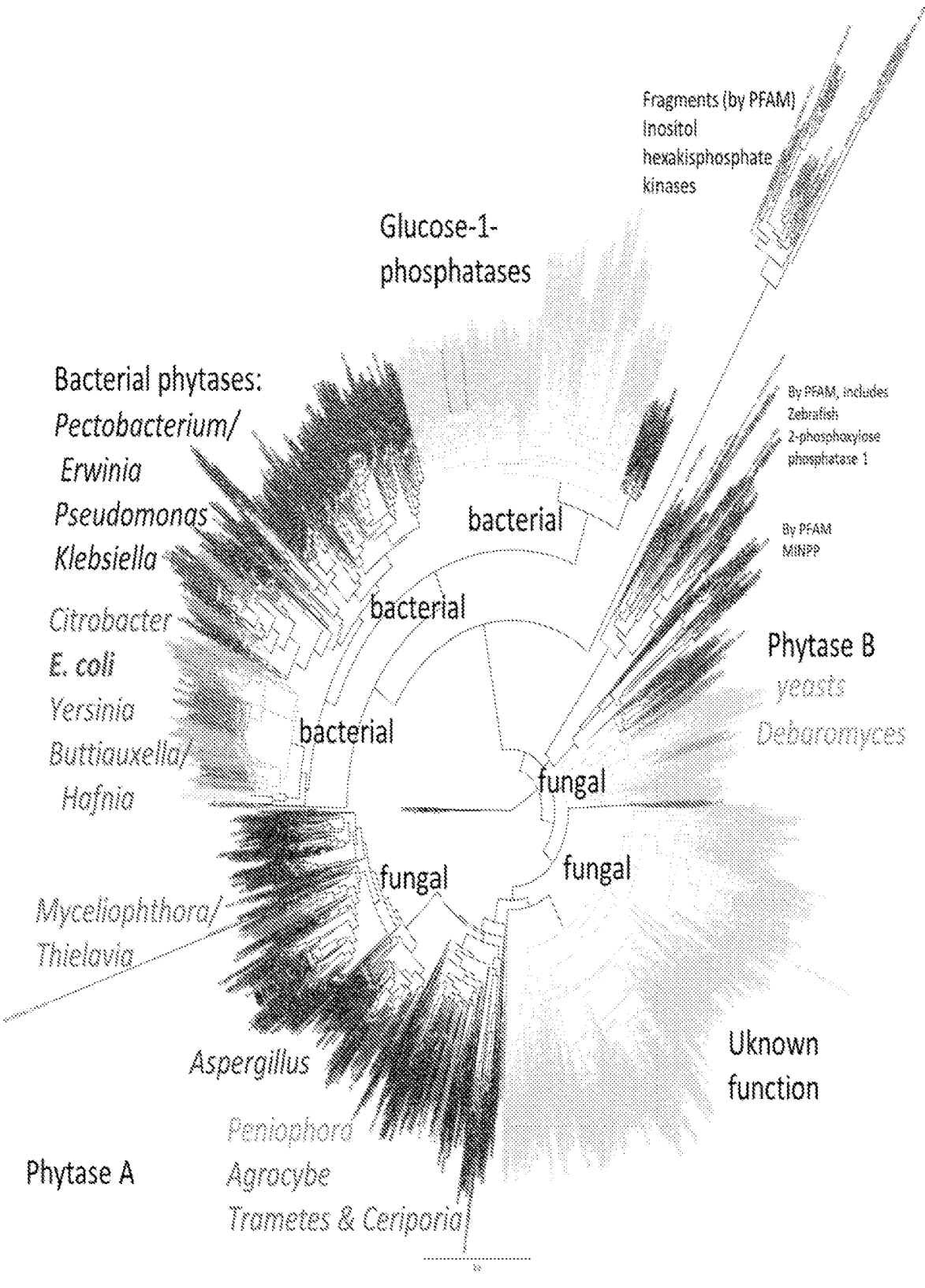
FIG. 2 shows a phylogenetic tree of the candidate polypeptides.

The 2309 selected candidates were aligned using MAFFT (https://mafft.cbrc.jp/alignment/software/), a multiple sequence alignment program. A phylogenetic tree was built based on the multiple sequence alignment using FastTree (http://www.microbesonline.org/fasttree/) algorithm (FIG. 2). FastTree infers approximately-maximum-likelihood phylogenetic trees from alignments of nucleotide or protein sequences.

The phylogenetic tree was annotated based on the descriptions and annotations of the sequences included in the tree. Besides phytases the tree contains glucose-1-phophatases, inositol hexakisphosphate and diphosphoinositol-pentakisphosphate kinases, acid phosphatases (including lysophosphatidic acid phosphatase and prostatic acid phosphatases), multiple inositol-polyphosphate phosphatases and a large group of uncharacterised proteins some of which are tentatively annotates as phosphoglycerate mutase-like proteins.

About third of the tree (759 sequences) is within a major branch containing the known bacterial phytases and the known bacterial glucose-1-phosphatases. The branch contains a lot of uncharacterised sequences with putative annotations ranging between phytase, glucose-1-phosphatase, and phosphoanhydride phosphohydrolase.

About two thirds of the tree (1373 sequences) is within a major branch containing the known fungal phytases and fungal acid phosphatases, and the large branch of fungal uncharacterized sequences tentatively annotated as phosphoglycerate mutase-like. Within this larger branch the branch containing the fungal phytase A type proteins has 553 sequences, and the branch containing yeast phosphatases and fungal phytase B type proteins has 205 sequences. The latter contains sequences mainly retrieved by the PFAM domain search, as the homology to the fungal phytase used as BLAST query (*Aspergillus* PhyA) is quite low.

Figure 3:
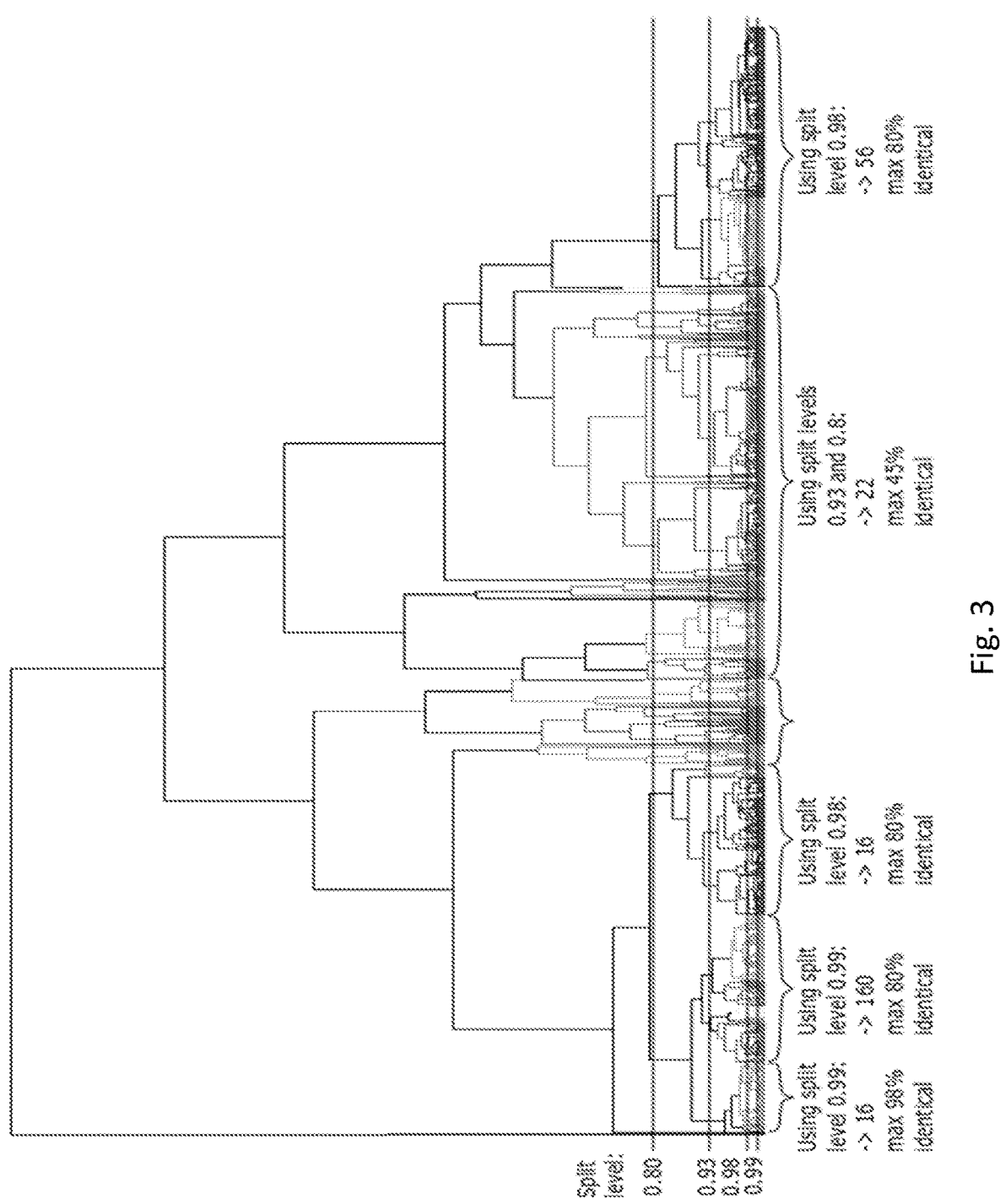
FIG. 3 shows a split phylogenetic tree.
Figure 4A:
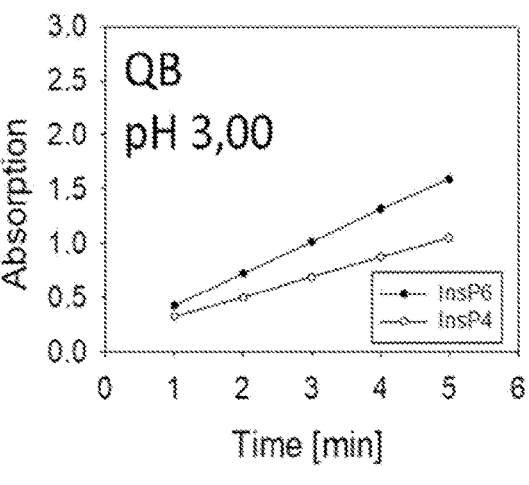
FIGS. 4A and 4B, mutant *E. coli* phytase (Quantum Blue product, QB); 4C and 4D BA59; 4E and 4F.
Figure 4B:
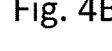
Figure 4C:
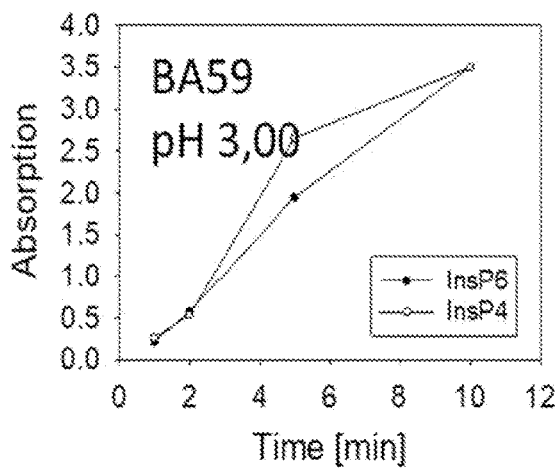
FIG. 4 shows the efficiency (change of absorption in reaction) of selected phytases on degradation of IP6 and IP4 at pH 3 and pH 5.
Figure 4D:
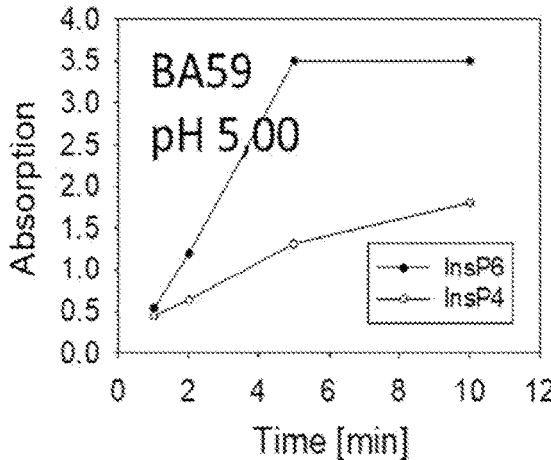
Figure 4E:
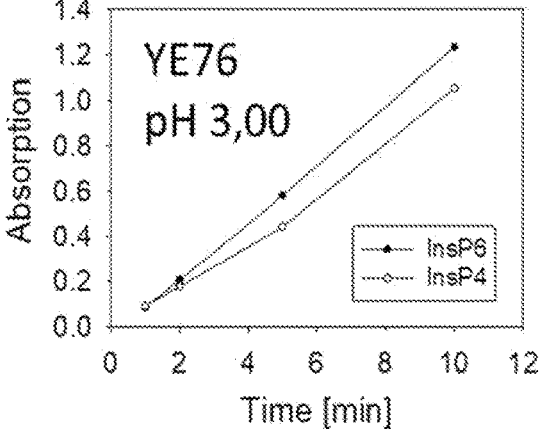
Figure 4F:
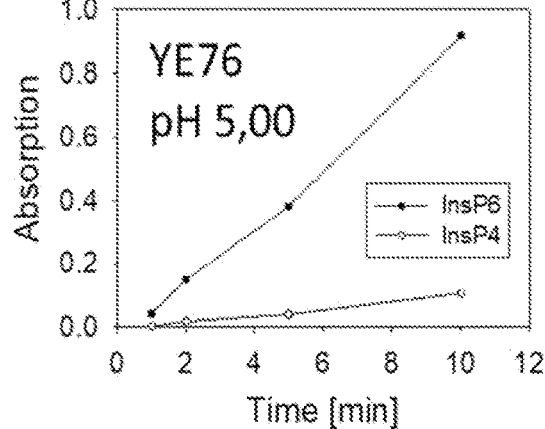
Figure 4G:
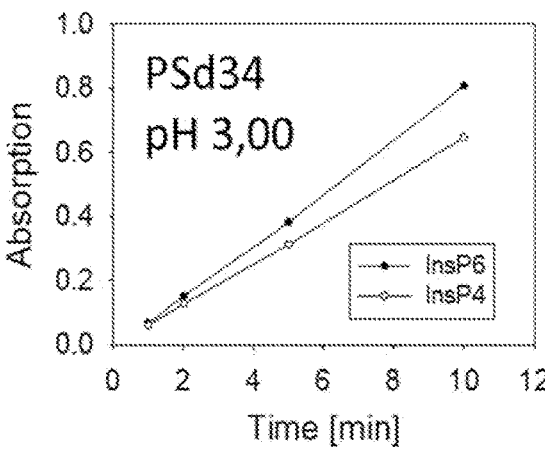
Figure 4H:
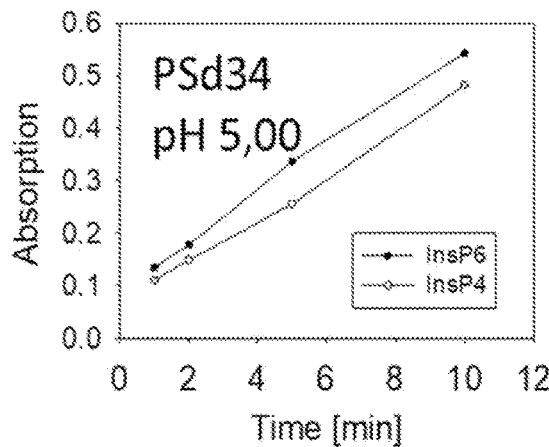
Figure 4I:
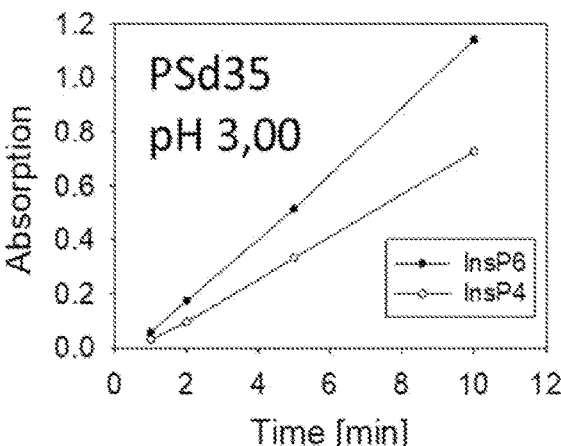
Figure 4J:
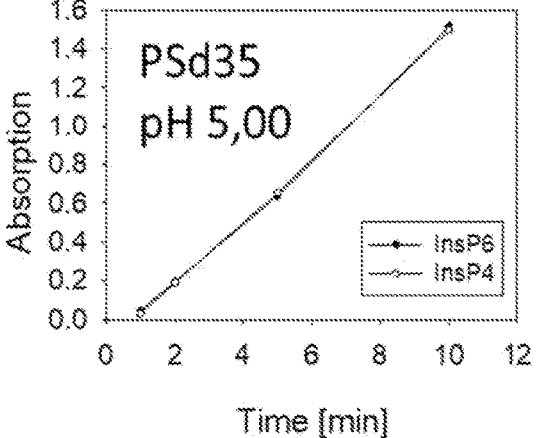
Figure 4K:
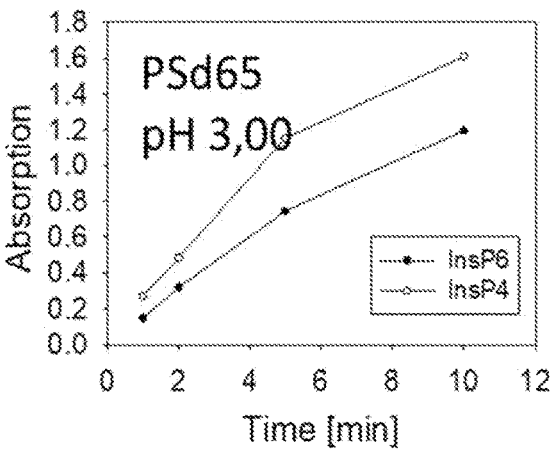
Figure 4L:
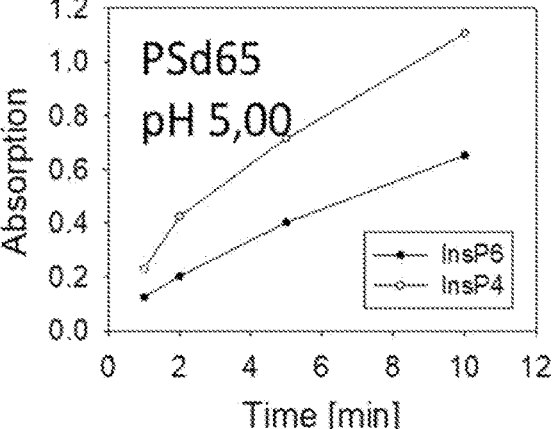
Figure 4M:
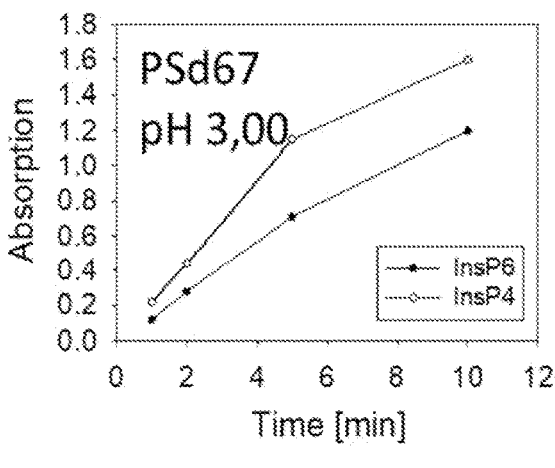
Figure 4N:
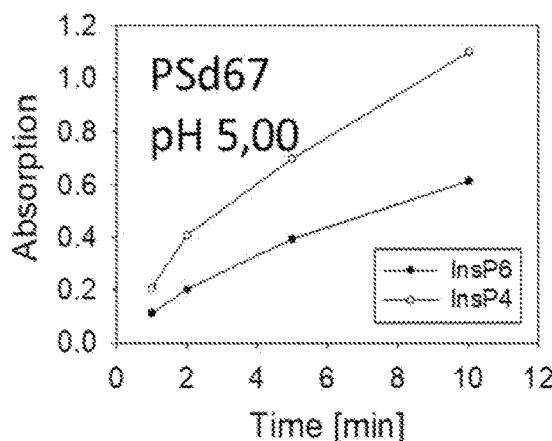
Figure 4O:
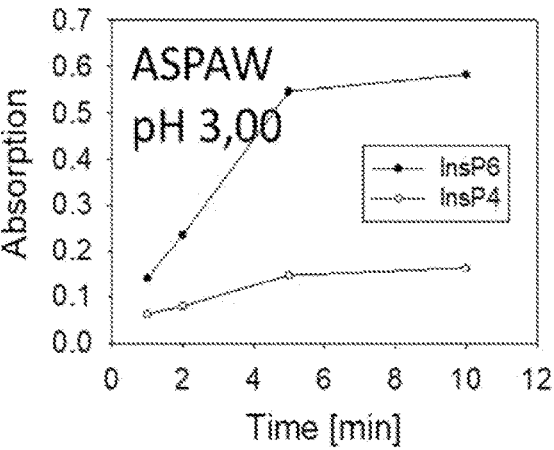
Figure 4P:
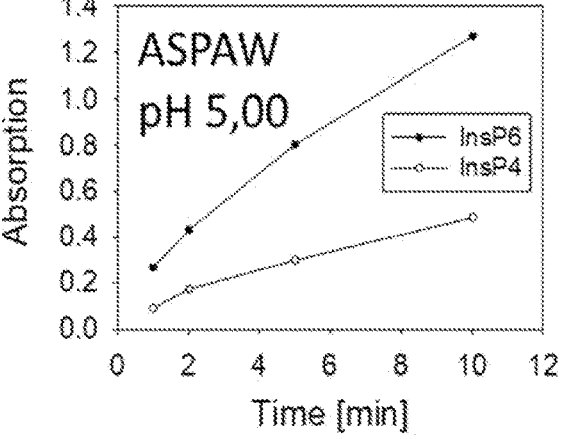
Figure 4Q:
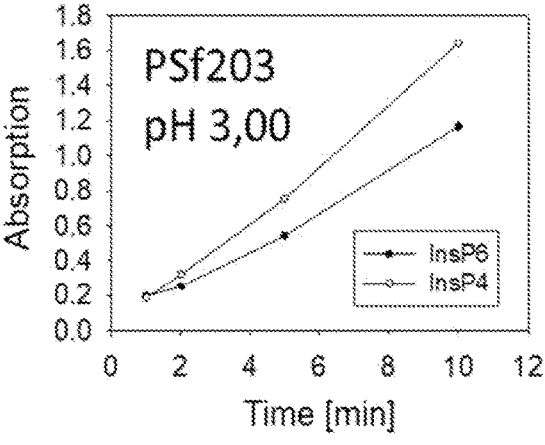
Figure 4R:
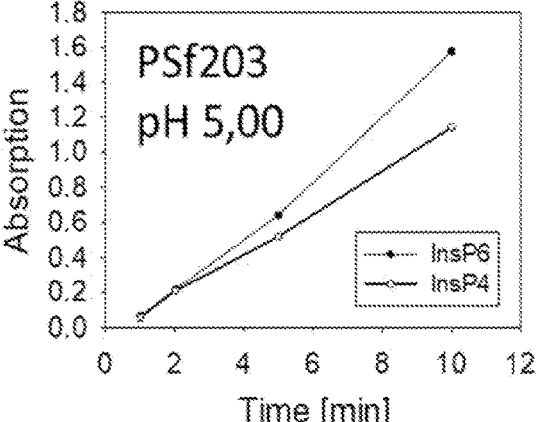
Figure 4S:
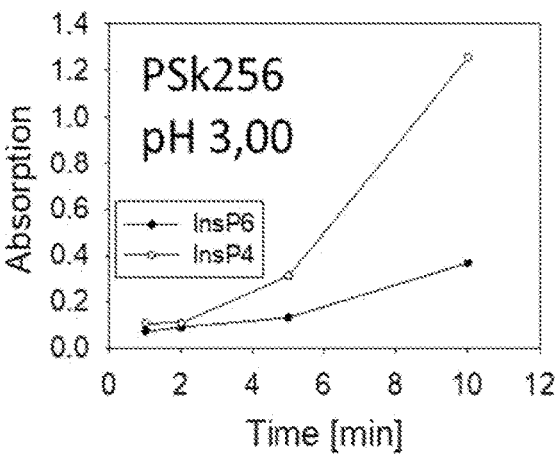
Figure 4T:
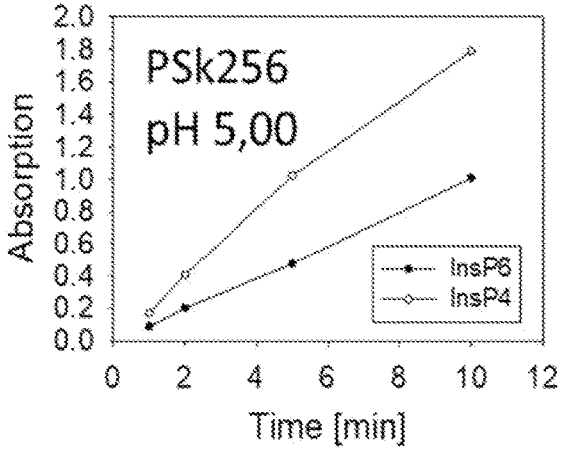
Figure 4U:
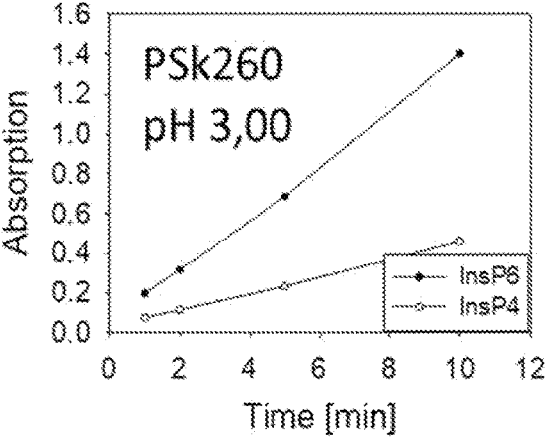
Figure 4V:
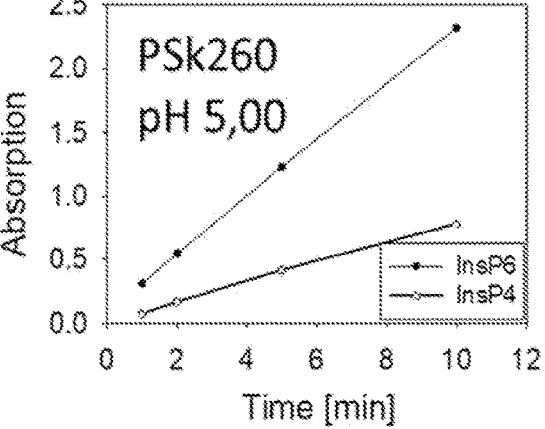
Figure 4W:
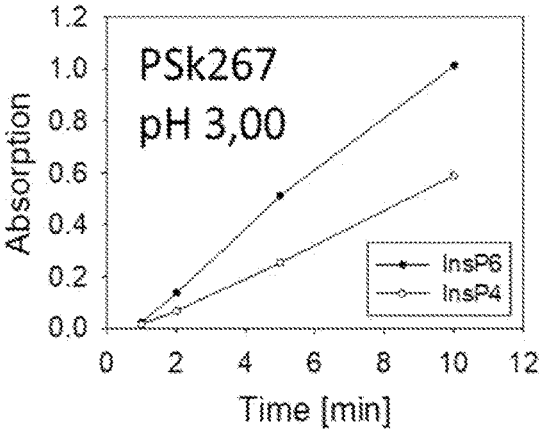
Figure 4X:
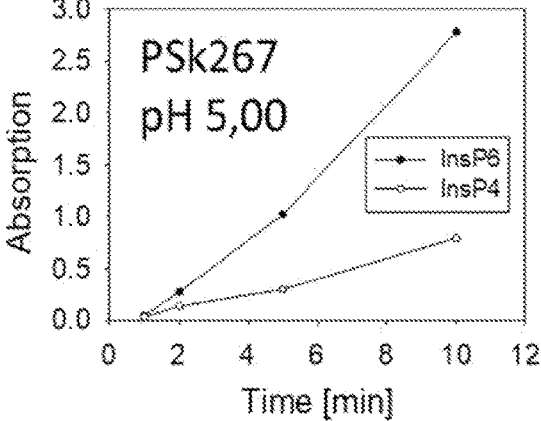

Candidate sequences for expression were selected from both the bacterial and fungal branches. The selection strategy varied between different parts of the phylogenetic tree. More candidates were picked from branches containing sequences with verified function as a phytase, and very few sequences from branches containing only sequences with unknown function. To aid the manual selection process, the phylogenetic tree was split into groups by cutting the tree at various depths. A suitable cut depth was selected for each major branch, resulting in a list of disjoint small subtrees (FIG. 3). A single representative sequence was selected from each disjoint subtree.

In the subtree nearest to the known phytases 16 novel sequences were selected. From the next branches altogether 160 candidates were selected such that they are at most 80% identical to each other. Finally, 16 candidates at most 80% identical to each other were selected from the branch containing glucose-1-phosphatases.

In the fungal branch, 56 sequences (at most 80% identical to each other) were selected from the subtree containing Phytase A sequences from fungi. The less promising portion of the fungal subtree was cut at a higher level, resulting at 22 disjoint subtrees and thus 22 candidates. The mature amino acid sequences of these 22 candidates were at most 45% identical to each other.

Example 2. Activity Assay Methods Used

Plate Assay

In the semi-quantitative phytase plate assay, the turbid phytate becomes clear when it is hydrolysed. Thus, the phytase activity is visualized by the clearing around the applied sample. This was, in the case of *E. coli* cell lysate.

In cases when the plate assay was used for selecting the *Trichoderma* or *Bacillus* transformants, the sample used was the culture supernatant.

The plates for the assay were prepared by adding 1.3% sodium phytate, 4% malt extract, 6.5% yeast extract, 1% enzymatically hydrolysed casein, 0.01 M sodium-acetate (1 M solution, pH 4.5 was used), and 0.05 M $CaCl_2$) (1 M solution was used) to 50% Mineral salt Solution (4 g $KH_2PO_4$, 6 g $Na_2HPO_4$, 0.2 g $FeSO_4*7 H_2O$, 1 mg $CaCl_2$), 1 g $(NH_4)_2SO_4$, ad. 1 L tap water). Deionized water was used and 4% Agar was added. The prepared medium was autoclaved (15 min at 121° C.) and poured on petri dishes. For application of the enzyme sample, small holes were stitched out of the hardened agar plates and the sample was pipetted into the hole. For *E. coli* cell lysates and *Bacillus* culture supernatants, 20 μL of the lysate was used, and plates were incubated for 18 h at 37° C. The result was documented by taking photographs of the plates.

PPU Assay

Phytase acts on phytate (inositol hexaphosphate) to release inorganic phosphate. The phytase activity is determined by analysing the amount of released inorganic phosphate from the substrate. The PPU analysis method was used in screening and characterisation of the novel phytases produced in *E. coli*, *Bacillus pumilus* and *T. reesei*. In this method one activity unit (named as PPU) is the amount of enzyme, which liberates 1 μmol of inorganic phosphate in one minute under the following conditions: pH 5.0, reaction temperature 37° C., reaction time 15 min, sodium phytate ($C_6H_6O_{24}P_6Na_{12}$, Sigma P0109) as a substrate in a concentration of 10 g/L. The analysis is based on the colour formed by the reduction of a phosphomolybdate complex.

In the assay the enzyme samples are first diluted in a reaction buffer (0.2 M citrate buffer, pH 5.0). 1 ml of the enzyme solution is used in the analysis. 1 ml of substrate is added to the enzyme sample and the mixture is incubated for exactly 15 min at 37° C. The reaction is stopped by adding 2.0 ml of 15% (w/v) TCA solution after which the reaction tube is mixed and let cool to room temperature. After the hydrolysis reaction mixture has cooled, it is diluted 1:10 to test tubes by pipetting 0.4 ml of sample and adding 3.6 ml of water. 4.0 ml of freshly made-up colour reagent consisting of 3 volumes of 1 M sulphuric acid, 1 volume of ammonium molybdate (25 g of ammoniummmolybdate $(NH_4)_6Mo_7O_{24}\cdot4H_2O$, Merck 1182, in 100 mL of water) and 1 volume of 10% ascorbic acid in water) is added and the contents of the tube are mixed. The tubes are incubated at 50° C. for 20 min after which the absorption is measured at 820 nm. For the enzyme blank value enzyme sample are added after quenching with trichloroacetic acid.

The amount of liberated phosphate is determined via a calibration curve of the color reaction with a phosphate solution of known concentration.

For analysis of the phytase activity at pH 3, the PPU assay was modified as follows: instead of using 0.2 M citrate reaction buffer, pH 5.0, 0.2 M glycine-HCl, pH 3.0 was used.

4-MUP Assay

The artificial substrate 4-methylumbelliferyl-phosphate (4-MUP) was used in the direct kinetic measurement of phytase activity in screening the phytases produced in *E. coli*. In the assay, a fluorescence signal is generated. The signal intensity changes during the enzymatic reaction. The slope of the signal change is determined and given relative to a standard value.

0.25 mM 4-MUP, solved in 50 mM sodium citrate buffer (pH 5.00) is used as a substrate in the assay. The slopes are analysed from different dilutions of the sample. 50 μL of sample, blank and standard solution are pipetted to wells of a 96-well microtiter plate after which the plate is transferred to microplate reader, e.g. BMG POLARStar Omega or BMG CLARIOstar. The reaction is started on the plate reader by pipetting (using the syringe of the plate reader) 200 μL of substrate solution to each well. The enzyme reaction is subsequently monitored (excitation 360 nm, emission 450 nm, interval time 1.00 s). Samples are analysed as triplicates. Standards and blank are included in wells as triplicates.

FTU Assay

In FTU assay inorganic phosphate released from sodium phytate substrate by the hydrolytic enzymatic action of phytase is detected. Colour formation, which is measured spectrophotometrically, is the result of molybdate and vanadate ions complexing with inorganic phosphate. One phytase unit (FTU) is the quantity of enzyme that liberates 1 μmol of inorganic phosphate per minute from sodium phytate at 37° C., pH 5.50, using 60 min incubation time. When the activity analysis is performed at pH 3 the pH of the buffer and substrate are adjusted to pH 3.0 instead of pH 5.5 (see below).

In the assay, 2.0 ml of 1% sodium phytate substrate (LabChem EE05501, in 250 mM sodium acetate buffer, pH 5.5 and including 1 mM $CaCl_2\cdot2H_2O$ and 0.01% Tween 20) is pipetted to plastic centrifuge tubes. The substrate tubes are pre-incubated for 5-10 minutes at 37° C. after which 1.0 ml of diluted enzyme sample is added. After exactly 60 min incubation 2.0 ml of colour stop solution is added and tube contents are mixed by vortexing. Enzyme blanks are prepared like the sample but the colour stop solution is added to the substrate tubes prior to addition of the diluted enzyme sample. For colour reaction the tubes are incubated for 20 min at room temperature after which they are centrifuged at 4000 rpm for 10 minutes. The sample absorbance is measured against an enzyme blank at 415 nm. For the activity units, a potassium phosphate standard curve (pH 5.50) is prepared (dried $KH_2PO_4$, Merck 1.04873.1 is used for the standard; drying at 105° C. for 2 hours before weighting).

The stop solution is prepared as follows (preparation just prior to use): for 100 ml of colour stop solution, 25 ml of stock ammonium heptamolybdate (20 g of $(NH_4)_6Mo_7O_{24}\cdot4H_2O$, Merck 1182 in 180 ml of water, add 2 ml of ammonium hydroxide ($NH_4OH$, Sigma-Aldrich 221228 28-30%), final volume 200 ml) is mixed with 25 ml of stock ammonium vanadate solution (0.47 g of ammonium vanadate (NH4VO3, Riedel de Haen 31153) in 160 ml of water; once the completely dissolved, 4 ml of 22.75% nitric acid solution is added, final volume 200 ml). Then, 16.5 ml of 22.75% nitric acid solution ($HNO_3$, Merck 1.00456) is added after which distilled water is added to make up the volume to 100 ml in volumetric flask.

Kinetics Analysis of Phytases Using Inositol-6-Phosphate (InsP6, IP6) and Inositol-4-Phosphate (InsP4, IP4) as Substrates The kinetics of phosphate formation was analysed for both IP6 and IP4 substrates using fermentation culture supernatants from the *T. reesei* transformants. The assays were run at pH 3.0 and pH 5.0. The enzyme preparations were first desalted using PD 10 columns as follows. 2.5 ml of the phytase material was loaded on the PD 10 column and eluted using 0.2 M citrate buffer, pH 5.0. 3.5 ml of the eluate was collected. The eluate was diluted with 0.2 M Na Citrate/0.15 M NaCl, pH 5.0 or with 0.2 M Glycine/HCl/ 0.15 M NaCl, pH 3.0, for the pH 5 and pH 3 analysis, respectively.

The phytic acid dodecasodium salt (IP6) used in the analysis was purchased from Sigma-Aldrich (Taufkirchen, Germany). Method to generate mainly IP4 specific isomer fraction was performed in 4 steps. In a first step Quantum Blue phytase was immobilized on 5 ml HiTrap NHS-activated sepharose column from General electric (Boston, USA) as described in Greiner & Konietzky, (1996). In a second step, the immobilized phytase degraded IP6 in 0.1 M Na-acetate buffer pH 5.0 stepwise to lower inositol phosphates. The flowrate of 5 ml/min achieved the highest portion of IP4. The next step was used to remove phosphate from the solution and separate IP4 from other undesired inositol phosphates. Therefore, a manually packed anion exchange column with AG1-x4 resin from Biorad (Hercules, USA) was loaded with the produced inositol phosphate mix and $IP_4$ was eluted with 0.5 M HCl. In the last step, HCl was removed with a rotating evaporator and IP4 re-dissolved in water.

The kinetic reaction with IP6 and IP4 as a substrate were run for 10 minutes at 37° C. and absorbance at 820 nm was followed.

Example 3. Expression of a Set of Bacterial Derived Potential Phytase Genes in *E. coli* as a Pre-Screening A pre-screening of bacterial derived sequences obtained from the gene bank search (Example 1) was performed in *E. coli* prior to expression of chosen molecules in the production platform *Trichoderma reesei* (Example 5) and *Bacillus pumilus* (Example 6). This approach was chosen as it offers a faster expression of a high number of molecules. Fungal derived phytase genes from the database search were directly screened in *Trichoderma* (Example 4).

A total of 192 bacterial HAP genes were chosen for expression in *E. coli* from a sequence research of public databases (Example 1). Sequences were ordered from Genewiz as cloned into the plasmid pET28-(a) for intracellular *E. coli* expression. The plasmids obtained were transformed by the heat-shock method into *E. coli* Shuffle T7 Express (NEB). The transformants were cultivated in shake flasks. Therefore, a pre-culture in 10 mL LB+30 mg/mL kanamycin was inoculated from a fresh plate with a single colony and incubated at 30° C. overnight under shaking at 200 rpm. The main-culture, carried out in 50 mL LB+30 mg/mL kanamycin was inoculated with 0.5 mL from the pre-culture and incubated at 30° C. and 250 rpm till $OD_{600} \approx 1.0$ was reached. Induction was initiated by adding 1 mM (final concentration) IPTG. Afterwards, the culture was further incubated at 16° C. and 250 rpm for 18 hours. After the cultivation was finalised, the cells were harvested by centrifugation, washed with ¼ of the culture volume using 10% glycerol and cell pellets were frozen at −20° C. The cells were lysed using DNase-lysis buffer (50 mM Tris, 2.5 mM $MgCl_2$, 0.5 mM $CalCl_2$, 1 mg/ml lysozyme, 1 U/ml DNase I). The pellet was resuspended in DNase-lysis buffer and the suspension was incubated for 1 hour at 37° C. The cell debris was removed by centrifugation. The supernatant representing the whole intracellular protein extract was used for further analysis.

Figure 1:
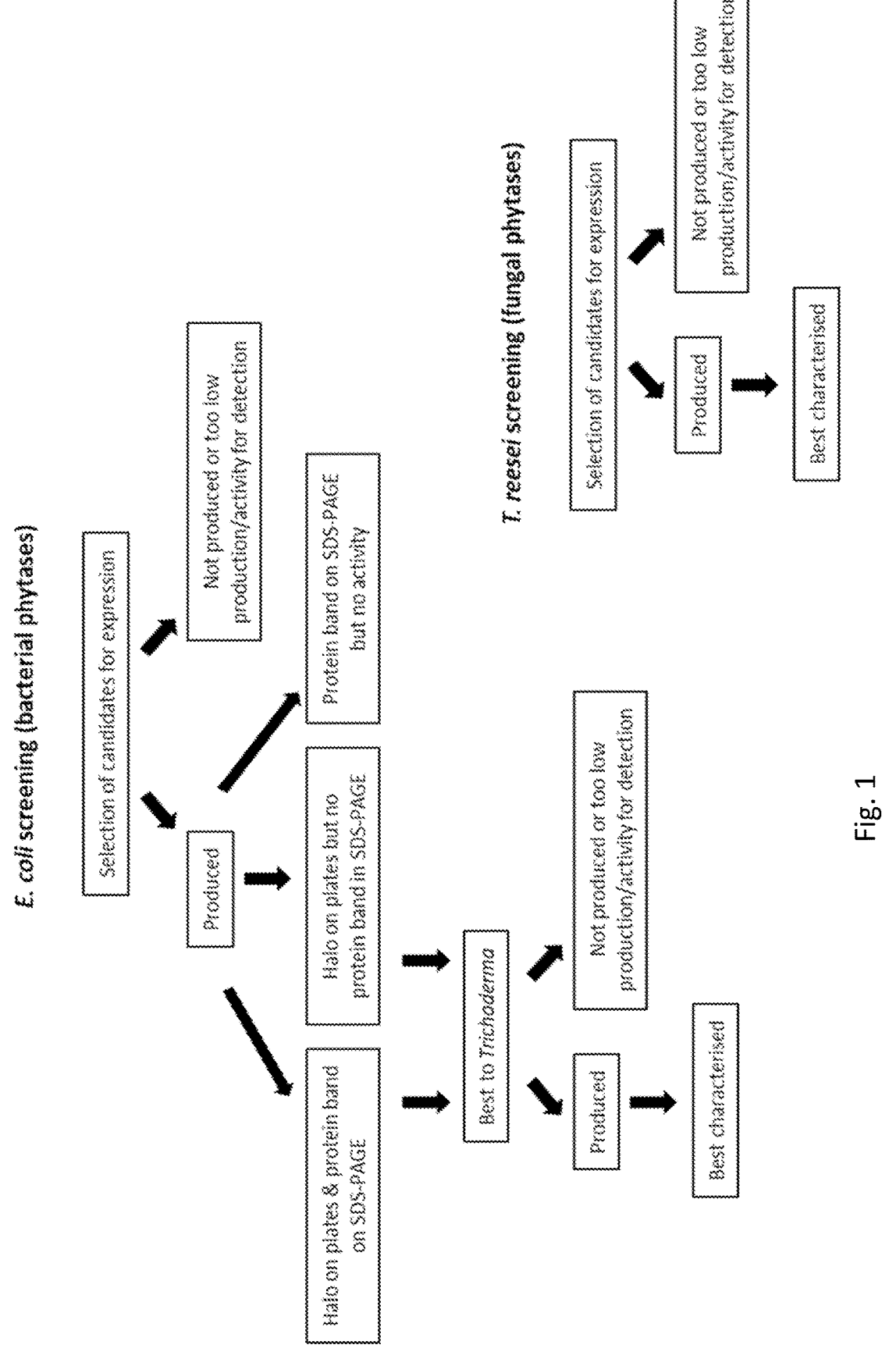
FIG. 1 shows a summary on screening procedure of candidate phytase in *E. coli* and *T. reesei*.

A semi-quantitative plate activity assay (Example 2), an SDS-PAGE and a quantitative high throughput fluorescence-based phosphatase activity assay (4-MUP; Example 2) was performed with each of the protein extracts. Those molecules which showed activity in these tests were additionally directed to a more specific phytase activity assay (PPU assay with IP6 as substrate, Example 2). Molecules produced in *E. coli* showing good phytase activity were chosen for expression in *Trichoderma* (FIG. 1) and, a chosen set of phytases, also in *Bacillus*. For *T. reesei* expression the genes encoding these molecules were re-ordered with optimised codon usage for *T. reesei* (Example 5). For *B. pumilus* expression the codon usage was either that used in *E. coli* expression or *B. pumilus* optimised genes were ordered.

Of the 192 novel potential phytase genes 89 (~46%) were produced in *E. coli* whereas 103 (~54%) were not produced or the production level as protein or phytase activity was too low for detection. Of the above 69 phytases, 35 (~39%) showed activity (formation of a halo) on the phytate selection plate and a protein band was detected in SDS-PAGE analysis, 13 (~15%) were active on plate but no protein band corresponding in mass to the expected phytase mass was detected in SDS-PAGE and 21 (~24%) were not active on plate even though a protein band of expected molecular mass was detected in SDS-PAGE. The protein band in 20 of the 89 candidates was only very faint or only very small halo was formed on phytate plate indicating very low production level.

Altogether 27 novel bacterial phytases which showed the best activities in the analysis performed were chosen for expression in *T. reesei* (Example 5).

Example 4. Expression of a Set of Fungal Derived Phytase Genes in *Trichoderma reesei*

A total of 78 novel phytases from the database searches (Example 1) deriving from fungi (yeasts or filamentous fungi) were chosen to be expressed in *Trichoderma reesei*.

The corresponding genes with their native signal sequence were ordered from GeneArt (ThermoFisher Scientific) as synthetic genes with *T. reesei* codon usage. The genes were cloned to expression cassette in which they were fused (direct fusion) to *T. reesei* cbh1 (cellobiohydrolase 1) promoter. The transcription was terminated by the *T. reesei* cbh2 (cellobiohydrolase 2) terminator. Synthetic gene encoding acetamidase (AmdS) was used as a transformation marker in the plasmids. The PSk268_3MC made an exception as it was produced using a carrier polypeptide, similarly to the bacterial derived phytases expressed in *T. reesei* (Example 5). The plasmids including the expression cassettes were transformed to *T. reesei* using protoplast transformation. From each set, 3-10 transformants were cultivated in shake flasks in cellulase inducing medium and the culture supernatants were analysed in SDS-PAGE gels to confirm whether the phytase was produced and secreted into fungal culture supernatant. The phytase activity was analysed from the culture supernatants in which a visible protein band of expected molecular mass had been detected. The PPU assay (Example 2) was used in the analysis. The candidates showing the best phytase activities in the *T. reesei* culture supernatants (Example 7) were produced in fermenter cultivations and were characterised in more details (Examples 8-9). Culture supernatants from the fermentations of chosen transformants were used in the analysis. The efficiency of the chosen candidates in degradation of phytate in in vitro animal simulation tests was performed as described in Examples 10-13.

From the expressed 78 fungal phytases only 16 (~21%) were well produced in *T. reesei*. The rest were not produced or the production yield was very low, indicating either low expression or production level or sensitivity of the phytase protein to *T. reesei* proteases.

Example 5. Expression of Chosen Bacterial Derived Phytase Genes in *Trichoderma reesei*

The 27 novel bacterial phytases chosen from the *E. coli* screening (Example 3) were ordered as synthetic genes from GeneArt (ThermoFisher Scientific). The genes were ordered as mature phytase encoding sequences (without the native signal sequence) and were fused to a carrier polypeptide encoding sequence in the expression plasm ids. The carrier used was the *T. reesei* CBHII CBD (A) and hinge (B) region from the native CBHII (Paloheimo et al., 2003). A sequence encoding a Kex2 cleavage site (RDKR) was included between the carrier and phytase encoding sequences. The genetic construction was expressed using the *T. reesei* cbh1 promoter. *T. reesei* cbh2 terminator was used to terminate the transcription. A synthetic gene encoding the acetamidase (AmdS) was included as a transformation marker in the plasmids. The plasmids including the expression cassettes were transformed to *T. reesei* using protoplast transformation. A selection of transformants from each transformation was cultivated and the phytases produced were characterised in similar way as described for the fungal derived phytases (Example 4).

From the expressed bacterial phytases 13 (48%) were produced in *T. reesei*. The rest were not produced or the production yield was very low, indicating either low expression or production level or sensitivity of the phytase protein to *T. reesei* proteases.

Example 6. Expression of Chosen Bacterial Derived Phytase Genes in *Bacillus pumilus*

Altogether 15 phytase genes were chosen for expression in *Bacillus pumilus* which could alternatively be used as a production host of novel phytases. Of these candidates, 13 were not produced in *Trichoderma* or their yields were very low. Two of the genes, encoding the phytases PSf203 and BA59 were well produced in *Trichoderma*. For 10 of the candidates, both the *E. coli*- and *Bacillus*-optimized DNA sequence was tested in expression for analysis of differential effects by codon usage on expression levels. The *Bacillus*- optimized sequences were ordered from Genewiz and the *E. coli*-optimized sequences were as used in the *E. coli* pre-screening.

The phytase genes were cloned into a *Bacillus* high copy expression plasmid downstream to a signal peptide for extracellular secretion. The plasmid carried a kanamycin resistance cassette for selection. Construction of the plasmid was carried out using a highly competent *Bacillus subtilis* construction host which carries a plasmid for induced competence. The plasmids were transformed into *B. pumilus* production host by using electroporation. Expression was carried out in shake flasks by inoculating a pre-culture in 10 ml LB medium with 20 mg/ml kanamycin and incubating over night at 37° C. under shaking (180 rpm). The main culture was inoculated with 1 ml of the pre-culture and incubated at 180 rpm and 37° C. for 31 h. 20 ml of culture medium (2% Glucose, 6% corn steep powder, 1.32% $(NH_4)_2HPO_4$, 0.05% $MgSO_4{\times}7\ H_2O$, 0.5% $CaCO_3$, pH adjusted to 7.3 and autoclaved for 30 min at 121° C.) were used in the main culture without antibiotic. The cultures were centrifuged for removal of the cells, and supernatants were stored at −20° C. for further analyses. The analyses of the samples included the phytase plate assay, SDS-PAGE and PPU analysis at pH 5 as well as FTU analysis at pH 3 (Example 2).

Protein signal in SDS-PAGE was detected from 11 out of 15 candidates and 8 candidates showed activity on phytase plate assay. In some cases, the protein yield was slightly higher for the *Bacillus*-optimized sequence. Only 3 of the tested candidates (including the PSd65 and PSd67 also expressed in *T. reesei*) were active at pH 3. The activity levels were, however, very low compared to activities obtained when corresponding genes were expressed in *Trichoderma*.

Example 7. Novel Phytases Chosen for Characterisation

Altogether 15 novel phytases with the best measured activities in the *T. reesei* culture supernatants were chosen for characterisation (Table 1). Of the chosen candidates, 7 were of bacterial and 8 of fungal origin. The phytases used for characterisation were produced in *T. reesei*.

TABLE 1

The novel phytases selected for characterisation.
The name of the phytase, the origin of the gene, SEQ ID NO of the full-length amino acid sequence, the SEQ ID NO of the nucleotide sequence used in the expression cassette and the original database entry number are shown.

| Enzyme | Gene origin | Amino acid sequence SEQ ID no: | Nucleotide sequence SEQ ID no: | Database entry no |
|---|---|---|---|---|
| BA59 | *Budvicia aquatica* | 1 | 2 | gi\|656057413\|ref\|WP_029095759.1\| |
| YE76 | *Yersinia entomophaga* | 3 | 4 | gi\|1035670592\|ref\|WP_064517576.1\| |
| PSd32 | *Pseudomonas* sp. | 5 | 6 | gi\|518661621\|ref\|WP_019823353.1\| |
| PSd34 | *Dickeya* | 7 | 8 | gi\|737364255\|ref\|WP_035346430.1\| |
| PSd35 | *Dickeya dadantii* | 9 | 10 | tr\|D2BZQ9\|D2BZQ9_DICD5 |
| PSd65 | *Bilophila wadsworthia* | 11 | 12 | tr\|E5Y8B1\|E5Y8B1_BILWA |
| PSd67 | *Succinatimonas hippei* | 13 | 14 | tr\|E8LI73\|E8LI73_9GAMM |
| PSf203 | *Blastobotrys adeninivorans* | 15 | 16 | A0A060SXP8_BLAAD |
| PSf207 | *Wickerhamomyces ciferrii* | 17 | 18 | tr\|K0KLF8\|K0KLF8_WICCF |
| PSk235 | *Daedalea quercina* | 19 | 20 | tr\|A0A165R3T0\|A0A165R3T0_9APHY |
| PSk252 | *Thermoascus aurantiacus* | 21 | 22 | JGI genome project: Theau1, protein_id:65212 |
| PSk256 | *Aspergillus oryzae* | 23 | 24 | From a proprietary strain |
| PSk260 | *Ascosphaera apis* | 25 | 26 | tr\|A0A167UWY1\|A0A167UWY1_9EURO |

TABLE 1-continued

The novel phytases selected for characterisation.
The name of the phytase, the origin of the gene, SEQ ID NO of the full-length amino acid sequence, the SEQ ID NO
of the nucleotide sequence used in the expression cassette and the original database entry number are shown.

| Enzyme | Gene origin | Amino acid sequence SEQ ID no: | Nucleotide sequence SEQ ID no: | Database entry no |
|---|---|---|---|---|
| PSk267_II | *Thielaviopsis punctulata* | 27 | 28 | tr\|A0A0F4ZIJ7\|A0A0F4ZIJ7_9PEZI |
| PSk268_3MC | *Magnaporthe oryzae* | 29 | 30 | tr\|G4N003\|G4N003_MAGO7 |

The identity comparison of the amino acid sequences of the novel phytases is shown in FIG. 10. The comparison was done using Needleman-Wunsch global alignment (Cost matrix: Blosum 62, Gap open penalty 12, Gap extension penalty 3). The signal sequences were removed prior to the analysis. The analysis of the signal sequences was done using SignalP 4.1 (http://www.cbs.dtu.dk/services/SignalP/)

The amino acid sequence identities between the phytases were low (FIG. 10). The highest identity was 75.9% between PSd34 and PSd35 which both are from *Dickeya* species. The identities between other phytases with each other were from 12 to 60.2% (FIG. 10).

Example 8. Analysis of pH and Temperature Profiles of Selected Phytases

Determination of the pH and Temperature Profiles

The pH and temperature profiles of the phytases were measured from the culture supernatants of the corresponding *T. reesei* transformants. *Aspergillus* phytase (ASPAW), *E. coli* wild type phytase and *E. coli* mutant phytase from the product Quantum Blue (QB), all produced in *T. reesei*, were used as references.

The pH profile was measured as phytase activity (PPU, Example 2) in pHs 3.0, 4.0, 5.0 and 6.0 at 50° C. The pH of the reaction buffer (0.2 M citrate buffer) was adjusted to reaction pH using citric acid. The activity of an enzyme at each pH is shown as the relative activity (%) normalized to the activity value at the optimum pH of the enzyme in question (Table 2).

TABLE 2

The pH profiles of a selection of novel phytases.
The relative phytase activity (%) compared to the activity of the phytase
at its optimum pH is shown. The references were the *Aspergillus* phytase
(ASPAW) and *E. coli* wild type and mutant phytase.

| Enzyme | pH | | | |
|---|---|---|---|---|
| | 3 | 4 | 5 | 6 |
| *E. coli* wt phytase | 85 | 100 | 69 | 12 |
| *E. coli* mutant phytase | 56 | 100 | 72 | 2 |
| BA59 | 72 | 100 | 67 | 9 |
| YE76 | 77 | 100 | 61 | 11 |
| PSd32 | 1 | 92 | 100 | 19 |
| PSd34 | 0 | 100 | 37 | 2 |
| PSd35 | 55 | 100 | 40 | 2 |
| PSd65 | 40 | 100 | 27 | 0 |
| PSd67 | 61 | 100 | 68 | 17 |
| ASPAW | 59 | 84 | 100 | 56 |
| PSf203 | 48 | 100 | 97 | 4 |
| PSf207 | 0 | 66 | 100 | 0 |
| PSk235 | 0 | 27 | 100 | 91 |
| PSk252 | 20 | 62 | 100 | 72 |
| PSk256 | 9 | 59 | 100 | 87 |
| PSk260 | 10 | 84 | 100 | 27 |

TABLE 2-continued

The pH profiles of a selection of novel phytases.
The relative phytase activity (%) compared to the activity of the phytase
at its optimum pH is shown. The references were the *Aspergillus* phytase
(ASPAW) and *E. coli* wild type and mutant phytase.

| Enzyme | pH | | | |
|---|---|---|---|---|
| | 3 | 4 | 5 | 6 |
| PSk267_II | 45 | 75 | 100 | 67 |
| PSk268_3MC | 0 | 63 | 97 | 100 |

Most of the novel bacterial phytases as well as the bacterial references had their pH optimum at pH 4 whereas most of the fungal ones and the fungal reference at pH 5. BA59, YE76, PSd35, PSd65, PSd67, PSf203 and PSk267_II and the reference phytases had relatively good activity (40% or more) still at pH 3.

Determination of the Temperature Profile

The temperature profile was determined as phytase activity (PPU, Example 2) at temperatures of 40-80° C. at pH 5.0 (Table 3). The activity at each temperature is shown as relative activity (%) normalized to the value at optimum temperature of each phytase.

TABLE 3

The temperature profiles of a selection of novel phytases.
The relative phytase activities (%) compared to the activity at
optimum temperature are shown. The references were the *Aspergillus*
phytase (ASPAW) and *E. coli* wild type and mutant phytase.

| Phytase | Temperature | | | | |
|---|---|---|---|---|---|
| | 40 | 50 | 60 | 70 | 80 |
| *E. coli* wt | 43 | 74 | 100 | 17 | 14 |
| *E. coli* mutant phytase | 32 | 51 | 78 | 100 | 83 |
| BA59 | 52 | 78 | 100 | 3 | 0 |
| YE76 | 69 | 100 | 87 | 4 | 4 |
| PSd32 | 81 | 100 | 22 | 5 | 5 |
| PSd34 | 77 | 100 | 6 | 4 | 4 |
| PSd35 | 67 | 100 | 91 | 7 | 4 |
| PSd65 | 56 | 95 | 100 | 62 | 5 |
| PSd67 | 51 | 82 | 100 | 2 | 3 |
| ASPAW | 39 | 56 | 69 | 100 | 3 |
| PSf203 | 29 | 54 | 82 | 100 | 0 |
| PSf207 | 61 | 100 | 0 | 0 | 0 |
| PSk235 | 100 | 20 | 0 | 0 | 0 |
| PSk252 | 56 | 95 | 100 | 0 | 0 |
| PSk256 | 63 | 100 | 0 | 0 | 0 |
| PSk260 | 73 | 100 | 16 | 0 | 0 |
| PSk267_II | 43 | 68 | 100 | 0 | 0 |
| PSk268_3MC | 55 | 100 | 11 | 1 | 2 |

The temperature optimum of the *E. coli* wild type reference, BA59, PSd65, PSd67, PSk252 and PSk267_II was at 60° C. and that of YE76, PSd32, PSd34, PSd35, PSf207, PSk256, PSk260 and PSk268_3MC at 50° C. PSd65 had high activity (62%) still at 70° C. The temperature optimum of the *E. coli* mutant phytase was at 70° C. and it was still highly active (83%) at 80° C. PSf203 and the fungal reference phytase (ASPAW) had their temperature optima at 70° C. PSk235 had its optimum at 40° C.

Stability in elevated temperature would be advantageous e.g. when the polypeptide is used in feed formulations that are processed at high temperature during manufacture, such as in production of granulated formulations or feed conditioning and pelleting.

Example 9. Kinetic Analysis of Purified Phytases Using IP6 and IP4 Isomers

The selected novel phytases produced in *T. reesei* were used for kinetical analysis with IP6 and IP4 isomers as substrates as described in Example 2. The commercial Quantum Blue phytase product (QB) and the *Aspergillus* derived ASPAW were used as references in the analysis.

The reference phytases QB and ASPAW degraded IP6 more efficiently than IP4 at both pH 3 and 5 (FIGS. 4A-B and FIG. 4O-P, respectively). Several of the novel phytases were more efficient than the references in degrading IP4 (FIG. 4). PSd65, PSd67 and PSk256 degraded IP4 more efficiently than IP6 at both pHs 3 and 5. PSf203, BA59 and YE76 were efficient in IP4 degradation at pH 3 and PSd35 at pH 5. The other tested phytases (PSd34, PSk260 and PSk267_II) were more efficient in degrading IP6 compared to IP4 at both pHs.

Example 10. Gastrointestinal Simulation (GIT) Test

The comparison of selected novel phytase candidates showing good IP4 degradation (and PSk260 as negative control) in their ability to degrade phytate in feed materials was done using the gastrointestinal simulation (GIT) test system. The GIT (Sommerfeld et al., 2017) is a three-step continuous in vitro simulation test to analyse the ability of phytases to degrade phytate in feed materials under animal digestive conditions. The reactions are run at 40° C. and at corresponding pHs and changes of pH as in the crop, gizzard and small intestine of broilers. Corresponding digestive enzymes are also added. To succeed in the GIT assay, the phytase needs to have a combination of beneficial biochemical properties. It needs to resist and act at different pHs and at the temperature of the digestive track. It also needs to be resistant to proteases of the digestive track.

In the GIT screening test 250 FTU of phytase per kg of substrate material was used. The phytase sample was added to 1 g of finely ground corn-soybean material at pH 5.2 and first incubated at 40° C. for 30 min after which the pH was decreased to 2.9 by addition of HCl. Pepsin was added (3000 U/g). After incubation for 45 min, the pH was increased to 6.1 by addition of NaOH. Also, pancreatin was added (18.5 mg/g). The mixture was incubated for 60 min. The reaction was terminated with a total of 10 ml 0.1 M NaF, 0.2 M EDTA, pH 8.00 on ice. Inositol phosphates were extracted for 2×30 min in the stopping solution. Phytase was removed from the supernatant with 30 kDa centrifugal filters before analysis of inositol phosphates (IP6-IP3) using high-performance ion chromatography method (HPIC). The IP6-IP3 analysis was done according to Blaabjerg et al. 2010 (K. Blaabjerg et al./J. Chromatogr. B 878 (2010) 347-354).

The culture supernatants from the fermentation cultivations of phytase producing *T. reesei* transformants were used as samples in the GIT assay. The novel phytases BA59, PSd35, PSd65, PSd67 and PSf203 were more efficient in degrading the substrate to lower IPs compared to the references. YE76, PSk256 and PSk260 were not better than the references in IP6 degradation. The results obtained are shown in FIG. 5 and summarised in Table 4.

TABLE 4

Summary of GIT results.
QB, Quantum Blue phytase product; Ref., *E. coli* mutant phytase,
phytase from Quantum Blue product produced in *T. reesei* in similar
fermentation as the novel phytases.

| Enzyme | Result |
|---|---|
| QB | FIG. 5A, 5B |
| *E. coli* mutant phytase (Ref.) | FIG. 5A |
| BA59 | More phosphate released and IP6-4 degraded to IP3 compared to references (QB, *E. coli* mutant phytase from QB); FIG. 5A |
| YE76 | Not better than reference (QB) in IP6 degradation; FIG. 5B |
| PSd35 | More phosphate released and degradation of lower inositol phosphates very fast compared to references (QB, *E. coli* mutant phytase from QB); FIG. 5A |
| PSd65 | Degraded IP6 completely under test situation and less IP4 compared to reference (QB); FIG. 5B |
| PSd67 | More phosphate released and slightly more IP4 degraded compared to references (QB, *E. coli* mutant phytase from QB); FIG. 5A |
| PSf203 | More phosphate released and more effective degradation of lower inositol phosphate IP4 compared to references, (QB, *E. coli* mutant phytase from QB); FIG. 5A |
| PSk256 | Less effective than reference in IP6 degradation; FIG. 5B |
| PSk260 | Less effective than reference in IP6 degradation; FIG. 5B |

A dose effect test study was performed in which different amounts of activity units (125, 250, 500 and 1000 FTU/kg substrate material) were added. Dose effect studies were run with two novel phytases, BA59 and PSd65. The mutant *E. coli* phytase from the Quantum Blue product was used as a reference. In these tests BA59 and PSd65 degraded clearly more IP4 and produced much more lower inositol phosphates with increasing dose compared to reference (FIG. 6).

Example 11. Gastrointestinal Simulation (GIT) Assay Using Feed with Mineral Addition as a Substrate In this experiment the GIT assay with BA59, PSd65 and reference phytase was performed using a feed material with minerals and other feed ingredients added instead of pure corn-soybean meal mix. The feed material was used to identify differences in the vulnerability by minerals and other feed ingredients between the phytase candidates while degrading phytate. 250, 500 and 1000 FTU/kg of the phytases were dosed.

BA59 and PSd65 produced much more of the lower inositol phosphates with increasing dose compared to reference also when the feed material with minerals was used as a substrate (FIG. 7).

Example 12. Gastrointestinal Simulation (GIT) Test Using Three Substrates

In this experiment the GIT assay with BA59, PSd65 and reference phytase was performed using three substrates: a corn-soybean meal and two mixed feeds with other feed ingredients added, the other with 5.4 g/kg of phosphorus and 9 g/kg of calcium ("negative control feed", NC) and the other with 8 g/kg of phosphorus and 9 g/kg of calcium ("positive control feed", PC). The dose of 250 FTU/kg of the phytases were used in the experiment.

BA59 and PSd65 produced more of the lower inositol phosphates from all the substrates compared to reference (FIG. 8).

The efficiency of BA59 and PSd65 in animal feeding tests was also confirmed.

Example 13. Gastrointestinal Simulation (GIT) Test for Novel Phytases Combined with Mutant E. Con Phytase Included in Commercial Quantum Blue (QB) Product As some of the novel phytases were better than QB in IP4 degradation, the efficiency of combination of novel phytases with *E. coli* mutant phytase from QB was tested using the GIT assay. These phytases were combined based on phytase activity (FTU/kg, pH 5.5) with a set activity of *E. coli* mutant phytase (250 FTU/kg) and increasing doses of either BA59 or PSd65 (62.5, 125 and 250 FTU/kg). As a reference, identical additional doses of *E. coli* mutant phytase were added.

When 62.5 FTU/kg BA59 and PSd65 were added, IP6, IP5 and IP4 were more efficiently degraded further compared to the reference test. Both BA59 and PSd65 degrade more IP4 than *E. coli* mutant phytase from QB, PSd65 being more efficient.

With an increasing dosage of BA59 and PSd65 to 250 FTU/kg of *E. coli* mutant phytase, more IP4 was degraded as when the same activity of *E. coli* mutant phytase was added. For both dosages, 125 and 250 FTU/kg, PSd65 was the most effective. At the dosage of 250 FTU/kg, PSd65 degrades more than half of the IP4 than the same activity in the form of *E. coli* mutant phytase. All combination dosages with BA59 lead to better degradation compared to *E. coli* mutant phytase, whereas addition of 250 FTU/kg was the most efficient in IP4 degradation.

The results (averages from two replicate tests) are shown in FIG. 9.

REFERENCES

Bedford, M. R. and C. L. Walk. 2016. Reduction of phytate to tetrakisphosphate (IP4) to trisphosphate (IP3), or perhaps even lower, does not remove its antinutritive properties. In: Phytate destruction—consequences for precision animal nutrition. Eds. Walk, C. L., Kühn, I., Stein, H. H., Kidd, M. T. and Rodehutscord, M. Wageningen Academic publishers: 45-52.

Lee, S. A. and M. R. Bedford. 2016. Inositol—An effective growth promotor? World's Poultry Science Journal. 72: 743-760.

Menezes-Blackburn, D., S. Gabler and R. Greiner. 2015. Performance of Seven Commercial Phytases in an in Vitro Simulation of Poultry Digestive Tract. J Agric. Food Chem. 63: 6142-6149.

Xu, P., J. Price, A. Wise, and P. J. Aggett. 1992. Interaction of Inositol Phosphates with Calcium, Zinc, and Histidine. Journal of Inorganic Biochemistry 47: 119-130.

Zeller, E., M. Schollenberger, I. Kuhn and M. Rodehutscord. 2015. Hydrolysis of phytate and formation of inositol phosphate isomers without or with supplemented phytases in different segments of the digestive tract of broilers. Journal Nutritional Science 4, e1: 1-12.

The invention claimed is:

1. A composition comprising a first polypeptide and at least one feedingstuff or additive selected from a stabiliser, a preservative, a mineral and a nutrient, wherein the first polypeptide comprises:

an amino acid sequence having at least 90% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15), or a functional fragment thereof;

wherein the first polypeptide or the functional fragment thereof comprises a PFAM motif His_Phos_2 (PF00328), an active site sequence motif RHGXRXP, and a catalytically active HD-dipeptide at the C-terminus; wherein the first polypeptide is an isolated, recombinant or synthetic polypeptide, and wherein the first polypeptide has higher inositol tetrakisphosphate (IP4) degradation activity than inositol hexaphosphate (IP6) degradation activity at pH 3.

2. A composition according to claim 1 further comprising a second polypeptides having phytase activity, wherein:

the second polypeptide does not have an identical amino acid sequence with the first polypeptide, and is selected from *Escherichia* (*E.*) *coli* mutant phytase Quantum Blue (QB), an amino acid sequence having at least 85% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15).

3. The composition of claim 1, wherein the composition is a food additive or a feed additive further comprising at least one of: a mineral, an amino acid, a prebiotic, or a probiotic.

4. The composition of claim 1, wherein the composition is in a form of a solution, dispersion, paste, powder, granule, coated granule, tablet, cake, crystal, crystal slurry, gel, extrude or pellet.

5. The composition of claim 2, wherein at least one of the first polypeptide and the second polypeptide are obtained by production in a recombinant host cell.

6. An animal feed comprising the composition of claim 1, and at least one protein source of plant origin, and a. optionally at least one enzyme selected from protease, amylase, phytase, xylanase, endoglucanase, beta-glucanase, or a combination thereof; and b. optionally at least one filler selected from maltodextrin, flour, salt, sodium chloride, sulfate, sodium sulfate, or a combination thereof.

7. A feed supplement comprising the composition of claim 1; and a. optionally at least one enzyme selected from protease, amylase, phytase, xylanase, endoglucanase, beta-glucanase, or a combination thereof; and b. optionally at least one filler selected from maltodextrin, flour, salt, sodium chloride, sulfate, sodium sulfate, minerals, amino acids, prebiotics, probiotics or a combination thereof.

8. A method for producing an animal feed comprising combining a nutrient component including one or more of a carbohydrate, a fat or a protein with a polypeptide comprising:

an amino acid sequence having at least 90% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15), of a functional fragment thereof;

wherein the first polypeptide or the functional fragment thereof comprises a PFAM motif His_Phos_2 (PF00328), an active site sequence motif RHGXRXP, and a catalytically active HD-dipeptide at the C-terminus; wherein the polypeptide has higher IP4 degradation activity than IP6 degradation activity at pH 3, thereby producing the animal feed.

9. A method for producing food comprising combining a nutrient component including one or more of a carbohydrate, a fat or a protein with a polypeptide comprising:

an amino acid sequence having at least 90% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15), or a functional fragment thereof;

wherein the first polypeptide or the functional fragment thereof comprises a PFAM motif His_Phos_2 (PF00328), an active site sequence motif RHGXRXP, and a catalytically active HD-dipeptide at the C-terminus; wherein the polypeptide has higher IP4 degradation activity than IP6 degradation activity at pH 3, thereby producing the food.

10. A method for producing animal feed additives comprising combining a nutrient component including one or more of a carbohydrate, a fat, or a protein with a polypeptide comprising an amino acid sequence having at least 90% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15), or a functional fragment thereof;

wherein the first polypeptide or the functional fragment thereof comprises a PFAM motif His_Phos_2 (PF00328), an active site sequence motif RHGXRXP, and a catalytically active HD-dipeptide at the C-terminus; wherein the polypeptide has higher IP4 degradation activity than IP6 degradation activity at pH 3, thereby producing the animal feed additives.

11. A method for producing food additives comprising combining a nutrient component comprising one or more of a carbohydrate, a fat, or a protein with a polypeptide comprising an amino acid sequence having at least 90% sequence identity with amino acids 26-439 of BA59 (SEQ ID NO: 1), amino acids 24-424 of PSd65 (SEQ ID NO: 11), amino acids 25-403 of PSd67 (SEQ ID NO: 13), or amino acids 16-469 of PSf203 (SEQ ID NO: 15), or a functional fragment thereof;

wherein the first polypeptide or the functional fragment thereof comprises a PFAM motif His_Phos_2 (PF00328), an active site sequence motif RHGXRXP, and a catalytically active HD-dipeptide at the C-terminus; wherein the polypeptide has higher IP4 degradation activity than IP6 degradation activity at pH 3, thereby producing the food additives.

* * * * *

SEQUENCE LISTING

<160> NUMBER OF SEQ ID NOS: 30

<210> SEQ ID NO 1
<211> LENGTH: 439
<212> TYPE: PRT
<213> ORGANISM: Budvicia aquatica

<400> SEQUENCE: 1

```
Met Glu Ile Ile Asp Arg Leu Ser Lys Leu Ser Ala Leu Met Leu Leu
1               5                   10                  15

Gly Cys Ser Cys Leu Pro Ala Leu Ala Val Ser Thr Pro Val Asn Gly
            20                  25                  30

Tyr Val Leu Glu Arg Val Val Ile Leu Ser Arg His Gly Val Arg Ser
        35                  40                  45

Pro Thr Lys Gln Thr Asp Leu Met Asn Asn Val Thr Pro Asp Lys Trp
    50                  55                  60

Pro Gln Trp Pro Val Gln Ala Gly Tyr Leu Thr Pro Gln Gly Glu His
65                  70                  75                  80

Leu Met Thr Leu Met Gly Gly Phe Tyr Arg Asp Tyr Phe Arg Ser His
                85                  90                  95

Asn Leu Leu Pro Ser Gln Gly Cys Pro Thr Asp Gly Ser Leu Tyr Val
            100                 105                 110

Trp Ala Asp Ile Asp Gln Arg Thr Arg Leu Thr Gly Gln Ala Phe Leu
        115                 120                 125

Ala Gly Val Ala Pro Glu Cys Asp Leu Lys Ile His His Gln Ala Asp
    130                 135                 140
```

-continued

```
Leu Lys Thr Thr Asp Ala Leu Phe His Pro Val Glu Ala Gly Ile Cys
145                 150                 155                 160

Lys Leu Asp Lys Gln Gln Thr Gln Gln Ala Val Glu Lys Gln Leu Gly
                165                 170                 175

Ala Pro Leu Ala Thr Leu Ser Gln Arg Tyr Ala Leu Pro Leu Ala Gln
            180                 185                 190

Met Gly Glu Ile Leu Asn Phe Ala Ala Ser Pro Tyr Cys Lys Glu Met
            195                 200                 205

Gln Thr Lys Gly Gln Ser Cys Asp Phe Ala Ser Phe Thr Pro Asn Gln
        210                 215                 220

Ile His Leu Ser Pro Asn Gly Gln Lys Val Ser Leu Ser Gly Pro Leu
225                 230                 235                 240

Ala Leu Ser Ser Thr Leu Ser Glu Ile Phe Leu Leu Gln Tyr Ala Gln
            245                 250                 255

Gly Met Pro Glu Val Ala Trp Gln Arg Leu Ser Gly Glu Asp Asn Trp
            260                 265                 270

Arg Ser Leu Met Ser Leu His Asn Glu Gln Phe Asn Leu Met Ala Lys
        275                 280                 285

Thr Pro Tyr Ile Ala Ser His Lys Gly Thr Pro Leu Leu Lys Glu Ile
        290                 295                 300

Ser Ala Thr Leu Ala Gly Gln Gln Gly Thr Leu Lys Arg Pro Ala Asn
305                 310                 315                 320

Asn Arg Ile Leu Phe Ile Ala Gly His Asp Thr Asn Ile Ala Asn Ile
            325                 330                 335

Ala Gly Met Leu Gly Leu Asn Trp Glu Leu Pro His Gln Pro Asp Asn
            340                 345                 350

Thr Pro Pro Gly Gly Gly Leu Val Phe Glu Leu Trp Asn Asn Pro Gln
        355                 360                 365

Asp His Gln Gln Tyr Val Ser Val Lys Met Phe Tyr Gln Thr Met Glu
        370                 375                 380

Gln Leu Arg Asn Gly Glu Lys Leu Asp Met His His Pro Ala Gly Met
385                 390                 395                 400

Val Gln Val Ala Ile Ala Gly Cys Glu Asn Ser Asn Ser Ser Val Leu
            405                 410                 415

Cys Ser Leu Lys Asp Leu Gln Lys Lys Val Ser Gln Ala Ile Gln Pro
            420                 425                 430

Ala Cys Gln Leu Ser Met Gln
            435
```

```
<210> SEQ ID NO 2
<211> LENGTH: 1245
<212> TYPE: DNA
<213> ORGANISM: Budvicia aquatica

<400> SEQUENCE: 2
gtcagcacgc cgttaacgg ctatgtcctc gagcgcgtcg tcatcctcag ccgccacggc      60
gtccgaagcc ctaccaaaca gacggacctc atgaacaacg tcacccccga taaatggcct     120
cagtggcccg ttcaagctgg ctacctcacc cctcaaggtg agcatttaat gaccctcatg     180
ggcggctttt accgcgacta ctttcgcagc cacaatttac tgccctcgca aggttgccct     240
accgacggca gcctctacgt gtgggccgac atcgaccagc gcacccgact caccggtcaa     300
gcttttctcg ctggcgtcgc ccccgaatgc gacctcaaga tccaccatca agctgattta     360
aagacgaccg acgctttatt tcaccccgtc gaggctggca tctgcaaact ggacaagcag     420
```

-continued

```
cagacccagc aagctgtcga aaagcagctc ggcgcccctc tcgccacgct gagccagcga      480
tacgctctgc ccctcgccca aatgggcgag atcctcaatt ttgccgccag cccctactgc      540
aaggaaatgc agaccaaggg ccaatcgtgc gacttcgctt cgttcacccc caaccagatc      600
catctcagcc ccaacggcca gaaagtgtcg ctgagcggtc ctctcgccct cagctcgacc      660
ctcagcgaga tcttttttact ccaatacgcc caaggtatgc ccgaagtcgc ttggcaacgc      720
ctctcgggcg aggacaactg cgcgctcttta atgtctttac acaacgagca gttcaattta      780
atggccaaga ccccctacat cgccagccac aagggcaccc ctttactcaa ggagatcagc      840
gccaccctcg ctggccagca aggtaccctc aagcgccccg ctaacaaccg catcctcttc      900
atcgccggtc acgacaccaa catcgccaac atcgctggca tgctgggcct caactgggaa      960 ctccccacc agcccgataa tacgcctccc ggcggtggcc tcgtctttga gctgtggaac     1020
aacccccaag atcaccagca gtacgtcagc gtgaagatgt tttaccagac gatggagcag     1080
ctgcgcaacg gcgagaagct ggatatgcac catcccgctg gcatggtgca agttgccatc     1140
gctggctgcg agaacagcaa tagcagcgtg ctgtgtagcc tcaaggattt acagaagaag     1200
gtcagccaag ccatccaacc cgcttgtcag ctctcgatgc agtaa                     1245
```

<210> SEQ ID NO 3
<211> LENGTH: 454
<212> TYPE: PRT
<213> ORGANISM: Yersinia entomophaga

<400> SEQUENCE: 3

```
Met Ile Thr Ile Lys Arg Lys Leu Ser Leu Ser Ala Met Ile Leu Thr
1               5                   10                  15

Phe Ile Gly Ser Ala Ile Thr Ile Pro Lys Val Val Ala Glu Glu Val
            20                  25                  30

Gly Tyr Thr Leu Glu Lys Val Val Ile Leu Ser Arg His Gly Val Arg
        35                  40                  45

Ser Pro Thr Lys Gln Thr Glu Leu Met Asn Glu Val Thr Pro Asp Lys
    50                  55                  60

Trp Pro Glu Trp Pro Val Lys Ala Gly Tyr Leu Thr Pro Arg Gly Glu
65                  70                  75                  80

Gln Leu Val Lys Ile Met Gly His Phe Tyr Gly Gln Tyr Phe Arg His
                85                  90                  95

Thr Gly Leu Leu Pro Lys Glu Arg Cys Pro Ala Glu Gly Gln Val Tyr
            100                 105                 110

Val Tyr Ser Asp Ile Asp Gln Arg Thr Leu Leu Thr Gly Gln Ala Leu
        115                 120                 125

Ile Asp Gly Ile Ala Pro Gln Cys Gly Phe Lys Ile Phe His Gln Lys
    130                 135                 140

Asn Leu Lys Gln Ile Asp Pro Leu Phe His Pro Val Glu Ala Gly Ile
145                 150                 155                 160

Cys Ala Leu Asn Ala Lys Lys Thr Gln Glu Ala Ile Glu Lys Lys Leu
                165                 170                 175

Gly Ala Pro Ile Thr Thr Leu Ser Gln Arg Tyr Ala Lys Ser Leu Ala
            180                 185                 190

Leu Met Gly Lys Val Leu Asn Phe Ser Ala Ser Pro Tyr Cys Gln Lys
        195                 200                 205

Met Glu Lys Gln Gly Met Asp Cys Asn Phe Ala Asp Leu Ser Pro Asn
    210                 215                 220
```

-continued

```
Glu Val Gln Val Asn Gln Glu Gly Ser Lys Ala Ser Leu Ser Gly Pro
225                 230                 235                 240

Val Ala Leu Ser Ser Thr Leu Ala Glu Ile Phe Leu Leu Gln Asn Ser
            245                 250                 255

Gln Gly Met Pro Ile Val Ala Trp His Arg Leu Leu Thr Arg Glu Asp
            260                 265                 270

Trp Gln Thr Leu Met Leu Leu His Asn Ser Gln Phe Asp Leu Met Ala
        275                 280                 285

Lys Thr Pro Tyr Ile Ala Gln His Lys Gly Thr Pro Leu Leu Gln Gln
    290                 295                 300

Ile Asn Val Ala Leu Leu Gln Pro Glu Gln Gly Lys Ala Gly Leu Asp
305                 310                 315                 320

Lys Gln Pro Ala Thr Lys Lys Thr Leu Ser Asn Thr Gln Leu Pro Asp
            325                 330                 335

Asn Asn Ala Val Phe Ile Leu Gly Gly His Asp Thr Asn Ile Ala Asn
            340                 345                 350

Val Ala Gly Met Leu Gly Leu Asn Trp Thr Leu Pro Leu Gln Pro Asp
        355                 360                 365

Asn Thr Pro Pro Gly Gly Gly Leu Val Phe Glu Arg Trp Arg Asp Gln
    370                 375                 380

His Gly Gln Ser Phe Val Ala Ile Lys Met Phe Tyr Gln Thr Leu Asn
385                 390                 395                 400

Gln Leu Arg Asn Met Glu Lys Leu Asp Leu Ser Ile Asn Pro Ala Gly
            405                 410                 415

Met Val Ser Ile Asp Ile Pro Gly Cys Glu Asn Glu Gly Glu Asn Lys
            420                 425                 430

Leu Cys Arg Leu Ala Thr Phe Gln Lys Lys Val Val Glu Ala Ile Glu
        435                 440                 445

Pro Ala Cys Asn Leu Pro
    450
```

```
<210> SEQ ID NO 4
<211> LENGTH: 1296
<212> TYPE: DNA
<213> ORGANISM: Yersinia entomophaga

<400> SEQUENCE: 4
atccccaagg tggtcgccga ggaggtcggt tacaccctcg agaaggtggt catttatct       60 cgtcacggtg tccgcagccc cacgaagcag accgagctca tgaacgaggt caccccgac      120 aagtggcccg aatggcccgt caaagccggt tacctcaccc cccgaggcga gcagctcgtc     180
aagatcatgg ccacttcta cggccagtac ttccgccaca ccggcctcct ccccaaggag      240
cgatgtcccg ctgagggcca agtttacgtc tacagcgaca ttgatcagcg aacgctgctg     300
accggccaag ctctgatcga cggcatcgcc ccccagtgcg gcttcaagat cttccaccag     360
aagaacctca aacagatcga cccttttattc caccccgttg aggctggcat ttgcgccctc    420
aacgccaaaa agacccaaga agctatcgaa aagaagctgg gcgcccccat caccacttta     480
agccagcgct acgccaagtc gctcgccctc atgggtaaag tcctcaactt cagcgccagc     540
ccctactgtc agaagatgga gaagcaaggt atggactgca acttcgccga cctctcgccc     600
aacgaggtcc aagttaatca agaaggctcg aaggcctctt tatcgggtcc cgtcgctctc     660
agcagcaccc tcgccgagat tttttattta cagaattcgc aaggtatgcc catcgtcgct     720
tggcatcgtt tactcacgcg cgaggattgg cagactttaa tgctgctcca taactcgcaa     780
```

-continued

```
ttcgatctca tggccaagac cccctacatc gcccagcaca agggtacccc tctgctgcag      840
cagatcaacg tcgctttact gcaacccgaa caaggtaagg ccggcctcga caagcagccc      900
gctaccaaga agaccctctc gaacacccag ctccccgata caacgccgt gttcatcctc        960 ggcggccacg acacgaacat cgccaacgtg gccggcatgc tgggcctcaa ctggactttta    1020 cctctccagc ccgataacac ccctcccggt ggtggcctcg tctttgagcg ctggcgagac      1080
cagcacggcc agtcgtttgt cgccatcaag atgttctacc agaccctcaa ccagctccgc      1140
aacatggaga agctcgacct cagcatcaac cccgccggca tggtgagcat cgacatcccc      1200
ggttgtgaga acgagggcga gaacaagctg tgccgcctcg ctaccttcca gaagaaggtg      1260
gtcgaagcca tcgaacccgc ttgtaacctc ccctaa                                1296
```

```
<210> SEQ ID NO 5
<211> LENGTH: 432
<212> TYPE: PRT
<213> ORGANISM: Pseudomonas sp.

<400> SEQUENCE: 5

Met Lys Thr Leu Leu Pro Leu Tyr Thr Gly Leu Leu Leu Ala Ser Met
1               5                   10                  15

Leu Ser Pro Ala Ala Leu Ala Gln Thr Pro Thr Ser Asp Gly Tyr Ala
                20                  25                  30

Leu Asp Lys Val Val Gln Val Ser Arg His Gly Val Arg Pro Pro Thr
            35                  40                  45

Lys Ser Asn Glu Lys Leu Leu Thr Ala Val Thr Gln Arg Gln Trp Pro
        50                  55                  60

Thr Trp Leu Val Pro Phe Gly Asn Leu Thr Gly His Gly Tyr Thr Gly
65                  70                  75                  80

Ala Val Glu Leu Gly Arg Tyr Arg Gly Glu Val Leu Arg Thr Ala Gly
                85                  90                  95

Leu Ile Pro Lys Gly Cys Pro Asp Ala Ser Gln Leu Leu Val His Ala
                100                 105                 110

Ser Pro Leu Gln Arg Thr Lys Ala Thr Ala Gln Ala Leu Leu Asp Gly
            115                 120                 125

Met Phe Pro Gly Cys Gly Leu Gln Pro Thr Tyr Val Ser Gly Asp Gln
            130                 135                 140

Asp Ala Leu Phe Gln Ala Asn Glu Met Pro Phe Ala Ala Leu Asp Pro
145                 150                 155                 160

Val Lys Ala Lys Ala Asp Ile Leu Lys Ala Leu Gly Gly Ser Val Glu
                165                 170                 175

Ala Ala Gln Ala Arg Tyr Lys Pro Phe Glu Glu Lys Leu Arg Glu Ile
            180                 185                 190

Ala Cys Leu Pro Ala Ala Asp Cys Pro Tyr Gly Lys Gln Ala Trp Thr
            195                 200                 205

Leu Glu Gln Asn Ala Lys Gly Arg Phe Ala Ile Lys Gly Leu Ser Ala
        210                 215                 220

Gly Ala Asn Met Gly Glu Val Phe Arg Leu Glu Tyr Ser Gln Gly Leu
225                 230                 235                 240

Pro Val Asp Lys Val Ala Phe Gly Asn Gly Arg Thr Ala Ala Glu Val
                245                 250                 255

Ser Ser Leu Met Val Leu Thr Lys Ala Lys Tyr Asp Tyr Leu Asn Asp
                260                 265                 270
```

-continued

```
Ile Pro Tyr Ile Ala Ser Arg Gly Ala Ser Glu Leu Met Asn Gln Ile
        275                 280                 285

Ser Leu Gln Leu Lys Gln Gly Thr Pro Leu Ala Pro Lys Asp Ala Gln
        290                 295                 300

Ser Ile Pro Pro Asp Val Pro Leu Met Leu Leu Val Ala His Asp Thr
305                 310                 315                 320

Asn Ile Ser Tyr Leu Arg Thr Met Leu Gly Phe Gly Trp Lys Gln Gly
                325                 330                 335

Asp Tyr Ile Glu Asn Asn Ile Pro Pro Val Gly Thr Leu Gln Phe Glu
                340                 345                 350

Arg Tyr Lys Glu Val Lys Thr Gly Glu Tyr Phe Leu Arg Ile Ala Phe
        355                 360                 365

Glu Ala Gln Ser Met Asp Gln Ile Arg Asn Leu Thr Gln Leu Thr Ala
        370                 375                 380

Gly Gln Lys Pro Leu Lys Thr Asp Phe Asn Ser Ala Lys Asp Cys Arg
385                 390                 395                 400

Asn Thr Ser Val Gly Leu Leu Cys Pro Leu Lys Gly Ala Met Ala Thr
                405                 410                 415

Val Asp Gln Asn Ile Asp Pro Thr Ala Leu Thr Pro Tyr Ala Phe Glu
                420                 425                 430
```

```
<210> SEQ ID NO 6
<211> LENGTH: 1230
<212> TYPE: DNA
<213> ORGANISM: Pseudomonas sp.

<400> SEQUENCE: 6 cagacccca cgagcgacgg ctacgcttta gataaggtcg tccaagtcag ccgccacggc      60
gtccgccctc ccaccaagag caacgagaag ctcctcacgg ctgtcaccca cgccagtgg     120 cccacttggc tggtcccctt cggcaacctc acgggccacg gttatacggg cgccgtcgag    180
ctcggccgct atcgcggtga ggtcctccga acggccggcc tcatccctaa gggctgcccc    240
gatgctagcc agctgctggt ccacgctagc cctctgcagc gcaccaaggc tacggcccaa    300
gctctcctcg atggcatgtt ccccggttgc ggcctccaac ccacctacgt cagcggcgac    360
caagatgccc tctttcaagc taacgaaatg ccttttgccg ccctcgaccc cgttaaggct    420
aaggccgaca ttttaaaggc tctcggcggc agcgtcgagg ccgcccaagc tcgctacaag    480
cccttcgagg agaaactccg cgagattgct tgtctgcccg ccgctgactg ccccctatggc    540 aagcaagctt ggaccctcga gcagaacgcc aagggccgct tcgccattaa gggtctcagc    600
gccggcgcca acatgggcga agtgttccgt ttagaataca gccaaggtct ccccgtcgac    660
aaggtcgctt ttggcaacgg ccgaaccgcc gccgaggtga gcagcctcat ggttttaacc    720
aaggccaagt acgactattt aaacgacatc ccttacattg cctctcgtgg tgccagcgag    780
ctcatgaacc agatcagcct ccagctgaaa caaggtacgc ccctcgcccc taaggacgcc    840
caatcgatcc cccccgatgt cccttttaatg ctcctcgtcg cccacgacac gaacatctcg    900
tatttacgca ccatgctcgg tttcggctgg aagcaaggtg actacatcga gaacaacatt    960 cccccgtgg gcactttaca atttgagcgc tacaaggagg tcaagaccgg cgagtacttc   1020
ctccgcatcg cctttgaggc tcaaagcatg gaccagatcc gcaacctcac gcaactcacg   1080
gccggccaga agcccctcaa gacggacttt aacagcgcca aggactgccg caacacgagc   1140
```

```
gtcggcctcc tctgccctct gaagggcgct atggctaccg tcgaccagaa catcgacccc      1200
accgccctca ccccttacgc cttcgagtaa                                       1230
```

<210> SEQ ID NO 7
<211> LENGTH: 424
<212> TYPE: PRT
<213> ORGANISM: Dickeya

<400> SEQUENCE: 7

```
Met Ile Thr Arg Thr Thr Ala Ala Gly Leu Leu Leu Ser Ala Leu Pro
1               5                   10                  15

Leu Phe Asn Thr Gln Ala Gln Thr Thr Thr Asp Trp Gln Leu Glu Lys
            20                  25                  30

Val Val Glu Ile Ser Arg His Gly Val Arg Pro Pro Thr Glu Gly Asn
        35                  40                  45

Met Lys Thr Ile Gln Ala Gly Thr Gly Arg Ala Trp Pro Glu Trp Leu
    50                  55                  60

Thr Arg Tyr Gly Glu Leu Thr Gly His Gly Tyr Ala Ala Ala Val Lys
65                  70                  75                  80

Lys Gly Gln Tyr Glu Gly Asn Tyr Leu Arg Gln His Gly Leu Leu Thr
                85                  90                  95

Gln Gly Cys Pro Gln Pro Gly Glu Leu Phe Val Trp Ala Ser Pro Leu
            100                 105                 110

Gln Arg Thr Arg Glu Thr Ala Met Ala Leu Met Asp Gly Val Phe Pro
        115                 120                 125

Gly Cys Gly Val Ala Ile Gln Gly Pro Ala Ser Glu Asp His Asp Thr
    130                 135                 140

Leu Phe His Ala Glu Asp Ala Gly Val Thr Leu Asp Gln Ala Gln Val
145                 150                 155                 160

Lys Ala Ala Leu Asp His Ala Met Gln Gly Gln Ser Ala Gly Gln Ile
                165                 170                 175

Gln Thr Arg Leu Gln Pro Val Ile Asp Lys Leu Lys Gln Ala Val Cys
            180                 185                 190

Leu Pro Asn Thr Ala Cys Pro Ala Phe Asp Thr Glu Trp Ala Ile Lys
        195                 200                 205

Glu Ser Lys Lys Gly Asn Leu Ser Leu His Gly Pro Glu Thr Leu Ala
    210                 215                 220

Asn Met Ala Glu Thr Ile Arg Leu Ala Tyr Ser Asn Asn Pro Leu
225                 230                 235                 240

Ser Gln Val Ala Phe Gly His Ala Arg Ser Ala Ala Glu Val Gly Thr
                245                 250                 255

Leu Leu Thr Leu Ala Thr Ala Gln Tyr Asp Phe Thr Asn Asp Leu Pro
            260                 265                 270

Tyr Val Ala Arg Arg Gly Ala Ser Thr Leu Met His Gln Ile Ala Leu
        275                 280                 285

Ala Leu Thr Pro Glu Gln Arg Pro Asp Ala Pro Glu Ala Lys Trp
    290                 295                 300

Leu Leu Tyr Val Ala His Asp Thr Asn Ile Ala Lys Leu Arg Thr Leu
305                 310                 315                 320

Leu Gly Phe Thr Trp Gln Gln Gly Asp Tyr Pro Arg Gly Asn Ile Pro
                325                 330                 335

Pro Ala Gly Ser Leu Ile Phe Glu Arg Trp Arg Asn Pro Gln Ser Gly
            340                 345                 350
```

```
Glu Arg Phe Leu Arg Ile Tyr Phe Gln Ala Gln Ser Leu Asp Gln Ile
        355                 360                 365

Arg Asn Leu Asp Pro Leu Asp Asn Gln His Pro Pro Leu Arg Ser Glu
        370                 375                 380

Phe Ser Val Ala Gly Cys Glu Lys Thr Glu Val Gly Thr Val Cys Pro
385                 390                 395                 400

Leu Asp Gly Ala Leu Lys Arg Leu Asn Asp Ala Val Asp Asn Ser Ala
                405                 410                 415

Leu Leu Pro Val Gln Tyr Ser Gln
            420
```

```
<210> SEQ ID NO 8
<211> LENGTH: 1209
<212> TYPE: DNA
<213> ORGANISM: Dickeya

<400> SEQUENCE: 8
cagaccacca cggactggca gctggaaaag gtcgtcgaga tcagccgcca tggcgtccgc        60
cctcctaccg aaggcaacat gaagaccatc caagctggca ccggccgcgc ttggcccgaa       120
tggctgaccc gataccggcga gctgacgggc acggttatg ccgctgccgt gaagaagggc       180
cagtacgagg gcaactattt acgacagcac ggcctcctca cccaaggttg tccccagccc       240
ggtgagctgt tcgtctgggc cagccctctc cagcgaaccc gagagaccgc tatggccctc       300
atggacggcg tcttccccgg ttgtggcgtg gccattcaag gtcccgctag cgaggatcac       360
gacactttat tccacgccga ggacgctggt gtcacgctgg accaagctca agtcaaagcc       420
gctctcgacc atgctatgca aggtcagagc gccggccaga ttcagacccg actccagccc       480
gtcatcgaca agctgaagca agctgtctgt ctccccaaca ccgcttgtcc cgctttttgac       540 acggagtggg ccatcaagga aagcaagaaa ggcaacctct ctttacatgg ccccgaaacc       600
ctcgccaaca tggccgagac catccgcctc gcctacagca acaacaaccc tttaagccaa       660
gttgcctttg ccatgctcg cagcgccgct gaagtcggta ccctcctcac cctcgccacc       720
gcccagtatg acttcacgaa cgatttacct tatgtcgccc gacgcggtgc cagcaccctc       780
atgcaccaga tcgccctcgc cctcacgccc gaacaacgcc ccgatgcccc tcccgaagcc       840
aagtggctgc tctacgtcgc ccacgacacc aacatcgcca agctccgcac cttattaggc       900
ttcacttggc agcaaggtga ctaccctcga ggcaacatcc ctcccgctgg ctcgctcatc       960
ttcgagcgat ggcgcaatcc ccagtcgggc gagcgctttt tacgcatcta tttccaagct      1020
cagagcctcg accaaatccg caatttagac cctctggaca atcagcaccc ccccctccgc      1080
agcgagttta gcgtcgccgg ctgcgagaag accgaggtcg gtaccgtctg ccctttagac      1140
ggtgctctga gcgcctcaa tgacgccgtc gacaactcgg ccctcctccc cgttcagtac      1200
agccagtaa                                                             1209
```

```
<210> SEQ ID NO 9
<211> LENGTH: 426
<212> TYPE: PRT
<213> ORGANISM: Dickeya dadantii

<400> SEQUENCE: 9

Met Val Phe Thr Arg Lys Ile Ile Ala Gly Leu Leu Leu Ser Ala Leu
1                   5                   10                  15

Pro Trp Met Gly Ala Gln Ala Asp Thr Pro Ser Ser Gly Trp Thr Leu
            20                  25                  30
```

```
Glu Lys Val Val Glu Val Ser Arg His Gly Val Arg Pro Pro Thr Lys
        35                  40                  45

Gly Asn Val Lys Thr Ile Gln Glu Gly Thr Asp Arg Gln Trp Pro Thr
        50                  55                  60

Trp Leu Thr Gln Tyr Gly Glu Leu Thr Gly His Gly Tyr Ala Ala Ala
65                  70                  75                  80

Val Leu Lys Gly His Tyr Glu Gly Gln Tyr Leu Arg Gln His Gly Leu
                85                  90                  95

Leu Ser Gln Ala Cys Pro Ala Pro Gly Asp Val Phe Val Trp Ala Ser
                100                 105                 110

Pro Leu Gln Arg Thr Arg Glu Thr Ala Met Ala Leu Met Asp Gly Val
                115                 120                 125

Phe Pro Gly Cys Gly Val Ala Val Gln Gly Pro Glu Asp Glu Asp Asn
        130                 135                 140

Asp Pro Leu Phe His Ala Glu Ala Ala Gly Val Lys Leu Asp Gln Gln
145                 150                 155                 160

Gln Val Lys Ala Asp Leu Gln Asn Ala Met Gln Asp Lys Ser Ala Ala
                165                 170                 175

Gln Ile Gln Ala Gln Trp Gln Pro Ala Ile Asp Arg Leu Lys Gln Ala
                180                 185                 190

Val Cys Leu Pro Asp Lys Pro Cys Pro Ala Phe Ser Thr Pro Trp Glu
                195                 200                 205

Val Lys Glu Ser Lys Lys Gly Asn Ile Ser Leu His Gly Pro Glu Ala
        210                 215                 220

Leu Ala Asn Ile Ala Glu Thr Ile Arg Leu Ser Tyr Ser Asn Asn Asn
225                 230                 235                 240

Pro Leu Ser Glu Val Ala Phe Gly His Ala Lys Thr Ala Ala Glu Val
                245                 250                 255

Ala Ala Leu Met Pro Leu Leu Thr Ala Asn Tyr Asp Phe Thr Asn Asp
                260                 265                 270

Leu Pro Tyr Met Ala Arg Arg Gly Ala Ser Val Leu Met Asn Gln Ile
                275                 280                 285

Ala Leu Ala Leu Asn Thr Glu His Gln Ala Asp Val Pro Pro Asp Val
        290                 295                 300

Lys Trp Leu Leu Tyr Val Ala His Asp Thr Asn Ile Ala Lys Leu Arg
305                 310                 315                 320

Thr Met Leu Gly Phe Thr Trp Gln Met Gly Asp Tyr Pro Arg Gly Asn
                325                 330                 335

Ile Pro Pro Ala Gly Ser Leu Ile Phe Glu Arg Trp Arg Asn Gln Gln
                340                 345                 350

Ser Gly Gln Arg Leu Val Arg Ile Tyr Phe Gln Ala Gln Ser Leu Asp
        355                 360                 365

Gln Ile Arg Gly Leu Ala Ala Leu Asp Asp Ser His Pro Pro Leu Arg
        370                 375                 380

Ser Glu Phe Ser Met Ala Asp Cys Gln Lys Thr Asp Val Gly Thr Leu
385                 390                 395                 400

Cys Pro Tyr Asp Ala Val Met Lys Arg Leu Asn Asp Ala Val Asp Arg
                405                 410                 415

Thr Ala Leu Leu Pro Val Arg Tyr Thr Pro
                420                 425
```

```
<210> SEQ ID NO 10
<211> LENGTH: 1212
<212> TYPE: DNA
```

```
<213> ORGANISM: Dickeya dadantii

<400> SEQUENCE: 10 gacacccct cgagcggctg gacgctcgag aaggtcgtcg aagtcagccg ccatggcgtc      60
cgccctccta ccaagggcaa cgtcaagacg atccaagaag gcaccgaccg ccaatggcct     120
acttggctga cccagtatgg cgagctgacg ggccacggct acgctgccgc tgttttaaaa     180
ggccattacg agggccagta cctccgacag cacggcctcc tcagccaagc ttgtcccgct     240
cccggtgacg tctttgtctg ggctagccct ttacaacgca cgcgagagac cgccatggcc     300
ctcatggacg gtgtcttccc cggttgtggc gtcgccgtcc aaggtcccga agacgaggac     360
aacgaccctc tcttccacgc cgaggccgct ggtgtcaagc tcgaccagca gcaagttaag     420
gccgatttac agaacgccat gcaagataag agcgccgccc agatccaagc ccagtggcag     480
cccgctatcg accgtttaaa gcaagctgtc tgcctccccg ataagccttg tcccgctttc     540
agcacccctt gggaggtcaa agagtcgaag aagggcaaca tcagcctcca tggccccgaa     600
gccctcgcca acatcgccga gacgatccgt ttaagctata gcaacaacaa ccctttaagc     660
gaggtcgctt tcggtcacgc caagaccgcc gctgaagtgg ccgctttaat gcctctgctc     720
accgccaact acgactttac caacgattta ccctatatgg cccgccgagg cgctagcgtg     780
ctgatgaacc agattgccct cgctttaaac accgaacacc aagctgacgt ccctcccgac     840
gtcaagtggc tgctctacgt ggcccacgat acgaacatcg ccaagctccg caccatgctc     900
ggtttcactt ggcagatggg cgactaccct cgcggcaata ttccccccgc cggttcgctg     960
atcttcgagc gctggcgaaa tcaacagtcg ggccagcgtt tagtccgcat ctacttccaa    1020
gctcagtcgc tcgaccagat ccgaggttta gccgctctcg acgattcgca cccccctta    1080 cgaagcgagt tcagcatggc cgattgccag aagacggacg tgggcacgct ctgcccttac    1140
gacgccgtca tgaagcgact caacgacgct gtcgatcgaa ccgccttatt acccgtccgc    1200
tacacgccct aa                                                        1212

<210> SEQ ID NO 11
<211> LENGTH: 424
<212> TYPE: PRT
<213> ORGANISM: Bilophila wadsworthia

<400> SEQUENCE: 11

Met Lys Trp Gly Leu Ser Ile Leu Ala Leu Cys Ala Leu Leu Ala Ala
1               5                   10                  15

Thr Ala Pro Glu Gly Gly Ala Ala Glu Gln Gly Gly Gly Asp Ala Lys
            20                  25                  30

Leu Leu Lys Met Val Val Leu Ser Arg His Gly Val Arg Ser Pro Thr
        35                  40                  45

Gln Ser Ser Glu Thr Leu Glu Ser Trp Ser Arg Lys Asp Trp Pro Glu
        50                  55                  60

Trp Pro Val Lys Arg Gly Glu Leu Thr Pro Arg Gly Ala Lys Leu Val
65                  70                  75                  80

Thr Ala Met Trp Glu Gln Glu Ala Ala Phe Leu Arg Glu Ala Gly Leu
                85                  90                  95

Leu Pro Ser Lys Gly Cys Pro Glu Ala Gly Thr Ile Ala Val Arg Ala
            100                 105                 110

Asp Arg Asp Gln Arg Thr Arg Val Thr Gly Glu Ala Val Leu Glu Gly
        115                 120                 125
```

-continued

Leu Ala Pro Gly Cys Gly Phe Lys Pro Ile Val Asn Glu Thr Asp His
    130                 135                 140

Pro Asp Pro Leu Phe His Pro Leu Glu Ala Gly Tyr Cys Ala Leu Asp
145                 150                 155                 160

Pro Ala Val Val Arg Lys Glu Ile Pro Val Gly Ala Ile Glu Gly Leu
                165                 170                 175

Glu Gln Ser Leu Ser Gly Pro Ile Gly Glu Leu Ala Ala Ile Leu Gly
            180                 185                 190

Pro Ala Ser Pro Glu Phe Cys Arg Lys His Gln Leu Pro Glu Gly Cys
            195                 200                 205

Thr Val Ala Asp Val Pro Thr Arg Leu Thr Leu Ala Lys Asp Asn Arg
    210                 215                 220

Thr Val His Leu Asp Gly Lys Leu Gly Thr Ala Ser Ser Ala Ala Glu
225                 230                 235                 240

Ile Met Leu Leu Glu Tyr Gly Gln Trp Asp His Pro Ala Gly Trp Gly
                245                 250                 255

Ala Val Asp Lys Gly Ala Leu Gln Arg Leu Leu Pro Val His Ser Thr
            260                 265                 270

Val Phe Asp Ala Val Asn Arg Ala Pro Ser Val Ala Ala Gly Arg Gly
            275                 280                 285

Ser Glu Leu Leu Leu Asp Met Ala Asn Ala Leu Thr Gly Arg Tyr Ala
    290                 295                 300

Asp Pro Ala Val Asn Lys Ala Lys Val Val Val Phe Val Gly His Asp
305                 310                 315                 320

Thr Asn Ile Ala Asn Ile Gly Gly Met Leu Gly Leu His Trp Gln Leu
                325                 330                 335

Pro Gly Tyr Ala Pro Asp Glu Ile Pro Pro Ala Ser Ala Leu Val Leu
            340                 345                 350

Thr Leu Trp Leu Gln Asn Asp Val Tyr Gln Leu Arg Ala Arg Met Ile
            355                 360                 365

Gly Gln Ser Leu Asp Thr Leu His Asp Pro Ala Met Lys Gly Glu Val
    370                 375                 380

Leu Arg Gln Asp Ile Glu Val Pro Trp Cys Gly Pro Tyr Glu Asp Gly
385                 390                 395                 400

Lys Asn Cys Thr Leu Thr Asp Phe Glu Leu Arg Val Arg Asp Val Leu
            405                 410                 415

Arg Pro Glu Cys Val Arg Glu Arg
            420

<210> SEQ ID NO 12
<211> LENGTH: 1206
<212> TYPE: DNA
<213> ORGANISM: Bilophila wadsworthia

<400> SEQUENCE: 12
gccgagcaag gtggcggtga cgccaagctg ctcaagatgg tcgttttaag ccgccatggt      60
gtccgcagcc ctacgcagag cagcgagacg ctggagagct ggagccgcaa ggactggccc     120
gaatggcccg ttaagcgcgg tgagctcacc cctcgaggcg ccaagctggt gacggctatg     180
tgggagcaag aagccgcttt cctccgagag gccggtctcc tccctagcaa gggttgcccc     240
gaggctggca ccatcgccgt gcgagctgac cgagatcagc gcaccgcgt cacgggtgaa      300 gccgtcctcg agggtctggc ccccggttgc ggctttaagc ccatcgtcaa cgagaccgac     360
caccccgacc ctctcttcca cccttttagaa gctggctatt gcgccctcga ccccgctgtc     420

-continued

```
gtgcgcaagg agatccccgt gggcgccatc gagggcctcg aacagagcct cagcggtccc      480
attggtgagc tcgctgccat tctcggcccc gcttcgcccg aattctgccg aaagcaccag      540
ctccccgagg gctgtaccgt cgctgatgtc cctacccgcc tcactttagc caaggacaac      600
cgcaccgtcc acctcgatgg caagctgggt accgcctcga gcgccgccga gatcatgctc      660
ctcgaatacg gccagtggga tcaccccgcc ggttggggtg ctgtcgacaa gggtgcttta      720
cagcgactgc tgcccgttca gcacggtg ttcgacgccg tcaaccgcgc tccctcggtg      780
gccgccggtc gcggcagcga gctcttatta gatatggcca acgccctcac cggccgctac      840
gccgatcccg ccgtcaacaa ggccaaggtc gtcgtcttcg tcggccacga caccaatatc      900
gccaacattg gcggcatgct cggcctccac tggcagctcc ccggttacgc tcccgatgag      960
atccctcccg cttcggccct cgttttaacc ctctggctgc agaacgacgt ctaccagctc     1020
cgcgctcgca tgatcggcca gtcgctggac acgctccatg accccgctat gaagggcgaa     1080
gtgctgcgcc aagatatcga ggtcccttgg tgcggcccctt acgaggacgg caagaactgc     1140
actttaaccg acttcgagct gcgcgtccgc gatgtcctcc gccccgagtg tgtccgcgag     1200
cgctaa                                                                1206
```

<210> SEQ ID NO 13
<211> LENGTH: 403
<212> TYPE: PRT
<213> ORGANISM: Succinatimonas hippei

<400> SEQUENCE: 13

```
Met Lys Leu Leu Asn Lys Met Ser Ala Ala Cys Ala Val Ile Phe Ile
1               5                   10                  15

Ser Ser Phe Phe Gly Val Met Ala Ala Glu Asn Ser Phe Tyr Ala Phe
            20                  25                  30

Ala Pro Cys Ala Asp Ala Lys Leu Glu Lys Ile Val Val Leu Ser Arg
        35                  40                  45

His Gly Val Arg Ser Pro Thr Gln Asp Tyr Gln Thr Leu Ser Ser Trp
    50                  55                  60

Ser Lys Asn Asp Trp Pro Gln Trp Asn Val Pro Ser Gly Tyr Leu Thr
65                  70                  75                  80

Asp Arg Gly Tyr Phe Leu Ile Lys Ser Gln Trp Glu His Leu Lys Lys
                85                  90                  95

Ile Leu Ile Lys Asp Ser Val Tyr Lys Asn Asn Leu Phe Lys Ser Val
            100                 105                 110

Lys Ile Ile Ala Asp Ser Asp Gln Arg Thr Val Lys Thr Ala Glu Ala
        115                 120                 125

Ile Arg Glu Gly Ile Ser Ser Glu Asn Thr Ile Tyr Ser Asp Lys Lys
    130                 135                 140

Asp Val Tyr Pro Leu Phe His Pro Val Lys Ala Gly Ile Val Lys Leu
145                 150                 155                 160

Asn Ala Gln Asp Val Gln Glu Ser Ile Ile Asn Arg Val Asn Ser Thr
                165                 170                 175

Lys Gln Gln Asp Ala Ile Asn Leu Ile Gln Thr Ile Thr Asn Cys Cys
            180                 185                 190

Ser Gln Ser Ile Cys Gly Arg Asn Ala Pro Cys Asn Leu Ser Asn Ile
        195                 200                 205

Gln Asp Ser Val Thr Val Lys Asp Asn Asp Val Lys Leu Leu Gly Glu
    210                 215                 220
```

-continued

```
Lys Ala Ile Ala Ser Ser Ile Ala Glu Ile Phe Leu Leu Glu Tyr Gly
225                 230                 235                 240

Gln Trp Thr Asp Arg Asn Ala Gly Trp Gly Gln Val Asp Glu Lys Thr
                245                 250                 255

Leu Thr Lys Leu Leu Ser Leu His Asn Glu Val Phe Asp Ala Leu Asn
            260                 265                 270

Arg Gln Asn Ala Val Ala Leu Ser Arg Gly Gly Thr Leu Leu Asn Ala
            275                 280                 285

Leu Lys Asn Glu Ile Asn Asp Arg Ala Ser His Ile Ala Phe Phe Val
            290                 295                 300

Gly His Asp Thr Asn Ile Ser Asn Ile Gly Gly Leu Ala Asp Leu Thr
305                 310                 315                 320

Trp Ser Ile Pro Asp Gln Gly Val Asn Ser Ile Pro Pro Gly Cys Ala
                325                 330                 335

Ile Val Phe Leu Arg Trp Asn Ser Glu Thr Glu Asn Asn Gln Tyr Val
                340                 345                 350

Thr Ala Ala Ile Ala Ala Pro Ser Ile Lys Phe Ile His Ser Glu Asn
            355                 360                 365

Pro Asp Lys Glu Arg Leu Phe Leu Ile Ser Ala Asn Leu Asn Cys Glu
        370                 375                 380

Gly Lys Ile Cys Ser Leu Thr Lys Phe Asn Lys Lys Ile Asp Arg Ala
385                 390                 395                 400

Leu Asn Arg
```

```
<210> SEQ ID NO 14
<211> LENGTH: 1140
<212> TYPE: DNA
<213> ORGANISM: Succinatimonas hippei

<400> SEQUENCE: 14
gccgagaaca gcttctacgc cttcgctcct tgtgctgacg ccaagctgga gaagatcgtc      60
gtcctcagcc gacatggcgt gcgctcgcct acgcaagatt accagacgct cagcagctgg     120
agcaagaacg actggcctca gtggaacgtc cctagcggct acctcaccga ccgaggctac     180
tttctgatca agagccagtg ggagcacctc aaaaagattt taattaagga cagcgtctac     240
aaaaacaatt tattcaagtc ggtgaagatc atcgccgaca gcgaccagcg caccgtcaag     300
accgctgagg ccatccgcga gggcatctcg agcgagaaca cgatctatag cgacaagaag     360
gacgtgtacc ctctcttcca ccccgtgaaa gccggcattg tcaagctgaa tgcccaagat     420
gtccaagaaa gcatcatcaa ccgcgtcaac tcgaccaagc aacaagatgc tatcaatctg     480
attcagacga ttaccaactg ttgctcgcag agcatctgtg ccgcaacgc cccttgtaat     540 ttaagcaata tccaagattc ggtcacggtg aaggacaacg atgtcaagct gctgggcgag     600
aaggctatcg cttcgtcgat cgccgagatc ttttttactcg agtacggcca gtggaccgat     660
cgaaacgccg gctggggtca agtcgacgag aagaccctca cgaagttatt aagcctccac     720
aatgaggtct cgacgccct caaccgacag aacgccgtcg ccctctctcg tggtggcact     780
ttactgaacg ctctcaagaa cgagatcaac gaccgcgcca gccacatcgc ctttttcgtc     840
ggccacgaca cgaacatcag caacattggc ggcctcgccg acctcacttg gtcgatcccc     900
gatcaaggtg tgaactcgat cccccccggt tgcgccatcg tcttcctccg ctggaactcg     960
```

-continued

```
gaaaccgaga acaaccagta cgtcaccgcc gccatcgctg cccccagcat caagttcatc   1020
cacagcgaaa accccgacaa ggagcgcctc ttcctcatca gcgccaattt aaactgcgag   1080
ggcaagatct gttctttaac caagttcaac aagaagatcg accgcgcttt aaaccgctaa   1140
```

```
<210> SEQ ID NO 15
<211> LENGTH: 469
<212> TYPE: PRT
<213> ORGANISM: Blastobotrys adeninivorans

<400> SEQUENCE: 15

Met Leu Ser Val Leu Met Trp Ala Leu Pro Leu Val Val Ser Gly His
1               5                   10                  15

Leu Gln Val Leu Thr Pro Pro Ala Asp Asp Ile Leu Arg Leu Thr Gly
            20                  25                  30

Thr Lys Gly Pro Tyr Val Asp Arg Leu Ser Gln Gly Leu Glu Leu Asp
        35                  40                  45

Pro Pro Gln Gly Cys Ser Val Glu Gln Val Ile Met Val Met Arg His
    50                  55                  60

Gly Ala Arg Tyr Pro Thr Ala Asn Ala Tyr Pro Asp Leu Gln Gly Ala
65                  70                  75                  80

Leu Ala Lys Leu Glu Asn Lys Thr Phe Ser Ser Gly Pro Leu Gln Phe
                85                  90                  95

Phe Asn Asp Trp Thr Pro Tyr Val Asp Asn Leu Gly Trp Leu Glu Gln
            100                 105                 110

Glu Thr Phe Ser Gly Pro Tyr Ala Gly Leu Leu Ser Ala Tyr Gln Arg
            115                 120                 125

Gly Thr Glu Tyr Arg Ala Arg Tyr Gly His Leu Trp Asp Gly Glu Ser
        130                 135                 140

Ile Val Pro Phe Trp Ser Ser Asp Ser Glu Arg Val Ile Met Thr Ala
145                 150                 155                 160

Arg His Phe Gly Glu Gly Phe Phe Gly Tyr Asn Tyr Ser Thr Asn Ala
                165                 170                 175

Ala Leu Asn Ile Val Ser Glu Ala Glu Ser Gln Gly Ala Asn Ser Leu
            180                 185                 190

Thr Pro Val Cys His Ala Val Asp Pro Lys Ser Gly Asp Val Cys Ser
            195                 200                 205

Asn Leu Asn Val Lys Gln Ser Tyr Pro Leu Ala Ser Val Ala Ala Asp
        210                 215                 220

Arg Leu Asn Lys Arg Tyr Gly Leu Asn Leu Thr Gly Asp Asp Val Tyr
225                 230                 235                 240

Asn Leu Gln Gln Leu Ala Val Phe Glu Leu Asn Val Arg Gly Asp Ser
                245                 250                 255

Pro Trp Leu Asp Ala Phe Thr Arg Asp Glu Trp Val Ala Phe Asn Tyr
            260                 265                 270

Tyr Cys Gly Leu Asp Phe Phe Tyr Cys Lys Gly Pro Gly Ser Ala Gly
        275                 280                 285

Ser Val Ala Ala Gly Ser Val Val Ala Asn Ala Ser Leu Ser Leu Leu
        290                 295                 300

Gln Gln Gly Pro Ser Glu His Ala Gln Ala Gly Gly Lys Met Tyr Trp
305                 310                 315                 320

Asn Phe Ser His Asp Ser Asp Ile Val Pro Ile Leu Ala Ala Leu Gly
                325                 330                 335
```

-continued

```
Leu Ala Tyr Pro Asp Glu Lys Asp Val Pro Tyr Asn Gly Ser Ile Ala
            340                 345                 350

Phe Thr Ala Lys Tyr Asn Ala Val Asp Ile Met Pro Met Ala Gly His
            355                 360                 365

Val Val Phe Glu Arg Leu His Cys Thr Glu Asp Thr Pro Ala Trp Ser
            370                 375                 380

Ala Gly Thr Tyr Val Arg Val Ile Leu Asn Glu Gln Val Leu Pro Val
385                 390                 395                 400

Gln Asp Cys Gln Asn Gly Pro Gly Phe Ser Cys Lys Leu Glu Asp Tyr
                405                 410                 415

Ile Ala Arg Ala Lys Lys Arg Leu Val Asp Tyr Asn Ser Phe Cys Lys
                420                 425                 430

Thr Pro Asp Asp Trp Gln Lys His Leu Ser Phe Trp Trp Asn Pro Asn
            435                 440                 445

Thr Thr Gln Gln Tyr Asn Tyr Gln Lys Gly Pro Ile Gly Tyr Gln Gln
    450                 455                 460

Lys Thr Thr Leu Glu
465
```

```
<210> SEQ ID NO 16
<211> LENGTH: 1410
<212> TYPE: DNA
<213> ORGANISM: Blastobotrys adeninivorans

<400> SEQUENCE: 16
atgctcagcg tcctcatgtg ggccctgcct ctcgtcgtca gcggccacct ccaggtcctc      60
acgcctcctg ccgacgacat cctccgcctc accggcacga agggcccccta cgtcgaccgc     120 ctcagccagg gcctcgagct ggaccctcct cagggctgca gcgtcgagca ggtcatcatg     180
gtcatgcgcc acggcgctcg ctaccccacc gccaacgctt accccgacct ccagggcgct     240
ctcgccaagc tcgagaacaa gaccttcagc agcggccctc tccagttctt caacgactgg     300
acgccttacg tcgacaacct cggctggctc gagcaggaga ctttcagcgg cccgtacgcc     360
ggcctcctca gcgcctacca gcgcggcacc gagtacaggg cccgctacgg ccacctgtgg     420
gacggcgaga gcatcgtccc cttttggtcc tccgacagcg agcgcgtcat catgactgcc     480
cgccacttcg gcgagggctt tttcggctac aactacagca ccaacgccgc tctcaacatc     540
gtcagcgagg ccgagagcca gggcgccaac tcgctcacgc ccgtctgcca cgccgtcgat     600
cccaagagcg gcgacgtctg cagcaacctc aacgtcaagc agagctaccc tctcgccagc     660
gtcgccgccg accgcctgaa caagcgatac ggcctcaacc tgaccggcga cgacgtctac     720
aacctgcagc agctcgccgt cttttgagctg aacgtccgag cgacagcccc ctggctcgac     780
gccttcacgc gcgacgagtg ggtcgccttc aactactact gcggcctcga cttcttctac     840
tgcaagggcc ctggcagcgc cggctccgtc gctgccggct cggtcgtcgc caacgccagc     900
ctcagcctcc tccagcaggg ccccagcgag cacgcccagg ctggcggcaa gatgtactgg     960
aacttcagcc acgacagcga cattgtcccc atcctcgctg ccctcggcct ggcgtacccc    1020
gacgagaagg acgtcccccta caacggcagc attgccttca ccgccaagta caacgccgtg    1080
gacatcatgc ccatggctgg ccacgtcgtg ttcgagcgcc tccactgcac cgaggacacg    1140
cccgcctggt ccgccggcac ctacgtccgc gtcatcctca acgagcaggt tctccccgtc    1200
caggactgcc agaacggccc ctggcttcagc tgcaagcttg aggactacat tgcccgagcc    1260
aagaagcgcc tcgtcgacta caacagcttc tgcaagacgc ccgacgactg gcagaagcac    1320
```

```
ctctcgttct ggtggaaccc caacaccacg cagcagtaca actaccagaa gggccctatc    1380
ggctaccagc agaagaccac gctcgagtaa                                     1410

<210> SEQ ID NO 17
<211> LENGTH: 449
<212> TYPE: PRT
<213> ORGANISM: Wickerhamomyces ciferrii

<400> SEQUENCE: 17

Met Gln Leu Ser Thr Thr Val Leu Ser Ala Leu Ala Leu Ser Ile Thr
1               5                   10                  15

Ala Val Asp Ala Leu Pro Ile Gly Ser Lys Ser Glu Ser Ile Arg Pro
                20                  25                  30

Tyr Ser Gln Glu Ala Leu Asp Gln Phe Ser Val Leu Arg Phe Leu Gly
            35                  40                  45

Thr Ala Ser Pro Tyr Val Gln Asn Thr Gly Tyr Gly Ile Glu Arg Asp
        50                  55                  60

Ala Pro Tyr Gln Cys Lys Val Thr Gln Ala Asn Leu Ile Ser Arg His
65                  70                  75                  80

Gly Glu Arg Tyr Pro Thr Ser Asn Gln Gly Lys Lys Met Ala Lys His
                85                  90                  95

Phe Glu Gln Ile Gln Asn Gly Thr Glu Thr Ile Glu Gly Pro Leu Ser
                100                 105                 110

Phe Leu Lys Asp Tyr Glu Phe Lys Ala Leu Asp Glu Glu Gly Leu Asp
            115                 120                 125

Gln Glu Thr Gly Lys Gly Pro Tyr Ser Gly Leu Leu Asp Leu Tyr Lys
        130                 135                 140

His Gly Ala Leu Phe Arg Asp Arg Tyr Asp Asp Leu Tyr Asn Glu Gly
145                 150                 155                 160

Asp Glu Ile Lys Phe Tyr Ser Ala Ser Gln Lys Arg Val Val Glu Ser
                165                 170                 175

Ala Lys Lys Phe Ala Gln Gly Phe Leu Gly Glu Ser Tyr Asn Glu Ser
            180                 185                 190

Tyr Ile Gln Glu Ile Asp Glu Asp Thr Asn Asp Leu Gly Ala Asn Ser
        195                 200                 205

Leu Thr Pro Val Asn Ala Cys Asn Asn Tyr Asp Lys His Ile Asn Gln
    210                 215                 220

Asp Lys Ile Asp Glu Leu Ser Thr Ser Phe Leu Asn Lys Thr Ala Asp
225                 230                 235                 240

Arg Leu Asn Asn Gln Ser Pro Gly Ile Asn Leu Ile Pro Glu Gln Val
                245                 250                 255

Gly Ser Leu Ile Tyr Tyr Cys Gly Phe Glu Leu Asn Val Glu Gly Ser
            260                 265                 270

Asn Gln Ile Cys Glu Ile Phe Thr Thr Asp Glu Leu Leu Ala Tyr Ser
        275                 280                 285

Tyr Thr Lys Asp Val Ser Tyr Tyr Glu Lys Gly Pro Gly Asn Asn
    290                 295                 300

Leu Ser Ala Thr Ile Gly Ser Val Tyr Ile Asp Ala Ile Thr Arg Leu
305                 310                 315                 320

Ile Lys Asp Asp Ser Lys Asn Leu Thr Leu Ser Phe Ala His Asp Thr
                325                 330                 335

Asp Ile Phe Tyr Ile Val Ser Leu Leu Gly Leu Phe Asp Gly Glu Leu
            340                 345                 350
```

```
Pro Thr Asp His Gln Ser Phe Asn His Leu Trp Lys Ile Ser Asn Ile
        355             360             365

Ala Pro Met Gly Ala Arg Leu Val Ile Glu Arg Leu Glu Cys Glu Asp
    370             375             380

Gln Glu Glu Pro Phe Val Arg Ile Ile His Asn Asp Ala Val Leu Pro
385             390             395             400

Ile Pro Gly His Ser Glu Gly Pro Gly Tyr Ser Ile Ser Ile Ser Asp
            405             410             415

Phe Glu Lys Tyr Ile Glu Asp Lys Leu Asp Gly Lys Thr Tyr Glu Lys
            420             425             430

Asp Cys Gly Thr Lys Asp Gly Val Pro Thr Glu Leu Thr Phe Phe Trp
        435             440             445

Asp
```

<210> SEQ ID NO 18
<211> LENGTH: 1350
<212> TYPE: DNA
<213> ORGANISM: Wickerhamomyces ciferrii

<400> SEQUENCE: 18

```
atgcagctca gcaccaccgt cctcagcgcc ctcgctctca gcatcaccgc cgtcgacgcc      60
ctgcctatcg gcagcaagag cgagagcatt cgcccctaca gccaggaggc cctcgaccag     120
ttcagcgtcc tccgcttcct cggcaccgcc tcgccttacg tccagaacac cggctacggc     180
atcgagcgcg acgcccctta ccagtgcaag gtcacccagg ccaacctcat cagccgccac     240
ggcgagcgct accccaccag caaccagggc aagaagatgg ccaagcactt cgagcagatc     300
cagaacggca ccgagactat cgagggcccg ctcagcttcc tcaaggacta cgagttcaag     360
gccctggacg aggagggcct cgatcaggag actggcaagg ccccctactc cggcctcctc     420
gacctctaca gcacggcgc cctcttccgc gaccgctacg acgacctgta caacgagggc      480
gacgagatca agttctacag cgccagccag aagcgcgtcg tcgagagcgc caagaagttc     540
gcccagggct cctgggcga gctacaac gagtcgtaca tccaggagat cgacgaggac        600
accaacgacc tcggcgccaa ctcgctcacg cccgtcaacg cctgcaacaa ctacgacaag     660
cacatcaacc aggataagat tgacgagctg agcacctcgt tcctcaacaa gaccgccgac     720
cgcctcaaca accagtcgcc tggcatcaac ctcattccgg agcaggtcgg cagcctcatc     780
tactactgcg gcttcgagct taacgtcgag ggctccaacc agatctgcga gatcttcacc     840
accgacgagc tgctcgccta cagctacacc aaggacgtca gctactacta cgagaagggc     900
cctggcaaca acctgagcgc caccatcggc agcgtctaca tcgacgccat cacgcgcctc     960
atcaaggacg acagcaagaa cctcacgctg agcttcgccc acgacaccga catcttctac    1020
atcgtcagcc tgctcggcct cttcgacggc gagctgccca ccgaccacca gagcttcaac    1080
cacctctgga agatcagcaa cattgcccct atgggcgctc gcctcgtcat tgagcgcctc    1140
gagtgcgagg accaggagga gcccttcgtc cgcatcatcc acaacgacgc cgtcctgcct    1200
attcctggcc acagcgaggg ccctggctac agcatcagca tcagcgactt cgagaagtac    1260
atcgaggaca gctcgacggg caagacctat gagaaggact cggcaccaa ggatggcgtc     1320 cctaccgagc tgacgttctt ctgggactaa                                   1350
```

<210> SEQ ID NO 19
<211> LENGTH: 452
<212> TYPE: PRT
<213> ORGANISM: Daedalea quercina -continued

<400> SEQUENCE: 19

```
Met Thr Thr Leu Leu Cys Ile Ala Leu Thr Phe Tyr Ala Phe Cys Gly
1               5                   10                  15

Tyr Ile Ala Leu Gly Arg Pro Pro Asp Asp Ile Val Val Asp Ile Glu
                20                  25                  30

Ser Gly Glu Thr Gly Phe Ala Ala Asp Pro Ser Gly Phe Gly Ala Asp
            35                  40                  45

Ser Thr Asn Trp Ser Gln Tyr Ser Pro Tyr Tyr Pro Val Glu Pro Tyr
        50                  55                  60

Ser Ala Pro Pro Glu Gly Cys Val Val Asp Gln Val His Ile Ile Gln
65                  70                  75                  80

Arg His Gly Ala Arg Tyr Pro Thr Ser Gly Ala Ala Lys Arg Ile Gln
                85                  90                  95

Ala Ala Leu Ala Lys Leu Gln Thr Ala Thr Ile Gln Ser Asn Ser Ser
            100                 105                 110

Leu Ala Phe Ala Leu Asn Tyr Ser Tyr Thr Leu Gly Gln Asp Ser Leu
            115                 120                 125

Val Ser Leu Gly Ala Arg Glu Ser Tyr Gly Ala Gly Gln Glu Ala Tyr
        130                 135                 140

Ala Arg Tyr Ala Ser Ile Val Asp Ala Glu Lys Met Pro Phe Val Arg
145                 150                 155                 160

Ala Ser Gly Ser Glu Arg Val Val Gln Ser Ala Thr Asn Trp Thr Ala
                165                 170                 175

Gly Phe Ala Ala Ala Ser Asn Asp Val Tyr Thr Pro Val Leu Ser Val
            180                 185                 190

Ile Ile Ser Glu Gln Gly Asn Asp Thr Leu Asp Asp Ser Ser Cys Pro
            195                 200                 205

Leu His Thr Gly Ser Asp Ile Pro Gly Thr Tyr Ile Asp Val Tyr Ala
        210                 215                 220

Ala Asn Met Thr Asp Val Leu Asn Thr Gly Ala Tyr Gly Ala Asn Leu
225                 230                 235                 240

Ser Asn Ala Asp Thr His Ala Leu Val Thr Leu Cys Met Phe Glu Ser
            245                 250                 255

Val Ala Lys Glu Glu Arg Ser Ala Trp Cys Asp Leu Phe Ala Glu Leu
            260                 265                 270

Gly Ala Leu Asp Gly Phe Ala His Trp Ala Ala Leu Asp Lys Tyr Tyr
        275                 280                 285

Gly Thr Gly Tyr Gly Asn Glu Leu Gly Pro Val Gln Gly Val Gly Tyr
        290                 295                 300

Ile Asn Glu Leu Leu Ala Arg Leu Thr Asn Thr Pro Val Asn Asp Ser
305                 310                 315                 320

Thr Ser Thr Asn Ser Thr Leu Asp Ser Asn Pro Glu Thr Phe Pro Leu
            325                 330                 335

Asn Arg Thr Val Tyr Ala Asp Phe Ser His Asp Asn Leu Ile Ile Pro
            340                 345                 350

Val Phe Ala Ala Met Gly Leu Phe Pro Thr Asp Pro Leu Asp Pro Thr
        355                 360                 365

Gly Ala Ala Gly Gln Ala Thr Trp Asn Val Ser Thr Met Val Pro Phe
        370                 375                 380

Ala Gly Arg Met Val Val Glu Arg Leu Ala Cys Ala Gly Gly Glu Gly
385                 390                 395                 400
```

-continued

```
Gly Lys Tyr Val Arg Val Leu Val Asn Gln Ala Val Gln Pro Leu Val
            405                 410                 415

Phe Cys Gly Ala Glu Ala Asp Gly Val Cys Ser Leu Asp Ala Phe Val
            420                 425                 430

Glu Ser Gln Ala Tyr Ala Arg Ser Arg Gly Asn Gly Thr Trp Ala Ala
            435                 440                 445

Cys Phe Ala Ser
            450
```

```
<210> SEQ ID NO 20
<211> LENGTH: 1359
<212> TYPE: DNA
<213> ORGANISM: Daedalea quercina

<400> SEQUENCE: 20
atgaccacgc tcctctgcat tgccctgacc ttctacgcct tctgcggcta cattgccctc         60
ggccgacctc cggacgacat cgtcgtcgac atcgagagcg cgagactgg cttcgccgcc        120 gatcctagcg gctttggcgc cgacagcacc aactggtccc agtacagccc ttactacccc        180
gtcgagccct acagcgcccc tcctgagggc tgcgtcgtcg atcaggtcca catcatccag        240
cgccacggcg ctcgctaccc caccagcggc gctgccaagc gcatccaggc tgccctcgcc        300
aagctccaga ccgccaccat ccagagcaac agcagcctcg ccttcgctct caactacagc        360
tacaccctcg gccaggacag cctcgtcagc ctgggcgctc gcgagagcta cggcgctggc        420
caggaggctt acgcccgcta cgccagcatc gtcgacgccg agaagatgcc cttcgtccgc        480
gccagcggca gcgagcgcgt cgtccagagc gccacgaact ggaccgccgg ctttgccgct        540
gccagcaacg acgtctacac gcccgtcctc agcgtcatca tcagcgagca gggcaacgac        600
accctggacg acagcagctg ccctctccac accggcagcg acatccccgg cacctacatt        660
gacgtctacg ccgccaacat gaccgacgtc ctcaacaccg cgcctacgg cgccaacctc        720 agcaacgccg acacgcacgc cctcgtcacc ctctgcatgt tcgagagcgt cgccaaggag        780
gagcgcagcg cctggtgcga cctcttcgcc gagctgggcg ccctcgacgg cttcgcccac        840
tgggccgctc tggataagta ctacggcacc ggctacggca acgagcttgg ccccgtccag        900
ggcgtgggct acatcaacga gctgctcgcc cgcctcacca acactcccgt caacgactcc        960
acctccacca actcgaccct cgacagcaac cccgagactt tcccctcaa ccgcaccgtg       1020 tacgccgact tcagccacga caacctcatc atcccgtct ttgccgccat gggcctgttt       1080
ccgacggacc ctctcgaccc cacgggcgct gccggccagg ccacctggaa cgtcagcacg       1140
atggtcccct tcgctggccg catggtcgtc gagcgcctgg cctgcgctgg cggcgagggc       1200
ggcaagtacg tccgcgtcct cgtcaaccag gccgtccagc ctctcgtctt ttgcggcgct       1260
gaggccgacg gcgtctgcag cctcgacgcc tttgtcgaga gccaggccta cgctcgctcg       1320
cgcggcaacg gcacctgggc cgcctgcttc gccagctaa                            1359
```

```
<210> SEQ ID NO 21
<211> LENGTH: 453
<212> TYPE: PRT
<213> ORGANISM: Thermoascus aurantiacus

<400> SEQUENCE: 21

Met Tyr Leu Leu Leu Gly Val Leu Ala Gly Val Phe Ile Leu Ser Lys
1               5                   10                  15
```

-continued

```
Glu Ser Cys Ser Thr Val Asp Arg Gly Tyr Gln Cys Asn Pro Asn Ile
        20                  25                  30

Thr His Phe Trp Gly Gln Asn Ser Pro Tyr Phe Ser Leu Ser Asp Val
        35                  40                  45

Ser Glu Ile Ser Pro Glu Ile Pro Ala Gly Cys Ser Val Thr Phe Ala
    50                  55                  60

Gln Val Leu Ser Arg His Gly Ala Arg Tyr Pro Thr Ala Lys Lys Thr
65                  70                  75                  80

Gln Leu Tyr Ser Asp Ile Ile Thr Arg Ile Gln Gln Ser Ala Gln Ser
            85                  90                  95

Phe Asn Gly Asp Phe Ala Phe Leu Glu Arg Tyr Asn Tyr Thr Leu Gly
            100                 105                 110

Ala Glu Asp Leu Thr Ala Phe Gly Glu Asp Glu Met Thr Lys Ser Gly
            115                 120                 125

Ile Gln Phe Tyr Asn Arg Tyr Lys Thr Leu Ala Ser Ser Ile Val Pro
    130                 135                 140

Phe Val Arg Ala Ser Gly Ser Asp Arg Val Ile Ala Ser Gly Glu Arg
145                 150                 155                 160

Phe Leu Glu Gly Phe Gln Ser Ala Lys Met Met Asp Pro Ser Ser Asn
                165                 170                 175

Lys Asn Asp Ser Leu Pro Lys Ile Ser Val Ile Ile Ala Glu Ser Asp
            180                 185                 190

Ser Ser Asn Asn Thr Leu Asp His Ser Gly Cys Ala Ala Phe Glu Asp
            195                 200                 205

Asp Asn Thr Lys Asp Ile Val Gln Ser Glu Phe Leu Glu Val Phe Ala
    210                 215                 220

Pro Ala Val Leu Asp Arg Phe Lys Ala Gly Leu Pro Gly Val Asn Leu
225                 230                 235                 240

Ser Val Ser Asp Val Pro Asp Ile Met Asp Ile Cys Ala Phe Glu Thr
                245                 250                 255

Val Ala Asn Thr Pro Asp Ala Ser Gln Leu Ser Pro Phe Cys Ser Leu
            260                 265                 270

Phe Thr Glu Glu Glu Trp Leu Gln Tyr Asp Tyr Tyr Gln Ser Leu Gly
        275                 280                 285

Lys Tyr Tyr Gly Tyr Gly Asp Gly Asn Pro Leu Gly Ala Thr Gln Gly
    290                 295                 300

Val Gly Phe Val Asn Glu Leu Ile Ala Arg Leu Thr Asn Thr Pro Val
305                 310                 315                 320

Glu Asp His Thr Thr Val Asn His Thr Leu Asp Ser Asn Pro Glu Thr
                325                 330                 335

Phe Pro Leu Asn Ala Thr Leu Tyr Ala Asp Phe Ser His Asp Asn Thr
            340                 345                 350

Ile Ala Ser Ile His Ala Ala Leu Gly Leu Tyr Asn Gly Thr Lys Lys
            355                 360                 365

Leu Ser Thr Thr Arg Val Gln Ser Val Ala Glu Thr Asn Gly Tyr Ser
    370                 375                 380

Ala Ala Trp Thr Val Pro Phe Ser Ala Arg Thr Tyr Val Glu Met Met
385                 390                 395                 400

Gln Cys Ser Ser Glu Asn Glu Pro Phe Val Arg Ile Leu Val Asn Asp
                405                 410                 415

Arg Val Val Pro Leu His Gly Cys Glu Val Asp Ser Leu Gly Arg Cys
            420                 425                 430
```

-continued

```
Lys Arg Asp Asp Phe Val Arg Gly Leu Ser Phe Ala Arg Ser Gly Gly
        435                 440                 445

Asn Trp Ala Ser Cys
    450

<210> SEQ ID NO 22
<211> LENGTH: 1362
<212> TYPE: DNA
<213> ORGANISM: Thermoascus aurantiacus

<400> SEQUENCE: 22
atgtacctgc tcctcggcgt cctcgccggc gtctttatcc tcagcaagga gagctgcagc        60
accgtcgacc gaggctacca gtgcaacccc aacatcaccc acttttgggg ccagaacagc       120
ccctacttca gcctcagcga cgtcagcgag atcagccccg agattcctgc cggctgcagc       180
gtcacgttcg cccaggtcct cagccgccac ggcgctcgct accccaccgc caagaagacc       240
cagctctaca gcgacatcat cacccgcatc agcagagcg cccagagctt caacggcgac        300
ttcgccttcc tcgagcgcta caactacacc ctgggcgccg aggacctcac cgccttcggc       360
gaggatgaga tgaccaagag cggcatccag ttctacaacc gctacaagac cctcgccagc       420
agcatcgtcc ccttcgtccg cgccagcggc agcgaccgcg tcattgcctc cggcgagcgc       480
tttctcgagg gcttccagag cgccaagatg atggacccca gcagcaacaa gaacgactcg       540
ctccccaaga tcagcgtcat cattgccgag agcgacagct ccaacaacac cctcgaccac       600
agcggctgcg ccgccttcga ggacgacaac accaaggaca tcgtccagag cgagttcctc       660
gaggtctttg cccctgccgt cctcgaccgc ttcaaggctg cctgcctgg cgtcaacctc        720 agcgtgagcg acgtccccga catcatggac atctgcgcct ttgagactgt cgccaacacg       780
cccgacgcca gccagctgag cccttctgc agcctgttca ccgaggagga gtggctccag        840
tacgactact accagagcct cggcaagtac tacggctacg cgacggcaa ccctctcggc        900 gccacgcagg gcgtcggctt cgtcaacgag ctgatcgccc gcctcaccaa cactcccgtc       960
gaggaccaca ccaccgtcaa ccacacgctc gacagcaacc ccgagacttt tcccctcaac      1020
gccacgctct acgccgactt cagccacgat aacacgatcg ccagcatcca cgctgccctc      1080
ggcctctaca acggcaccaa gaagctcagc accacgcgcg tccagtccgt cgccgagact      1140
aacggctaca cgccgcctg acggtcccc ttcagcgccc gcacctacgt cgagatgatg        1200
cagtgcagca gcgagaacga gcccttttgtc cgcatcctgg tcaacgaccg agtcgtcccg     1260
ctccacggct gcgaggtcga cagcctcggc cgctgcaagc gcgacgactt cgtccgaggc      1320
ctcagcttcg cccgcagcgg cggcaactgg gccagctgct aa                        1362

<210> SEQ ID NO 23
<211> LENGTH: 466
<212> TYPE: PRT
<213> ORGANISM: Aspergillus oryzae

<400> SEQUENCE: 23

Met Ala Val Leu Ser Val Leu Leu Pro Ile Thr Phe Leu Leu Ser Ser
1               5                   10                  15

Val Ala Gly Thr Pro Val Thr Ser Pro Arg Gln Gln Ser Cys Asn Thr
            20                  25                  30

Val Asp Glu Gly Tyr Gln Cys Phe Ser Gly Val Ser His Leu Trp Gly
        35                  40                  45

Gln Tyr Ser Pro Tyr Phe Ser Val Asp Asp Glu Ser Leu Leu Ser Glu
    50                  55                  60
```

-continued

```
Asp Ile Pro Asp His Cys Gln Val Thr Phe Ala Gln Val Leu Ser Arg
65                  70                  75                  80

His Gly Ala Arg Tyr Pro Thr Glu Ser Lys Ser Glu Lys Tyr Ala Lys
                85                  90                  95

Leu Ile Lys Ala Val Gln His Asn Ala Thr Ser Phe Ser Gly Lys Tyr
            100                 105                 110

Ala Phe Leu Lys Ser Tyr Asn Tyr Ser Leu Gly Ala Asp Asp Leu Thr
            115                 120                 125

Pro Phe Gly Glu Asn Gln Leu Val Asp Ser Gly Ile Lys Phe Tyr Gln
    130                 135                 140

Arg Tyr Glu Glu Leu Ala Lys Asn Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Lys Ala Lys Leu Gly Asp Ser Lys Ser Lys Arg Gly Gln Pro Ala
            180                 185                 190

Pro Ile Val Asn Val Val Ile Thr Glu Thr Glu Gly Phe Asn Asn Thr
            195                 200                 205

Leu Asp His Ser Leu Cys Thr Ala Phe Glu Asn Ser Lys Thr Gly Asp
    210                 215                 220

Asp Ala Glu Asp Lys Phe Thr Ala Val Phe Thr Pro Ser Ile Ala Glu
225                 230                 235                 240

Arg Leu Glu Lys Asp Leu Pro Gly Thr Thr Leu Ser Ser Lys Glu Val
                245                 250                 255

Val Tyr Leu Met Asp Met Cys Ser Tyr Asp Thr Val Ala Leu Thr Arg
            260                 265                 270

Asp Gly Ser Arg Ile Ser Pro Phe Cys Ala Leu Phe Thr Gln Glu Glu
            275                 280                 285

Trp Val Gln Tyr Asp Tyr Leu Gln Ser Ile Ser Lys Tyr Tyr Gly Tyr
    290                 295                 300

Gly Ala Gly Asn Pro Leu Gly Pro Ala Gln Gly Ile Gly Phe Ala Asn
305                 310                 315                 320

Glu Leu Ile Ala Arg Leu Thr Lys Ser Pro Val Lys Asp His Thr Thr
                325                 330                 335

Thr Asn Thr Thr Leu Asp Ser Asn Pro Ala Thr Phe Pro Leu Asn Ala
            340                 345                 350

Thr Leu Tyr Ala Asp Phe Ser His Asp Asn Thr Met Thr Ser Val Phe
            355                 360                 365

Phe Ala Leu Gly Leu Tyr Asn Thr Thr Glu Pro Leu Ser Gln Thr Ser
    370                 375                 380

Val Gln Ser Thr Glu Glu Thr Asn Gly Tyr Ser Ser Ala Trp Thr Val
385                 390                 395                 400

Pro Phe Gly Ala Arg Ala Tyr Val Glu Met Met Gln Cys Thr Gly Glu
                405                 410                 415

Lys Glu Pro Leu Val Arg Val Leu Val Asn Asp Arg Val Ile Pro Leu
            420                 425                 430

Gln Gly Cys Asp Ala Asp Glu Tyr Gly Arg Cys Lys Arg Asp Asp Phe
            435                 440                 445

Ile Glu Gly Leu Ser Phe Val Thr Ser Gly Gly Asn Trp Gly Glu Cys
    450                 455                 460

Phe Ala
465
```

-continued

```
<210> SEQ ID NO 24
<211> LENGTH: 1401
<212> TYPE: DNA
<213> ORGANISM: Aspergillus oryzae

<400> SEQUENCE: 24
atggccgtcc tcagcgtcct cctgcctatc accttcctgc tcagcagcgt cgccggcacg       60
cccgtcacct cgcctcgcca gcagagctgc aacaccgtcg acgagggcta ccagtgcttc      120
agcggcgtca gccacctctg gggccagtac agcccctact tcagcgtcga cgacgagagc      180
ctcctcagcg aggacatccc cgaccactgc caggtcacgt tcgcccaggt cctcagccgc      240
cacggcgctc gctaccccac cgagagcaag agcgagaagt acgccaagct cattaaggcc      300
gtccagcaca cgccaccag cttctccggc aagtacgcct tcctcaagag ctacaactac      360
agcctgggcg ccgacgacct cacgcctttc ggcgagaacc agctcgtcga cagcggcatc      420
aagttctacc agcgctacga ggagctggcc aagaacgtcg tcccccttcat ccgcgccagc      480 ggcagcgacc gcgtcattgc cagcggcgag aagttcatcg agggcttcca gaaggccaag      540
ctcggcgact ccaagagcaa gcgcggccag cctgctccta tcgtcaacgt cgtcatcacc      600
gagactgagg gcttcaacaa caccctcgac cacagcctct gcaccgcctt cgagaacagc      660
aagaccggcg acgacgccga ggacaagttc accgccgtct ttacgccctc gatcgccgag      720
cgcctcgaga aggacctgcc tggcacgacc ctcagcagca aggaggtcgt ctacctcatg      780
gacatgtgca gctacgacac ggtcgccctc acgcgcgacg gcagccgcat cagcccctt      840 tgcgccctct tcacccagga gggagtgggtc cagtacgact acctcagag catcagcaag      900 tactacggct acggcgctgg caaccctctc ggccctgctc agggcatcgg cttcgccaac      960
gagctgatcg cccgcctcac caagtcgccc gtcaaggacc acaccaccac caacaccacg    1020
ctcgacagca accccgccac ctttcctctc aacgccacgc tctacgccga cttcagccac    1080
gacaacacca tgaccagcgt cttttcgcc ctcggcctct acaacaccac cgagcctctc    1140
agccagacct ccgtccagag caccgaggag actaacggct acagcagcgc ctggacggtc    1200 cccttggcg ctcgcgccta cgtcgagatg atgcagtgca cgggcgagaa ggagcccctc    1260
gtccgcgtcc tcgtcaacga ccgagtcatt cccctccagg gctgcgacgc cgacgagtac    1320
ggccgctgca gcgcgacga ctttatcgag ggcctcagct tcgtcaccag cggcggcaac    1380
tggggcgagt gcttcgccta a                                            1401

<210> SEQ ID NO 25
<211> LENGTH: 460
<212> TYPE: PRT
<213> ORGANISM: Ascosphaera apis

<400> SEQUENCE: 25

Met Leu Ile Leu Val Pro Phe Ile Leu Gly Ala Asn Ala Leu Ser Ile
1               5                   10                  15

Pro Ser Ser His Val Ser Thr Lys Asp Gly Ala Cys Ser Ser Pro Gly
            20                  25                  30

Asp Gly Tyr His Cys Phe Glu Glu Tyr Ser Arg Arg Trp Gly Glu Tyr
        35                  40                  45

Ser Pro Tyr Phe Ser Val Lys Asp Val Ser Ser Tyr Pro Val Asp Ile
    50                  55                  60

Pro Ser Glu Cys Glu Val Thr Phe Ala Gln Val Leu Ser Arg His Gly
65                  70                  75                  80
```

-continued

```
Ala Arg Tyr Pro Thr Ala His Lys Gly Lys Thr Tyr Ala Asp Leu Ile
            85                  90                  95

Glu Arg Ile Gln Asn Gln Thr Ala Arg Tyr Gly Ser Asp Phe His Phe
            100                 105                 110

Ile Glu Ser Phe Glu Tyr Ser Leu Asn Thr Asp Ser Leu Val Glu Phe
            115                 120                 125

Gly Lys Glu Gln Leu Phe Glu Ser Gly Val Ser Phe Tyr Glu Arg Tyr
    130                 135                 140

Ala Asn Leu Ser Arg Thr Asn Val Pro Phe Val Arg Ser Ser Trp Thr
145                 150                 155                 160

Pro Arg Val Ile Glu Ser Ala Glu His Phe Met Arg Gly Phe Ser Glu
                165                 170                 175

Ser Arg Lys Gln Ala Asn Gly Glu Pro Val Asn Lys Thr Ala Val Asp
            180                 185                 190

Val Val Met Tyr Asp Gly Thr Gly Phe Asn Ser Ser Leu Asn Leu Gly
            195                 200                 205

Ala Cys Pro Ala Phe Glu Lys Glu Ser Lys Ile Gln Pro Trp His Gln
    210                 215                 220

Gly Phe Met Glu Lys His Phe Ser Lys Thr Leu Gln Arg Val Lys Lys
225                 230                 235                 240

Asn Leu Pro Gly Ala Gln Leu Asp Val Lys Asp Ile Ile Tyr Leu Met
                245                 250                 255

Asp Leu Cys Ser Phe His Thr Val Ser Ala Thr Pro Asp Ala Thr Phe
            260                 265                 270

Leu Ser Pro Phe Cys Pro Leu Phe Thr Glu Glu Glu Trp Glu Ala Tyr
            275                 280                 285

Asp Tyr Phe Ser Thr Leu Arg Lys Tyr Tyr Lys Phe Gly Lys Gly Asn
    290                 295                 300

Glu Leu Ala Pro Pro Asn Gly Ile Ala Phe Val Asn Glu Leu Ile Ala
305                 310                 315                 320

Arg Leu Thr Asn Gln Pro Val His Asp His Ser Ser Ile Asn Arg Thr
                325                 330                 335

Leu Asp Ser Asp Pro Lys Thr Phe Pro Leu Gly Leu Pro Leu Tyr Ala
            340                 345                 350

Asp Phe Ser His Asp Asn Glu Met Ala Pro Ile Tyr Ala Ala Met Gly
            355                 360                 365

Ile Ala Gly Pro Ile Leu Asn Lys Lys Ser Ile Phe Gln Pro Glu Asp
    370                 375                 380

Val Ser Tyr Phe Thr Ser Ser Arg Leu Ile Pro Phe Ala Ala Arg Met
385                 390                 395                 400

Tyr Val Glu Lys Leu Glu Cys Gly Ser Glu Lys Glu Glu Tyr Val Arg
                405                 410                 415

Val Leu Ile Asn Asp Arg Val Met Pro Val Glu Gly Cys Ala Ala Asp
            420                 425                 430

His Leu Gly Arg Cys Lys Leu Ser Asp Phe Val Asn Gly Met Thr Tyr
            435                 440                 445

Ala Ser Ser Gly Tyr Ala Trp Lys Leu Cys Tyr Glu
    450                 455                 460
```

```
<210> SEQ ID NO 26
<211> LENGTH: 1383
<212> TYPE: DNA
<213> ORGANISM: Ascosphaera apis
```

-continued

<400> SEQUENCE: 26

```
atgctcattc tcgtcccttt catcctcggc gccaacgctc tcagcatccc cagcagccac        60
gtcagcacca aggacggcgc ctgcagcagc cctggcgacg gctaccactg cttcgaggag       120
tacagccgcc gctggggcga gtactctccc tacttcagcg tcaaggacgt cagcagctac       180
cccgtcgaca tcccctccga gtgcgaggtc acgttcgccc aggtcctcag ccgccacggc       240
gctcgctacc ccaccgctca caagggcaag acctacgccg acctcatcga gcgcatccag       300
aaccagacgg cccgctacgg cagcgacttc cacttcatcg agagcttcga gtactccctc       360
aacaccgaca gcctcgtcga gttcggcaag gagcagctgt cgagagcggc cgtcagcttc       420
tacgagcgct acgccaacct gagccgcacc aacgtgccct cgtccgcag cagctggacc       480 cctcgcgtca tcgagtccgc cgagcacttc atgcgcggct tcagcgagag ccgcaagcag       540
gccaacggcg agcccgtcaa caagaccgcc gtcgacgtcg tgatgtacga cggcaccggc       600
ttcaacagca gcctcaacct cggcgcttgc cccgccttcg agaaggagag caagatccag       660
ccttggcacc agggcttcat ggagaagcac ttcagcaaga ccctccagcg cgtcaagaag       720
aacctgcctg gcgctcagct cgacgtgaag gacatcatct acctcatgga cctctgcagc       780
ttccacaccg tcagcgcgac gcccgacgct accttcctct cgccgttctg ccctctgttc       840
accgaggagg agtgggaggc ctacgactac ttctcgaccc tccgcaagta ctacaagttt       900
ggcaagggca cgagctggc ccctcctaac ggcattgcct tcgtgaacga gctgatcgcc       960
cgcctcacca accagcctgt ccacgaccac agctccatca accgcacgct cgacagcgac      1020
cccaagacgt ttcccctcgg cctgcctctg tacgccgact tcagccacga caacgagatg      1080
gctcccatct acgccgccat gggcattgct ggcccattc tcaacaagaa gtccatcttt      1140
cagcccgagg acgtgagcta ctttaccagc agccgactca tcccccttcgc cgctcgcatg      1200 tacgtcgaga gctcgagtg cggctcggag aaggaggagt acgtccgcgt cctcatcaac      1260
gaccgcgtca tgcccgtcga gggctgcgcc gctgaccacc tcggccgctg caagctctcc      1320
gacttcgtca cggcatgac gtacgccagc agcggctacg cctggaagct ctgctacgag      1380
taa                                                                     1383
```

<210> SEQ ID NO 27
<211> LENGTH: 491
<212> TYPE: PRT
<213> ORGANISM: Thielaviopsis punctulata

<400> SEQUENCE: 27

```
Met Ala Pro Lys Asn Arg Arg Lys Leu Gln Phe Thr Leu Val Ser Met
1               5                   10                  15

Ala Ser Leu Leu Val Phe Ala Val Leu Ile Gly Met Arg Tyr Leu Phe
            20                  25                  30

Ser Ser Pro Ser Leu Leu Ser Thr Ser Ile Lys Pro Phe Ile Val Asn
        35                  40                  45

Arg Ser Pro His His Pro His Gly Ser Ser Ser Ala Cys Tyr Asp Cys
    50                  55                  60

Met Tyr Met Ala Thr Pro Ser Leu Trp Gly Gln Tyr Ser Pro Met Phe
65                  70                  75                  80

Ser Val Pro Ser Glu Leu Cys Ala Asp Val Pro Pro Lys Cys Thr Leu
                85                  90                  95

Thr Phe Gly Gln Val Leu Ser Arg His Gly Ala Arg Asp Pro Thr Ser
            100                 105                 110
```

```
Ser Lys Thr Val Glu Tyr Asn Arg Thr Ile Gln Arg Ile His Asp Ser
        115                 120                 125

Val Thr Glu Tyr Gly Glu Ala Val Lys Phe Leu Arg Asn Tyr Thr Tyr
    130                 135                 140

Ser Leu Gly Ala Asp His Leu Thr Lys Phe Gly Gln Asp Glu Met Met
145                 150                 155                 160

Val Ser Gly Val Asn Phe Phe Gln Arg Tyr Lys Ser Leu Ala Ala Ser
                165                 170                 175

Ser Val Pro Phe Ile Arg Ala Ser Gly Gln Gln Arg Val Val Glu Ser
                180                 185                 190

Ala Leu Asn Trp Thr Gln Gly Phe Tyr Ala Ala Arg Val Ser His Gly
                195                 200                 205

Ile Asp Pro Val Gly Glu Ser Lys Gly Lys Leu Leu Ile Ile Pro Glu
    210                 215                 220

Gly Asp Thr Ser Asn Asn Thr Leu Asn Asn Gly Leu Cys Thr Ala Leu
225                 230                 235                 240

Glu Ser Gly Lys Tyr Ser Gln Val Gly Asp Asp Ala Lys Asp Ala Phe
                245                 250                 255

Leu Ala Thr Phe Ile Glu Pro Ile Thr Ala Arg Leu Asn Leu Asn Leu
                260                 265                 270

Pro Gly Ala Asn Leu Thr Asn Lys Glu Ala Val Tyr Met Met Asp Leu
                275                 280                 285

Cys Pro Phe Asn Thr Val Ala Thr Ala Asp Ala Thr Val Ser Glu Phe
    290                 295                 300

Cys Leu Leu Phe Thr Ile Glu Asp Trp Arg Asn Tyr Asp Tyr Tyr Gln
305                 310                 315                 320

Thr Met Asp Lys Tyr Tyr Gly His Gly Asn Gly Asn Pro Met Gly Ala
                325                 330                 335

Thr Ser Gly Val Gly Trp Ala Asn Glu Leu Ile Ala Arg Leu Thr Asp
                340                 345                 350

Thr Pro Val Val Asp His Thr Ser Val Asn His Thr Leu Asp Ser Ser
                355                 360                 365

Asn Ala Thr Phe Pro Leu Gly Arg Ala Leu Tyr Ala Asp Phe Ser His
    370                 375                 380

Asp Asn Asp Met Thr Gly Ile Phe Ser Ala Leu Arg Leu Tyr Asp Ala
385                 390                 395                 400

Thr Pro Leu Leu Pro Thr Asp Arg Arg Val Ala Pro Glu Glu Ala Gly
                405                 410                 415

Gly Phe Ala Ser Ser Trp Val Val Pro Phe Ala Ala Arg Met Tyr Val
                420                 425                 430

Glu Lys Met Arg Cys Glu Gly Glu Ser Glu Glu Phe Val Arg Phe Leu
                435                 440                 445

Val Asn Asp Arg Val Ile Pro Leu Val Asp Cys Gly Val Asp Lys Phe
    450                 455                 460

Gly Arg Cys Lys Leu Ser Lys Trp Val Asp Thr Met Gly Phe Ala Gln
465                 470                 475                 480

Ser Gly Gly Asn Trp Ser Glu Cys Phe Ser Ser
                485                 490
```

<210> SEQ ID NO 28
<211> LENGTH: 1476
<212> TYPE: DNA
<213> ORGANISM: Thielaviopsis punctulata -continued

```
<400> SEQUENCE: 28 atggcccta agaaccgccg caagctccag ttcaccctcg tcagcatggc cagcctgctc        60
gtctttgccg tcctcatcgg catgcgctac ctcttcagca gccccagcct cctcagcacc       120
agcatcaagc ccttcatcgt caaccgctcg cctcaccatc ctcacggcag cagcagcgcc       180
tgctacgact gcatgtatat ggccacgcct agcctctggg gccagtacag ccccatgttc       240
agcgtcccca gcgagctgtg cgccgacgtg cctcctaagt gcaccctcac cttcggccag       300
gtcctcagcc gccacggcgc tcgcgacccc accagcagca agaccgtcga gtacaaccgc       360
accatccagc gcatccacga cagcgtcacc gagtacggcg aggccgtcaa gttcctccgc       420
aactacacct acagcctggg cgccgaccac ctcaccaagt ttggccagga cgagatgatg       480
gtcagcggcg tcaacttctt ccagcgctac aagagcctcg ccgccagctc ggtcccttc       540 atccgcgcca gcggccagca gcgcgtcgtc gagagcgccc tcaactggac ccagggcttc       600
tacgccgctc gcgtcagcca cggcatcgac cccgtcggcg agagcaaggg caagctcctc       660
atcatccccg agggcgacac cagcaacaac accctcaaca acggcctctg cacggccctc       720
gagagcggca agtacagcca ggtcggcgac gacgccaagg acgccttcct cgccaccttc       780
atcgagccca tcactgcccg cctcaacctc aacctgcctg cgccaacct gaccaacaag       840 gaggccgtct acatgatgga tctctgcccc ttcaacaccg tcgccaccgc cgacgccacc       900
gtcagcgagt tctgcctcct gttcaccatc gaggactggc gcaactacga ctactaccag       960
accatggaca agtactacgg ccatggcaac ggcaacccca tgggcgccac ctccggcgtc      1020
ggctgggcca acgagctgat cgcccgcctg accgacacgc ccgtcgtcga ccacaccagc      1080
gtcaaccaca cgctcgacag cagcaacgcc acctttcctc ttggccgcgc tctctacgcc      1140
gacttcagcc acgacaacga catgaccggc atcttcagcg ccctccgcct ctacgacgcc      1200
acgcctctgc tcccaccga ccgccgcgtc gctcccgagg aggctggcgg cttcgccagc      1260
tcctgggtcg tcccccttcgc tgcccgcatg tacgtcgaga agatgcgctg cgagggcgag      1320
agcgaggagt tcgtccgctt cctcgtcaac gaccgcgtca ttcccctcgt cgactgcggc      1380
gtcgacaagt tcggccgctg caagctcagc aagtgggtcg acaccatggg cttcgcccag      1440
agcggcggca actggtccga gtgcttcagc tcctaa                                1476

<210> SEQ ID NO 29
<211> LENGTH: 465
<212> TYPE: PRT
<213> ORGANISM: Magnaporthe oryzae

<400> SEQUENCE: 29

Met Phe Thr Leu Val Leu Leu Phe Gln Leu Trp Ser Ala Leu Ile Arg
1               5                   10                  15

Ala Thr His Ala Val Glu Pro Gly Ser Gln Gly Asp Cys Asp Thr Pro
            20                  25                  30

Asp Gly Gly Phe Gln Cys Asn Ser Ser Ile Ser His Asn Trp Gly Gln
        35                  40                  45

Tyr Ser Pro Phe Phe Leu Ala Pro Ser Glu Ile Asp Ala Ser Val Pro
    50                  55                  60

Ser Gly Cys Glu Val Thr Phe Ala Gln Ile Leu Ser Arg His Gly Ala
65                  70                  75                  80

Arg Asp Pro Thr Ala Ser Ala Thr Ala Ala Tyr Gly Glu Thr Ile Glu
                85                  90                  95
```

-continued

Gln Ile Gln Ser Ser Val Thr Asn Tyr Gly Glu Gly Phe Glu Phe Ile
            100                 105                 110

Lys Asp Tyr Gln Tyr Thr Leu Gly Ala Asp Gln Leu Ser Asp Phe Gly
            115                 120                 125

Arg Gln Glu Met Phe Asn Ser Gly Val His Phe Tyr Asn Arg Tyr Gln
            130                 135                 140

Ile Leu Ala Arg Asn Asn Thr Pro Phe Phe Arg Ser Asp Gly Gln Gln
145                 150                 155                 160

Arg Val Val Glu Ser Gly Gln Lys Trp Thr Glu Gly Phe His Gln Ala
                165                 170                 175

Leu Leu Gly Asp Ser Gly Arg Ala Gly Gly Pro Ala Asp Glu Phe Pro
                180                 185                 190

Tyr Lys Met Val Ile Ile Pro Asn Glu Asp Gly Thr Asn Asn Thr Leu
                195                 200                 205

Asn His Asn Leu Cys Thr Ala Phe Glu Asn Thr Lys Leu Gly Lys Glu
            210                 215                 220

Ala Gln Lys Glu Phe Met Glu Ser Ala Met Gly Gly Ile Thr Glu Arg
225                 230                 235                 240

Leu Asn Asn Gly Leu Glu Gly Ala Asn Leu Thr Thr Lys Gln Ala Val
                245                 250                 255

Gln Ile Met Glu Leu Cys Pro Phe Glu Thr Val Ala Asp Pro Gln Ala
                260                 265                 270

Thr Leu Ser Gln Phe Cys Thr Leu Phe Thr Gln Arg Asp Trp Glu Ala
                275                 280                 285

Tyr Asp Tyr Leu Gln Thr Leu Gly Lys Trp Tyr Gly Tyr Gly Asn Gly
            290                 295                 300

Asn Pro Leu Gly Ser Thr Gln Gly Val Gly Phe Val Asn Glu Leu Ile
305                 310                 315                 320

Ala Arg Leu Leu Gln Lys Pro Val Glu Asp His Thr Asn Thr Asn Ser
                325                 330                 335

Thr Leu Asp Ser Asp Pro Ser Thr Phe Pro Leu Asp Lys Lys Leu Tyr
                340                 345                 350

Ala Asp Phe Ser His Asp Asn Asp Met Leu Gly Ile Tyr Ala Ala Leu
            355                 360                 365

Gly Ile Tyr Asn Ala Thr Ala Pro Asp Ser Val Pro Lys Lys Glu Arg
            370                 375                 380

Arg Ser Ala Gln Glu Leu Ser Gly Phe Ser Ser Ser Trp Ala Val Pro
385                 390                 395                 400

Phe Ala Ala Arg Met Phe Val Glu Lys Met Thr Cys Ala Gly Gln Asn
                405                 410                 415

Glu Glu Leu Val Arg Ile Leu Val Asn Asp Arg Val Thr Pro Leu Gln
                420                 425                 430

Asn Cys Asp Ala Asp Ser Met Gly Arg Cys Thr Leu Ser Lys Phe Val
            435                 440                 445

Glu Ser Leu Ser Phe Ala Arg Ser Gly Gly Arg Trp Asp Gln Cys Phe
            450                 455                 460

Val
465

<210> SEQ ID NO 30
<211> LENGTH: 1338
<212> TYPE: DNA
<213> ORGANISM: Magnaporthe oryzae -continued

```
<400> SEQUENCE: 30
gtcgagcccg gtagccaagg tgactgcgac acgcccgacg gcggctttca gtgcaatagc      60
agcatctcgc ataactgggg ccagtactcg cccttctttt tagccccttc ggagatcgac     120
gcttcggtcc ccagcggttg cgaggtcacc ttcgcccaga ttctgtctcg tcacggtgcc     180
cgcgatccta cggcttcggc taccgccgcc tacggcgaga ccatcgagca aatccagagc     240
tcggtcacca actacggcga gggcttcgag tttatcaaag actaccaata caccctcggc     300
gctgatcagc tgagcgactt cggccgacaa gaaatgttca acagcggcgt ccacttctac     360
aaccgctacc agattttagc ccgcaacaac acgccctttt tccgctcgga cggtcaacag     420
cgcgtcgtcg agagcggtca gaagtggacg gagggtttcc accaagctct gctcggcgac     480
tcgggtcgcg ccggcggccc cgctgacgag ttcccctaca agatggtcat catccccaac     540
gaggacggta cgaacaatac cctcaaccat aatttatgca cggccttcga aaacaccaag     600
ctcggcaagg aggcccagaa agagttcatg gagtcggcca tgggtggcat taccgagcga     660
ctcaacaacg gtctcgaggg cgctaattta acgacgaagc aagctgtcca gatcatggag     720
ctgtgcccct ttgagaccgt cgccgatccc caagctactt tatcgcagtt ctgcaccctc     780
tttacgcagc gcgactggga ggcctacgac tacctccaga ccctcggcaa gtggtacggc     840
tacggcaacg gcaaccctct cggctcgacc caaggtgtcg gctttgtcaa cgagctcatc     900
gcccgcctcc tccagaagcc cgttgaggac cacacgaaca ccaactcgac tttagatagc     960
gaccccagca ccttcccttt agacaagaag ctgtacgccg acttctcgca cgacaacgac    1020
atgctgggca tctacgccgc tctgggcatc tataatgcca cggcccccga cagcgtgccc    1080
aagaaagagc gccgcagcgc ccaagaactg agcggcttca gcagcagctg ggctgtcccc    1140
ttcgctgccc gcatgtttgt cgagaagatg acgtgcgccg gtcagaacga ggagctcgtc    1200
cgcatcctcg tcaacgaccg cgtcacccccc ctccagaact gcgacgccga cagcatgggc    1260
cgctgcacgc tcagcaagtt tgtcgagtcg ctcagcttcg cccgaagcgg tggtcgctgg    1320
gaccagtgct ttgtctaa                                                   1338
```